(12) United States Patent
Zhao et al.

(10) Patent No.: US 6,716,821 B2
(45) Date of Patent: Apr. 6, 2004

(54) CYTOTOXIC AGENTS BEARING A REACTIVE POLYETHYLENE GLYCOL MOIETY, CYTOTOXIC CONJUGATES COMPRISING POLYETHYLENE GLYCOL LINKING GROUPS, AND METHODS OF MAKING AND USING THE SAME

(75) Inventors: Robert Yongxin Zhao, Watertown, MA (US); Michael Louis Miller, Somerville, MA (US); Wayne Charles Widdison, Somerville, MA (US); Ravi V. J. Chari, Newton, MA (US)

(73) Assignee: Immunogen Inc., Cambridge, MA (US)

(*) Notice: Subject to any disclaimer, the term of this patent is extended or adjusted under 35 U.S.C. 154(b) by 0 days.

(21) Appl. No.: 10/024,290

(22) Filed: Dec. 21, 2001

(65) Prior Publication Data

US 2004/0001838 A1 Jan. 1, 2004

(51) Int. Cl.[7] ............... A61K 31/70; A61K 31/535; C07H 15/24; C07D 491/00; C07D 305/00
(52) U.S. Cl. .......... 514/34; 514/229; 514/449; 530/391.7; 536/6.4; 540/462; 549/510
(58) Field of Search ............ 530/391.7, 391.9, 530/399; 424/178.1, 391.1; 514/229, 449, 34; 540/462; 549/510

(56) References Cited

U.S. PATENT DOCUMENTS 5,208,020 A    5/1993   Chari et al.
5,824,701 A    10/1998  Greenwald et al.

OTHER PUBLICATIONS

Zalipsky, *Bioconjugate Chem.,* 6:150–165 (1995).
Greenwald, *J. of Controlled Release,* 74:159–171 (2001).
Greenwald et al., *J. Org. Chem.,* 60:331–336 (1995).
Greenwald et al., *J. Med. Chem.,* 39:424–431 (1996).

*Primary Examiner*—Elli Peselev
(74) *Attorney, Agent, or Firm*—Sughrue Mion, PLLC

(57) ABSTRACT

Cytotoxic agents bearing a polyethylene glycol (PEG) linking group having a terminal active ester, cytotoxic conjugates comprising one or more cytotoxic agents linked to a cell-binding agent via PEG linking groups, and methods for producing both are disclosed. A therapeutic composition comprising a therapeutically-effective amount of one of the cytotoxic conjugates of the present invention, and a method of killing selected cell populations comprising contacting target cells, or tissue containing target cells, with an effective amount of one of the cytotoxic conjugates, are also disclosed.

92 Claims, 21 Drawing Sheets

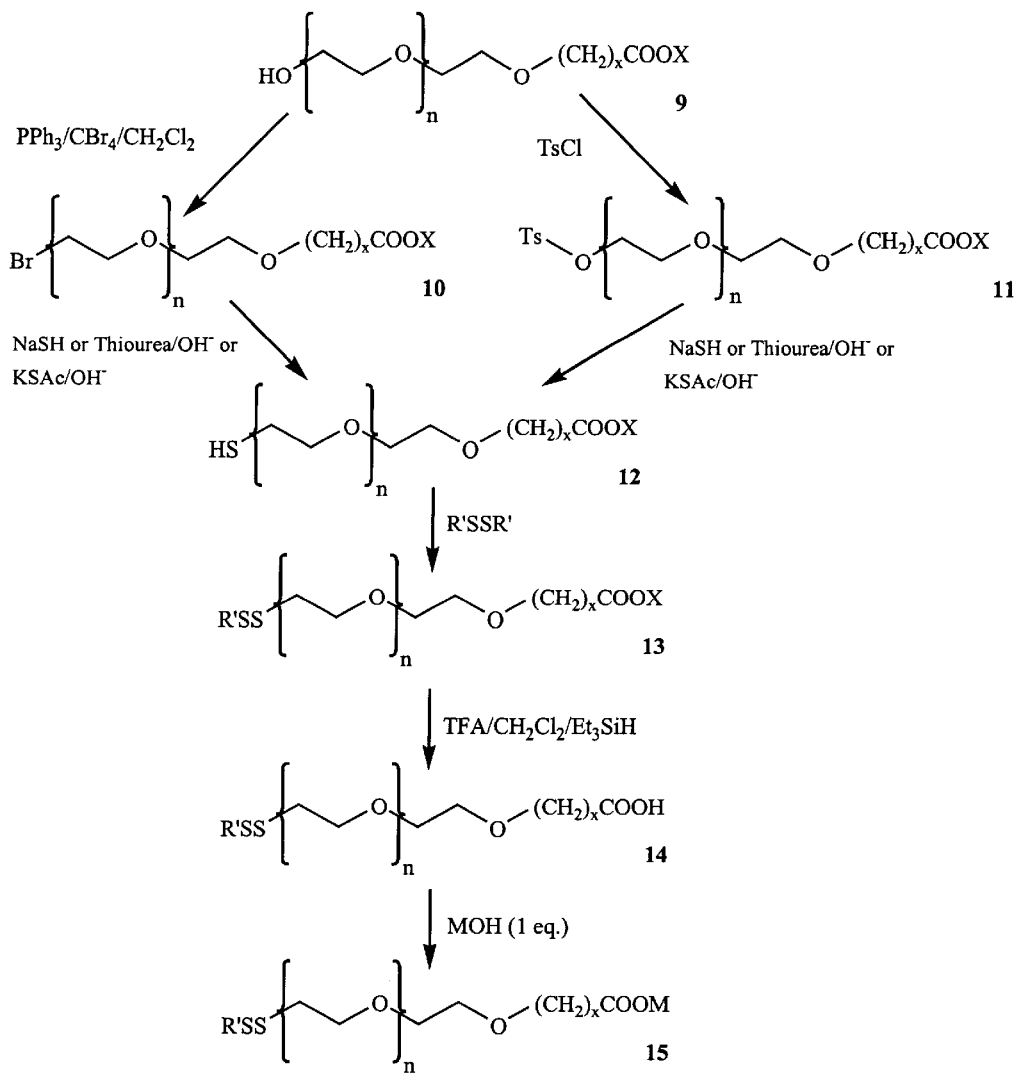

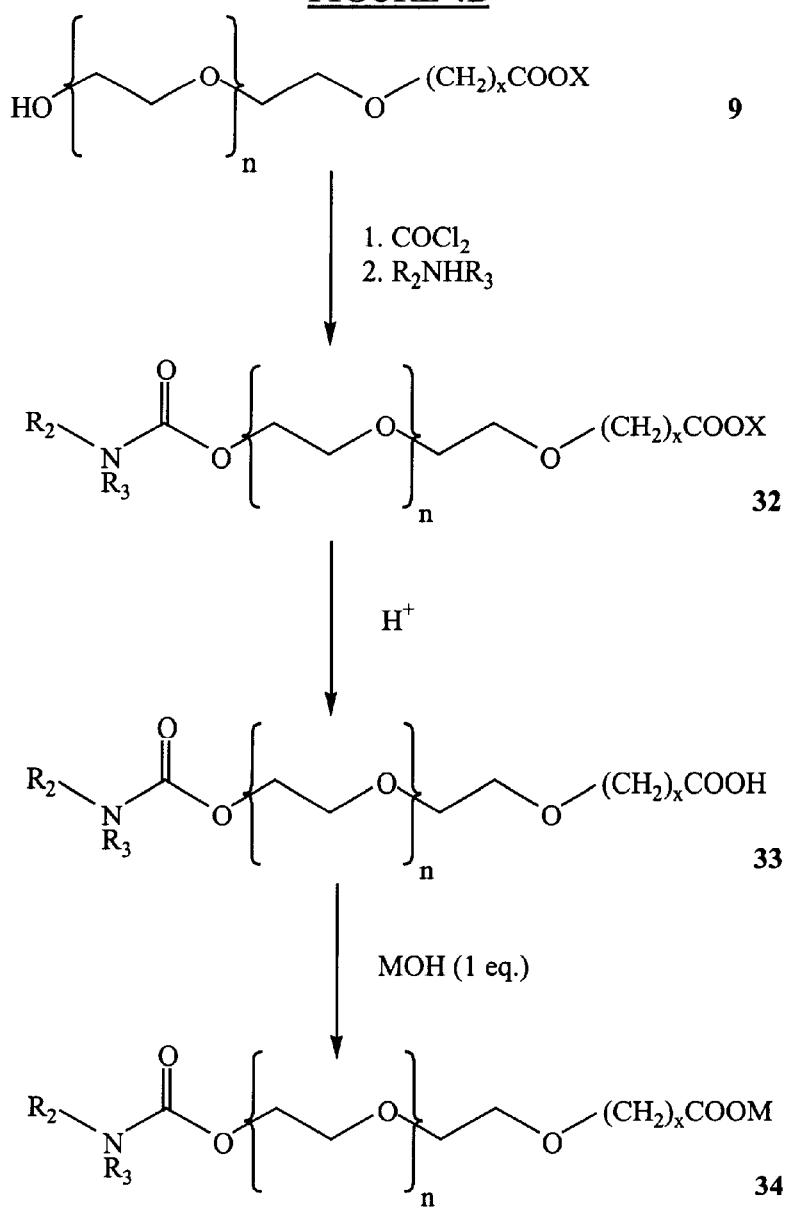

FIGURE 10
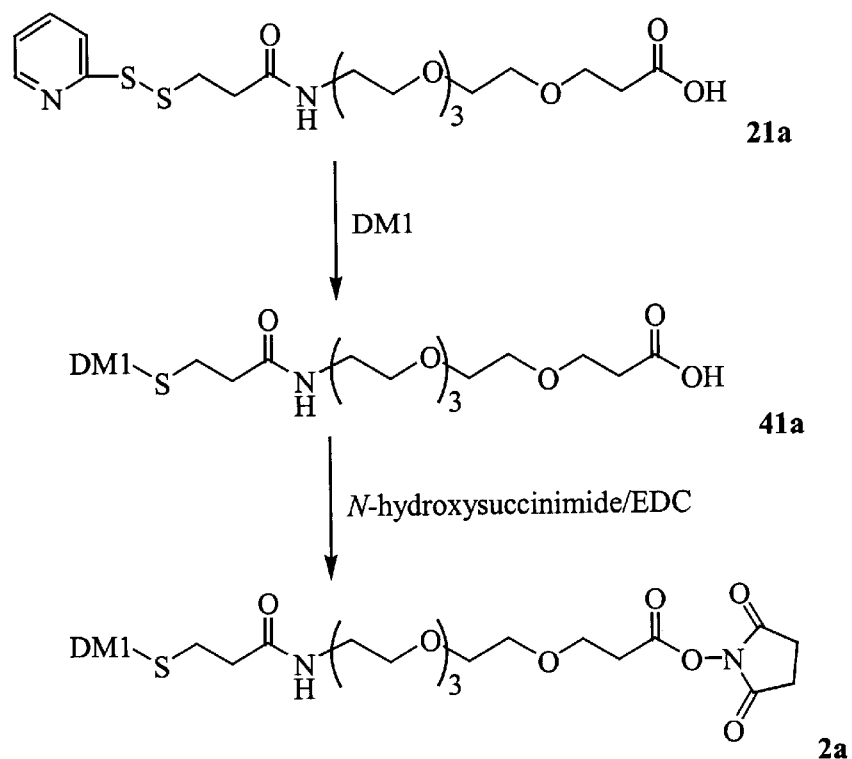
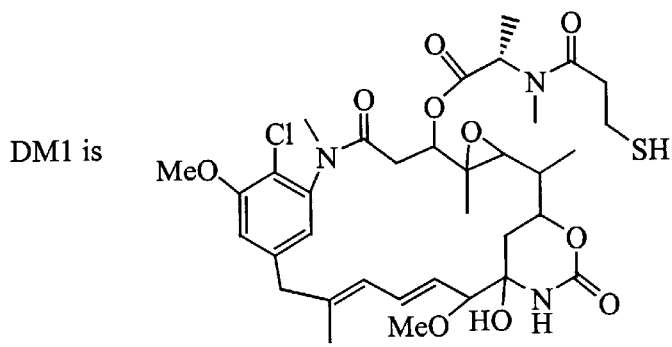

FIGURE 11
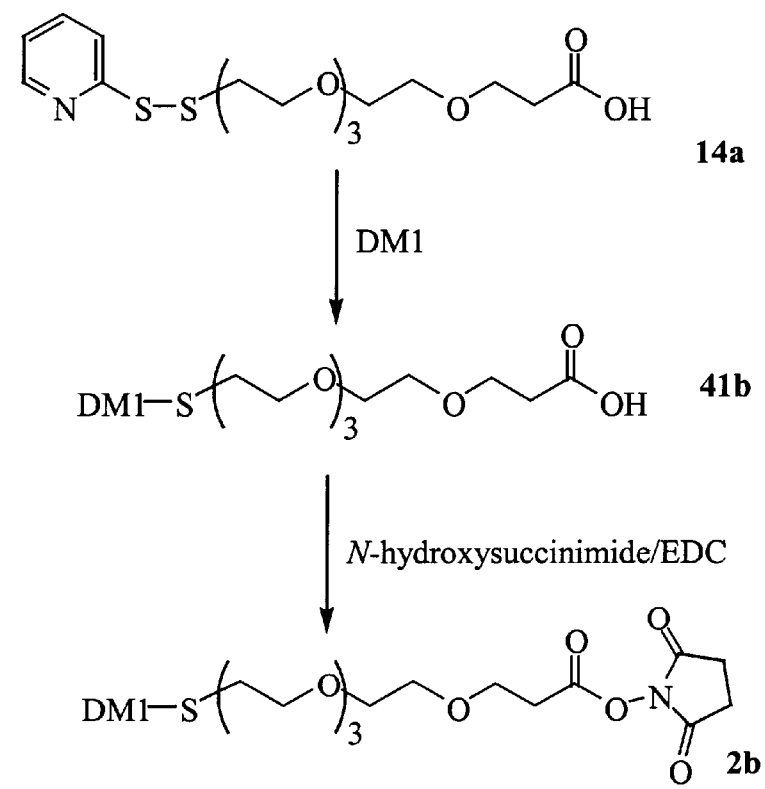
DM1 is 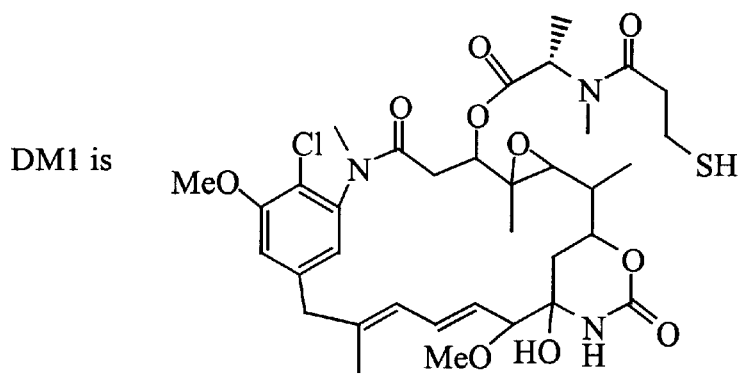

FIGURE 12
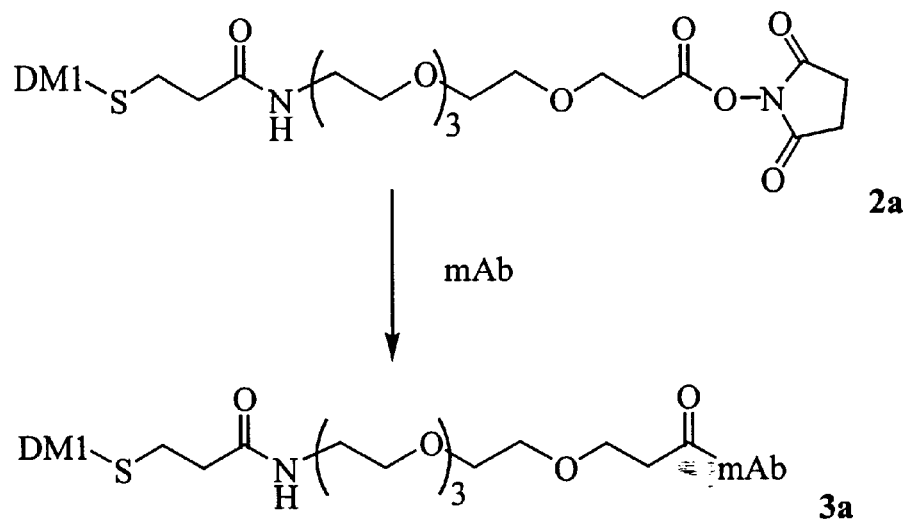
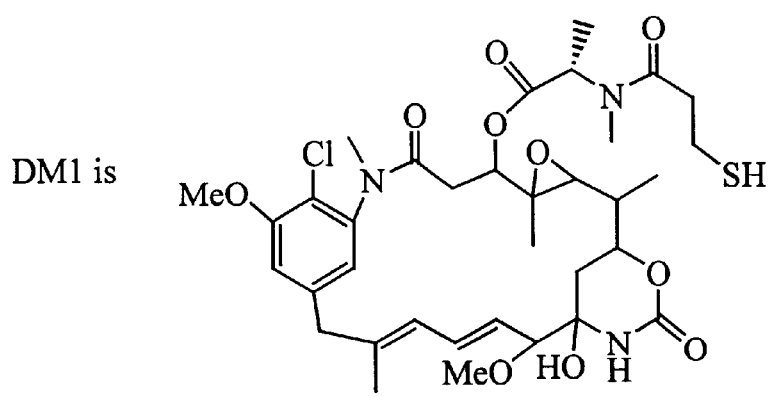

FIGURE 13

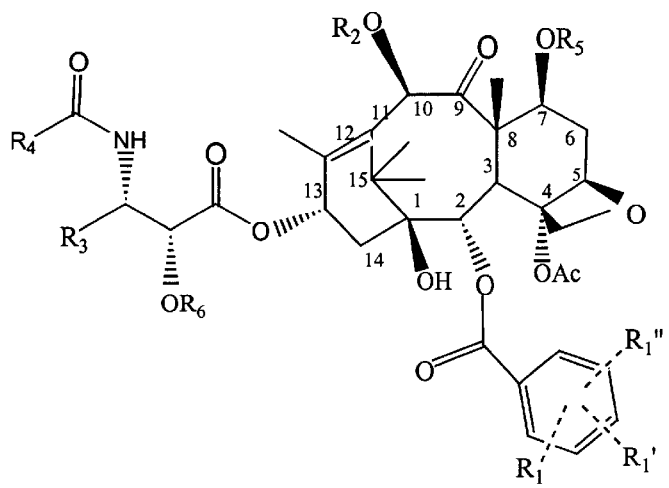

T1

| | $R_1$ | $R_2$ | $R_3$ | $R_4$ | $R_5$ | $R_6$ |
|---|---|---|---|---|---|---|
| (1) | -F | -COCH$_2$CH$_3$, -CH$_2$CH$_3$, or -CONHCH$_2$CH$_3$ | -CH$_2$CH(CH$_3$)$_2$ or –C$_6$H$_5$ | -OC(CH$_3$)$_3$ or –C$_6$H$_5$ | -CH$_2$CH$_2$SH or -COCH$_2$CH$_2$SH | -COCH$_2$CH$_3$, -CH$_2$CH$_3$, or CONHCH$_2$CH$_3$ |
| (2) | -F | -COCH$_2$CH$_3$, -CH$_2$CH$_3$, or -CONHCH$_2$CH$_3$ | -CH=C(CH$_3$)$_2$ or –C$_6$H$_5$ | -OC(CH$_3$)$_3$ or –C$_6$H$_5$ | -CH$_2$CH$_2$SH or -COCH$_2$CH$_2$SH | -COCH$_2$CH$_3$, -CH$_2$CH$_3$, or CONHCH$_2$CH$_3$ |
| (3) | -F | -COCH$_2$CH$_2$SH -CH$_2$CH$_2$SH | -CH$_2$CH(CH$_3$)$_2$ or –C$_6$H$_5$ | -OC(CH$_3$)$_3$ or –C$_6$H$_5$ | -COCH$_2$CH$_3$, -CH$_2$CH$_3$, or -CONHCH$_2$CH$_3$ | -COCH$_2$CH$_3$, -CH$_2$CH$_3$, or CONHCH$_2$CH$_3$ |
| (4) | -F | -COCH$_2$CH$_3$, -CH$_2$CH$_3$, or -CONHCH$_2$CH$_3$ | -CH$_2$CH(CH$_3$)$_2$ or –C$_6$H$_5$ | -OC(CH$_3$)$_3$ or –C$_6$H$_5$ | -COCH$_2$CH$_3$, -CH$_2$CH$_3$, or -CONHCH$_2$CH$_3$ | -CH$_2$CH$_2$SH or COCH$_2$CH$_2$SH |

CYTOTOXIC AGENTS BEARING A REACTIVE POLYETHYLENE GLYCOL MOIETY, CYTOTOXIC CONJUGATES COMPRISING POLYETHYLENE GLYCOL LINKING GROUPS, AND METHODS OF MAKING AND USING THE SAME

FIELD OF THE INVENTION

The present invention relates to cytotoxic agents bearing reactive polyethylene glycol linkers and methods for making such agents. These agents may be used in the production of cytotoxic conjugates, or for other purposes, such as in an affinity resin for use in the isolation of cellular components that recognize and bind the cytotoxic agents.

The present invention also relates to novel cytotoxic conjugates comprising polyethylene glycol linkers, methods of making the conjugates, and their therapeutic use. More specifically, the invention relates to novel cytotoxic conjugates comprising cytotoxic agents joined to cell-binding agents using hetero-bifunctional polyethylene glycol linkers, methods for making the conjugates and their therapeutic use. These novel cytotoxic conjugates have therapeutic use in that the cytotoxic portion of the conjugates can be delivered to specific cell populations in a targeted fashion, due to the linkage of the cytotoxic agent to a cell-binding agent.

BACKGROUND OF THE INVENTION

Conjugates of highly cytotoxic agents, such as maytansinoids and CC-1065 analogs, and cell-binding agents have been shown to possess exceptional target-specific anti-tumor activity (U.S. Pat. Nos. 5,208,020, 5,416,064, 5,475,092, 5,585,499, and 5,846,545). In such cytotoxic conjugates, the cytotoxic agent is bound to the cell-binding agent via a disulfide bond or via a short disulfide-containing linker. It has been previously shown that such disulfide-containing linkers are both stable upon storage, and efficiently cleaved inside a tumor cell to release fully active drug (Liu et al., Proc. Natl. Acad. Sci. 93:8618–8623 (1996); Chari et al., Cancer Res. 55:4079–4084 (1995); Chari, R. V. J., Adv. Drug Delivery Rev. 31:89–104 (1998)). Cleavage likely occurs via disulfide exchange between the disulfide-linked cytotoxic agent and an intracellular thiol, such as glutathione.

However, because most highly-potent cytotoxic agents used in cytotoxic conjugates are hydrophobic, two technical difficulties arise. The first is that conjugation reactions between cytotoxic agents and cell-binding agents require reaction conditions that address the hydrophobic nature of the cytotoxic agents. These conditions include very dilute solutions, the use of large volumes, and the presence of large amounts of non-aqueous co-solvents, which may damage the proteinacious cell-binding agents. As a result, preparation and purification processes become quite cumbersome, and the final cytotoxic conjugate is obtained in low concentration, necessitating the administration of large volumes to patients.

The second technical difficulty is that cytotoxic conjugates prepared using disulfide bonds or short disulfide-containing linkers are only sparingly soluble in pharmaceutical solutions typically used for parenteral administration to patients. It is therefore difficult to produce formulations for such conjugates.

Thus, in order to develop improved methods for producing cytotoxic conjugates, and increase the flexibility in formulating pharmaceutical solutions containing the conjugates, there is a need to address the hydrophobicity of both the cytotoxic agents and the cytotoxic conjugates produced using cytotoxic agents.

One manner in which to meet both of these goals would be to develop novel linker molecules that allow the hydrophobic cytotoxic agents to be manipulated under aqueous conditions and permit the formation of a cytotoxic conjugate that is soluble under both aqueous and non-aqueous conditions.

Polyethylene glycol (PEG) has been found to be useful in the conversion of cytotoxic drugs into prodrugs, thereby extending the half-life of the drugs in circulation in vivo, and improving their water solubility (for a review see Greenwald, R. B., J. Controlled Release 74:159–171 (2001)). For example, the anti-cancer drug Taxol has been converted into the prodrug PEG-Taxol by linking PEG via an ester bond to the C-2' position of Taxol (U.S. Pat. No. 5,824,701; Greenwald et al., J. Med. Chem. 39:424–431 (1996); Greenwald et al., J. Org. Chem. 60:331–336 (1995)).

However, PEG used in such applications is usually very large (average molecular weight of 40,000). Such size is required to significantly alter the pharmacokinetics of the drug. The drug molecules are also typically reacted with PEG via an ester or carbamate group of the drug, which can result in a drastic decrease in drug potency. In addition, the PEG moiety must be cleaved in vivo by some enzymatic mechanism to restore the activity of the drug, a process which is often inefficient. Finally, PEG used in such applications is typically mono-functional, i.e., only one terminus of the PEG molecule is modified so that it can be linked to the drug.

The present inventors have prepared novel PEG linking groups that provide a solution to both of the difficulties discussed above. These novel PEG linking groups are soluble both in water and in non-aqueous solvents, and can be used to join one or more cytotoxic agents to a cell-binding agent. The PEG linking groups are hetero-bifunctional linkers in that they bind to cytotoxic agents and cell-binding agents at opposite ends of the linkers through a functional sulfhydryl or disulfide group at one end, and an active ester at the other end. The linking groups have the two-fold advantage over other linking groups in that (1) they can be chemically joined to a cytotoxic agent in a non-aqueous solvent via a disulfide bond, thereby surmounting the hydrophobic nature of the agent and making it soluble in both non-aqueous and aqueous solvents, and (2) cytotoxic conjugates produced using the linking groups have greater solubility in water, thereby permitting much greater flexibility in the formulation of pharmaceutical solutions for parenteral administration to patients.

Thus, herein disclosed are cytotoxic agents bearing a PEG linking group having a terminal active ester, and cytotoxic conjugates comprising one or more cytotoxic agents joined to a cell-binding agent via a PEG linking group. In addition, a therapeutic composition comprising a cytotoxic conjugate is disclosed.

Also disclosed are methods of preparing cytotoxic agents bearing a PEG linking group having a terminal active ester, and methods of preparing cytotoxic conjugates comprising one or more cytotoxic agents joined to a cell-binding agent via a PEG linking group. Finally, a method for killing selected cell populations using cytotoxic conjugates is disclosed.

SUMMARY OF THE INVENTION

In one embodiment of the invention, cytotoxic agents bearing a polyethylene glycol (PEG) linking group having a terminal active ester are disclosed. The cytotoxic agents contemplated in this, and each proceeding embodiment, include a thiol-containing maytansinoid, thiol-containing taxane, thiol-containing CC-1065 analogue, thiol-containing daunorubicin analogue and thiol-containing doxorubicin analogue, and thiol-containing analogues or derivatives thereof. The core of the terminal active esters of the PEG linking group contemplated in this, and each proceeding embodiment, are esters that readily react with amino groups, including N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl esters.

In a preferred embodiment, the PEG linking group has from 1 to 20 monomeric units. In an equally preferred embodiment, the PEG linking group has from 21 to 40 monomeric units. In a further equally preferred embodiment, the PEG linking group has from 41 to 1000 monomeric units.

Specifically contemplated is a cytotoxic agent, bearing a polyethylene glycol (PEG) linking group having a terminal active ester and 1 to 20 monomeric units, of formula 2:

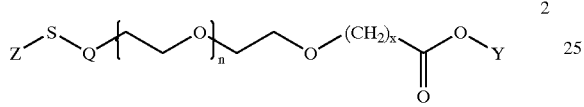

wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or S—,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 0 to 20;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

Also contemplated is a cytotoxic agent, bearing a PEG linking group having a terminal active ester and 21 to 40 monomeric units, of formula 2:

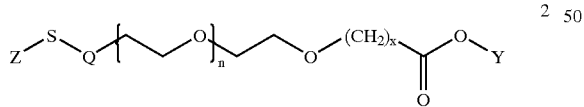

wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or S—,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 21 to 40;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

Also contemplated is a cytotoxic agent, bearing a PEG linking group having a terminal active ester and 41 to 1000 monomeric units, of formula 2:

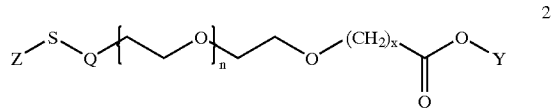

wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or S—,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 41 to 1000;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

Also contemplated is the cytotoxic agent according to any one of the examples above, wherein said cytotoxic agent is selected from the group consisting of a thiol-containing maytansinoid, thiol-containing taxane, thiol-containing CC-1065 analogue, thiol-containing daunorubicin analogue and thiol-containing doxorubicin analogue, and thiol-containing analogues or derivatives thereof.

Also contemplated is the cytotoxic agent according to the relevant examples above, wherein said thiol-containing maytansinoid is a C-3 thiol-containing maytansinoid.

Also contemplated is the cytotoxic agent according to the relevant examples above, wherein said C-3 thiol-containing maytansinoid is an N-methyl-alanine-containing C-3 thiol-containing maytansinoid.

Also contemplated is the cytotoxic agent according to the relevant examples above, wherein said N-methyl-alanine-containing C-3 thiol-containing maytansinoid is a compound selected from the following formula M1:

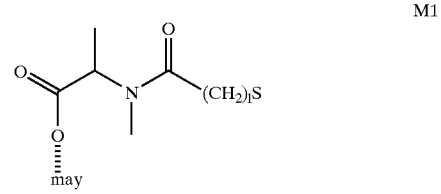

wherein:
l is an integer of from 1 to 10; and
may is a maytansinoid.

Also contemplated is the cytotoxic agent according to the relevant examples above, wherein said N-methyl-alanine-containing C-3 thiol-containing maytansinoid is a compound selected from the following formula M2:

M2 wherein:

R$_1$ and R$_2$ are H, CH$_3$ or CH$_2$CH$_3$, and may be the same or different;

m is 0, 1, 2 or 3; and may is a maytansinoid.

Also contemplated is the cytotoxic agent according to the relevant examples above, wherein said N-methyl-alanine-containing C-3 thiol-containing maytansinoid is a compound selected from the following formula M3:

M3 wherein:

n is an integer of from 3 to 8; and may is a maytansinoid.

Also contemplated is the cytotoxic agent according to the relevant examples above, wherein said N-methyl-alanine-containing C-3 thiol-containing maytansinoid is a N-methyl-alanine-containing C-3 thiol-containing maytansinol.

Also contemplated is the cytotoxic agent according to the relevant examples above, wherein said N-methyl-alanine-containing C-3 thiol-containing maytansinol is a dechloro maytansinol.

Also contemplated is the cytotoxic agent according to the relevant examples above, wherein said N-methyl-alanine-containing C-3 thiol-containing maytansinol is a compound selected from the following formula M6:

M6 wherein:

l is 1, 2 or 3;

Y$_0$ is Cl or H; and

X$_3$ is H or CH$_3$.

Also contemplated is the cytotoxic agent according to the relevant examples above, wherein said C-3 thiol-containing maytansinoid is an N-methyl-cysteine-containing C-3 thiol-containing maytansinoid.

Also contemplated is the cytotoxic agent according to the relevant examples above, wherein said N-methyl-cysteine-containing C-3 thiol-containing maytansinoid is a compound selected from the following formula M4:

M4 wherein:

o is 1, 2 or 3;

p is an integer of 0 to 10; and may is a maytansinoid.

Also contemplated is the cytotoxic agent according to the relevant examples above, wherein said N-methyl-cysteine-containing C-3 thiol-containing maytansinoid is a N-methyl-cysteine-containing C-3 thiol-containing maytansinol.

Also contemplated is the cytotoxic agent according to the relevant examples above, wherein said N-methyl-cysteine-containing C-3 thiol-containing maytansinol is a dechloro maytansinol.

Also contemplated is the cytotoxic agent according to the relevant examples above, wherein said N-methyl-cysteine-containing C-3 thiol-containing maytansinol is a compound selected from the following formula M5:

M5 wherein:

o is 1, 2 or 3;

q is an integer of from 0 to 10;

Y$_0$ is Cl or H; and

X$_3$ is H or CH$_3$.

Also contemplated is the cytotoxic agent according to the relevant examples above, wherein said thiol-containing taxane is a compound selected from the following formula T1:

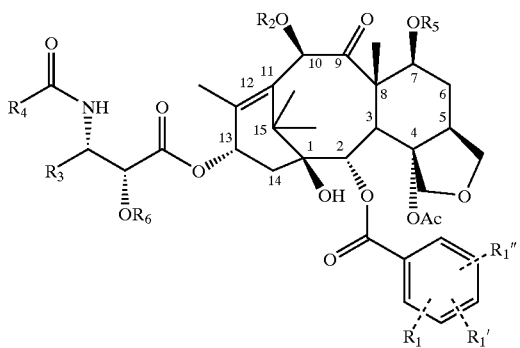

T1 wherein:
R$_1$ is H, an electron withdrawing group, or an electron donating group, and R$_1$' and R$_1$" are the same or different and are H, an electron withdrawing group, or an electron donating group;

R$_2$ is heterocyclic, a linear, branched, or cyclic ester or ether having from 1 to 10 carbon atoms or a carbamate of the formula —CONR$_{10}$R$_{11}$, wherein R$_{10}$ and R$_{11}$ are the same or different and are H, linear, branched or cyclic alkyl having 1 to 10 carbon atoms or aryl;

R$_3$ is an aryl, or a linear, branched, or cyclic alkyl having from 1 to 10 carbon atoms;

R$_4$ is —OC(CH$_3$)$_3$ or phenyl;

R$_5$ is a thiol moiety; and

R$_6$ is heterocyclic, H, a linear, branched, or cyclic ester or ether having from 1 to 10 carbon atoms or a carbamate of the formula —CONR$_{10}$R$_{11}$, wherein R$_{10}$ and R$_{11}$ are the same or different and are H, linear, branched or cyclic alkyl having 1 to 10 carbon atoms or aryl.

Also contemplated is the compound of the relevant examples above, wherein R$_1$ is F, NO$_2$, CN, Cl, CHF$_2$, CF$_3$, —OCH$_3$, OCH$_2$CH$_3$, or NR$_7$R$_8$, wherein:

R$_7$ and R$_8$ are the same or different and are linear, branched, or cyclic alkyl having 1 to 10 carbon atoms or simple or substituted aryl having 1 to 10 carbon atoms.

Also contemplated is the compound of the relevant examples above, wherein R$_7$ and R$_8$ each has 1 to 4 carbon atoms.

Also contemplated is the compound of the relevant examples above, wherein R$_7$ and R$_8$ are the same.

Also contemplated is the compound of the relevant examples above, wherein R$_7$ and R$_8$ are the same.

Also contemplated is the compound of the relevant examples above, wherein R$_2$ is —COC$_2$H$_5$, —CH$_2$CH$_3$, —CONHCH$_2$CH$_3$—CO-morpholino, —CO-piperidino, —CO-piperazino, or —CO-N-methylpiperazino.

Also contemplated is the compound of the relevant examples above, wherein R$_5$ is —(CH$_2$)$_n$S, —CO(CH$_2$)$_n$S, —(CH$_2$)$_n$CH(CH$_3$)S, —CO(CH$_2$)$_n$CH(CH$_3$)S, —(CH$_2$)$_n$C(CH$_3$)$_2$S, —CO(CH$_2$)$_n$C(CH$_3$)$_2$S, —CONR$_{12}$(CH$_2$)$_n$S, —CONR$_{12}$(CH$_2$)$_n$CH(CH$_3$)S, —CONR$_{12}$(CH$_2$)$_n$C(CH$_3$)$_2$S, —CO-morpholino-XS, —CO-piperidino-XS, —CO-piperazino-XS, or —CO-N-methylpiperazino-XS;

wherein n is an integer of 1 to 10; and wherein R$_{12}$ is H, a linear alkyl, branched alkyl or cyclic alkyl having 1 to 10 carbon atoms, or simple or substituted aryl having from 1 to 10 carbon atoms or heterocyclic.

Also contemplated is the compound of the relevant examples above, wherein R$_1$ is in the meta position when R$_1$' and R$_1$" are H or OCH$_3$.

Also contemplated is the compound of the relevant examples above, wherein R$_3$ is —CH=C(CH$_3$)$_2$.

Also contemplated is the cytotoxic agent according to the relevant examples above, wherein said thiol-containing taxane is a compound selected from the following formula T1:

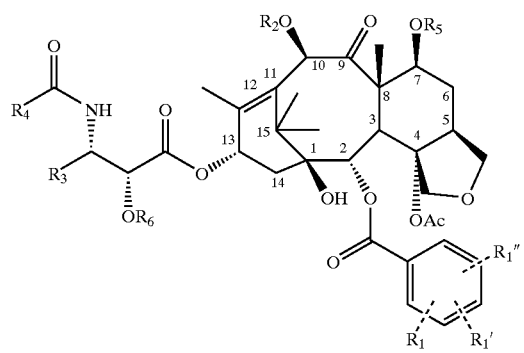

T1 wherein:
R$_1$ is H, an electron withdrawing group, or an electron donating group, and R$_1$' and R$_1$" are the same or different and are H, an electron withdrawing group, or an electron donating group;

R$_2$ is a thiol moiety;

R$_3$ is an aryl, or is a linear, branched, or cyclic alkyl having from 1 to 10 carbon atoms;

R$_4$ is —OC(CH$_3$)$_3$ or phenyl;

R$_5$ is heterocyclic, H, a linear, branched, or cyclic ester or ether having from 1 to 10 carbon atoms or a carbamate of the formula —CONR$_{10}$R$_{11}$, wherein R$_{10}$ and R$_{11}$ are the same or different and are H, linear, branched or cyclic alkyl having 1 to 10 carbon atoms or aryl; and R$_6$ is heterocyclic, H, a linear, branched, or cyclic ester or ether having from 1 to 10 carbon atoms or a carbamate of the formula —CONR$_{10}$R$_{11}$ wherein R$_{10}$ and R$_{11}$ are the same or different and are H, linear, branched or cyclic alkyl having 1 to 10 carbon atoms or aryl.

Also contemplated is the compound of the relevant examples above, wherein at least one of R$_1$ is F, NO$_2$, CN, Cl, CHF$_2$, CF$_3$, —OCH$_3$, —OCH$_2$CH$_3$, or NR$_7$R$_8$ wherein:

R$_7$ and R$_8$ are the same or different and are linear, branched, or cyclic alkyl having 1 to 10 carbon atoms or simple or substituted aryl having 1 to 10 carbon atoms.

Also contemplated is the compound of the relevant examples above, wherein R$_7$ and R$_8$ each has 1 to 4 carbon atoms.

Also contemplated is the compound of the relevant examples above, wherein R$_7$ and R$_8$ are the same.

Also contemplated is the compound of the relevant examples above, wherein R$_7$ and R$_8$ are the same.

Also contemplated is the compound of the relevant examples above, wherein R$_5$ is —(CH$_2$)$_n$S, —CO(CH$_2$)$_n$S, —(CH$_2$)$_n$CH(CH$_3$)S, —CO(CH$_2$)$_n$CH(CH$_3$)S, —(CH$_2$)$_n$C(CH$_3$)$_2$S, —CO(CH$_2$)$_n$C(CH$_3$)$_2$S, —CONR$_{12}$(CH$_2$)$_n$S, —CONR$_{12}$(CH$_2$)$_n$CH(CH$_3$)S, —CONR$_{12}$(CH$_2$)$_n$C(CH$_3$)$_2$S, —CO-morpholino-XS, —CO-piperidino-XS, —CO-piperazino-XS, or —CO-N-methylpiperazino-XS;

wherein n is an integer of 1 to 10; and wherein R$_{12}$ is H, a linear alkyl, branched alkyl or cyclic alkyl having 1 to 10 carbon atoms, or simple or substituted aryl having from 1 to 10 carbon atoms or heterocyclic.

Also contemplated is the compound of the relevant examples above, wherein $R_5$ is —$COC_2H_5$, —$CH_2CH_3$, —$CONHCH_2CH_3$, —CO-morpholino, —CO-piperidino, —CO-piperazino, or —CO-N-methylpiperazino.

Also contemplated is the compound of the relevant examples above, wherein $R_1$ is in the meta position when $R_1'$ and $R_1''$ are H or $OCH_3$.

Also contemplated is the cytotoxic agent according to the relevant examples above, wherein said thiol-containing taxane is a compound selected from the following formula T1:

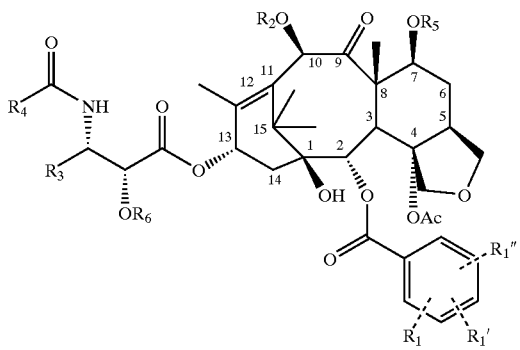

wherein:
- $R_1$ is H, an electron withdrawing group, or an electron donating group, and $R_1'$ and $R_1''$ are the same or different and are H, an electron withdrawing group, or an electron donating group;
- $R_2$ is heterocyclic, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl;
- $R_3$ is an aryl, or is a linear, branched or cyclic alkyl having from 1 to 10 carbon atoms;
- $R_4$ is —$OC(CH_3)_3$ or phenyl;
- $R_5$ is heterocyclic, H, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl;
- $R_6$ is a thiol moiety.

Also contemplated is the compound of the relevant examples above, wherein $R_1$ is F, $NO_2$, CN, Cl, $CHF_2$, $CF_3$, —$OCH_3$, —$OCH_2CH_3$, or $NR_7R_8$ wherein:
- $R_7$ and $R_8$ are the same or different and are linear, branched, or cyclic alkyl having 1 to 10 carbon atoms or simple or substituted aryl having 1 to 10 carbon atoms.

Also contemplated is the compound of the relevant examples above, wherein $R_7$ and $R_8$ each has 1 to 4 carbon atoms.

Also contemplated is the compound of the relevant examples above, wherein $R_7$ and $R_8$ are the same.

Also contemplated is the compound of the relevant examples above, wherein $R_7$ and $R_8$ are the same.

Also contemplated is the compound of the relevant examples above, wherein $R_2$ is —$COC_2H_5$, —$CH_2CH_3$, —$CONHCH_2CH_3$, —CO-morpholino, —CO-piperidino, —CO-piperazino, or —CO-N-methylpiperazino.

Also contemplated is the compound of the relevant examples above, wherein $R_5$ is —$(CH_2)_nS$, —$CO(CH_2)_nS$, —$(CH_2)_nCH(CH_3)S$, —$CO(CH_2)_nCH(CH_3)S$, —$(CH_2)_nC(CH_3)_2S$, —$CO(CH_2)_nC(CH_3)_2S$, —$CONR_{12}(CH_2)_nS$, —$CONR_{12}(CH_2)_nCH(CH_3)S$, —$CONR_{12}(CH_2)_nC(CH_3)_2S$, —CO-morpholino-XS, —CO-piperidino-XS, —CO-piperazino-XS, or —CO-N-methylpiperazino-XS;
wherein n is an integer of 1 to 10; and
wherein $R_{12}$ is H, a linear alkyl, branched alkyl or cyclic alkyl having 1 to 10 carbon atoms, or simple or substituted aryl having from 1 to 10 carbon atoms or heterocyclic.

Also contemplated is the compound of the relevant examples above, wherein $R_1$ is in the meta position when $R_1'$ and $R_1''$ are H or $OCH_3$.

Also contemplated is the cytotoxic agent according to the relevant examples above, wherein said thiol-containing CC-1065 analogue is a cyclopropylbenzindole-containing cytotoxic compound formed from an A subunit of the formulae A-3 or A-4 covalently linked to either a B subunit of the formula F-1 or a B-C subunit of the formulae F-3 or F-7 via an amide bond from the secondary amino group of the pyrrole moiety of the A subunit to the C-2 carboxyl group of the B subunit, wherein the formulae A-3 and A-4 are as follows:

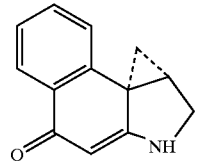

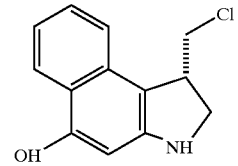

wherein the formulae F-1, F-3 and F-7 are as follows:

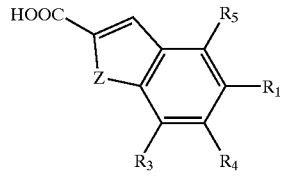

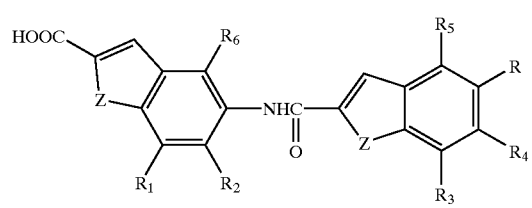

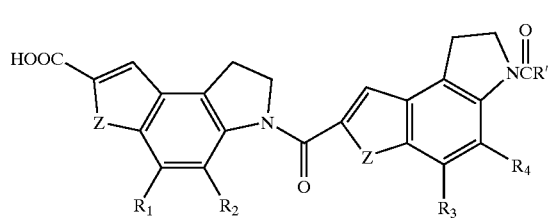

wherein each Z may be the same or different and may be O or NH; and wherein, in Formula F-1 $R_4$ is a thiol moiety, in Formula F-3 one of R or $R_4$ is a thiol moiety, in Formula F-7 one of R' or $R_4$ is a thiol moiety; when R or R' is a thiol moiety, then $R_1$ to $R_6$, which may be the same or different, are hydrogen, $C_1$–$C_3$ linear alkyl, methoxy, hydroxyl, primary amino, secondary amino, tertiary amino, or amido; and when $R_4$ is a thiol moiety, R, $R_1$, $R_2$, $R_3$, $R_4$, $R_5$ and $R_6$, which may be the same or different, are hydrogen, $C_1$–$C_3$ linear alkyl, methoxy, hydroxyl, primary amino, secondary amino, tertiary amino, or amido, and R' is $NH_2$, alkyl, O-alkyl, primary amino, secondary amino, tertiary amino, or amido.

Also contemplated is the cytotoxic agent of the relevant examples above, wherein R and R' are thiol moieties and $R_1$ to $R_6$ are each hydrogen.

Also contemplated is the cytotoxic agent of the relevant examples above, wherein R or $R_4$ is $NHCO(CH_2)_l S$, $NHCOC_6H_4(CH_2)_l S$, or $O(CH_2)_l S$, and R' is $(CH_2)_l S$, $NH(CH_2)_l S$ or $O(CH_2)_l S$ wherein:

l is an integer of 1 to 10.

Also contemplated is the cytotoxic agent of the relevant examples above, wherein R or $R_4$ is $NHCO(CH_2)_n S$, $NHCOC_6H_4(CH_2)_l S$, or $O(CH_2)_l S$, and R' is $(CH_2)_l S$, $NH(CH_2)_l S$ or $O(CH_2)_l S$ wherein:

l is an integer of 1 to 10.

Also contemplated is the cytotoxic agent of the relevant examples above, wherein l is 1.

Also contemplated is the cytotoxic agent of the relevant examples above, wherein l is 2.

Also contemplated is the cytotoxic agent according to the relevant examples above, wherein said thiol-containing doxorubicin analogue is a compound selected from the following formula D2:

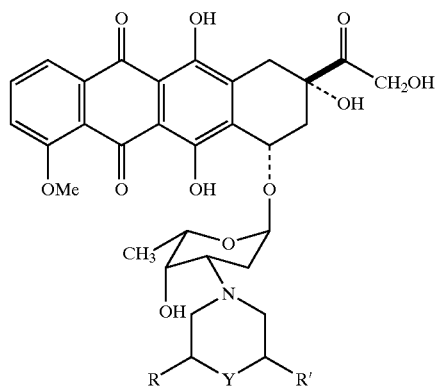

wherein,

Y is O or $NR_2$, wherein $R_2$ is linear or branched alkyl having 1 to 5 carbon atoms;

R is a thiol moiety, H, or liner or branched alkyl having 1 to 5 carbon atoms; and R' is a thiol moiety, H, or —$OR_1$, wherein $R_1$ is linear or branched alkyl having 1 to 5 carbon atoms;

provided that R and R' are not thiol moieties at the same time.

Also contemplated is the compound of the relevant examples above, wherein $NR_2$ is $NCH_3$.

Also contemplated is the compound of the relevant examples above, wherein R' is —O.

Also contemplated is the compound of the relevant examples above, wherein the thiol moiety is —$(CH_2)_n S$, —$O(CH_2)_n S$, —$(CH_2)_n CH(CH_3)S$, —$O(CH_2)_n CH(CH_3)S$, —$(CH_2)_n C(CH_3)_2 S$, or —$O(CH_2)_n C(CH_3)_2 S$, wherein n is an integer of 1 to 10.

Also contemplated is the cytotoxic agent according to the relevant examples above, wherein said thiol-containing daunorubicin analogue is a compound selected from the following formula D3:

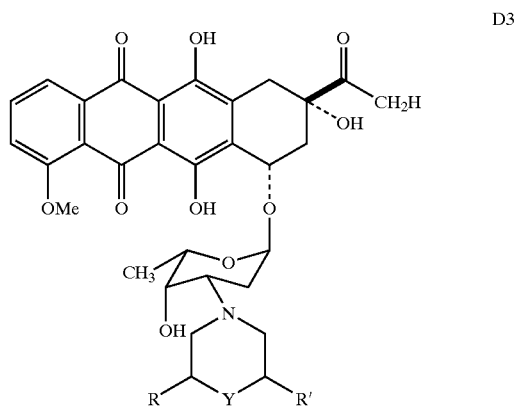

wherein,

Y is O or $NR_2$, wherein $R_2$ is linear or branched alkyl having 1 to 5 carbon atoms;

R is a thiol moiety, H, or liner or branched alkyl having 1 to 5 carbon atoms; and R' is a thiol moiety, H, or —$OR_1$, wherein $R_1$ is linear or branched alkyl having 1 to 5 carbon atoms;

provided that R and R' are not thiol moieties at the same time.

Also contemplated is the compound of the relevant examples above, wherein $NR_2$ is $NCH_3$.

Also contemplated is the compound of the relevant examples above, wherein R' is —O.

Also contemplated is the compound of the relevant examples above, wherein the thiol moiety is —$(CH_2)_n S$, —$O(CH_2)_n S$, —$(CH_2)_n CH(CH_3)S$, —$O(CH_2)_n CH(CH_3)S$, —$(CH_2)_n C(CH_3)_2 S$, or —$O(CH_2)_n C(CH_3)_2 S$, wherein n is an integer of 1 to 10.

In a second embodiment of the invention, a cytotoxic conjugate comprising one or more cytotoxic agents linked to a cell-binding agent through a PEG linking group is disclosed. The cell-binding agents contemplated in this, and each proceeding embodiment, include antibodies (especially monoclonal antibodies and antibody fragments), interferons, lymphokines, hormones, growth factors, vitamins, and nutrient-transport molecules (such as transferrin).

In a preferred embodiment, the PEG linking group has from 1 to 20 monomeric units. In an equally preferred embodiment, the PEG linking group has from 21 to 40 monomeric units. In a further equally preferred embodiment, the PEG linking group has from 41 to 1000 monomeric units.

Specifically contemplated is a cytotoxic conjugate, comprising one or more cytotoxic agents covalently bonded to a cell-binding agent through a PEG linking group having 1 to 20 monomeric units, wherein a linkage of one of said one or more cytotoxic agents is illustrated in formula 3:

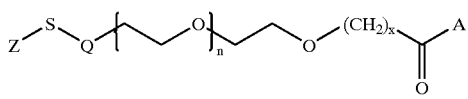

wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl,
wherein n is an integer of from 0 to 20;
wherein x is 1 or 2; and
wherein A is said cell-binding agent.

Also contemplated is a cytotoxic conjugate, comprising one or more cytotoxic agents covalently bonded to a cell-binding agent through a PEG linking group having 21 to 40 monomeric units, wherein a linkage of one of said one or more cytotoxic agents is illustrated in a formula 3:

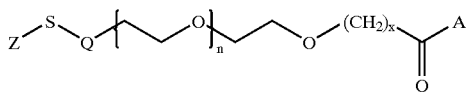

wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl,
wherein n is an integer of from 21 to 40;
wherein x is 1 or 2; and
wherein A is said cell-binding agent.

Also contemplated is a cytotoxic conjugate, comprising one or more cytotoxic agents covalently bonded to a cell-binding agent through a PEG linking group having 41 to 1000 monomeric units, wherein a linkage of one of said one or more cytotoxic agents is illustrated in formula 3:

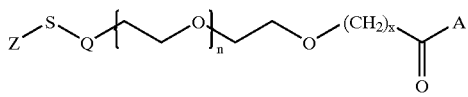

wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl,
wherein n is an integer of from 41 to 1000;
wherein x is 1 or 2; and
wherein A is said cell-binding agent.

Also contemplated is the cytotoxic conjugate according to any one of the relevant examples above, wherein said cytotoxic agent is selected from the group consisting of an thiol-containing maytansinoid, thiol-containing taxane, thiol-containing CC-1065 analogue, thiol-containing daunorubicin analogue and thiol-containing doxorubicin analogue, and thiol-containing analogues or derivatives thereof, and said cell-binding agent is selected from the group consisting of a polyclonal antibody, monoclonal antibody, antibody fragment, interferon, lymphokine, hormone, growth factor, vitamin and nutrient-transport molecule.

Also contemplated is the cytotoxic conjugate according to the relevant examples above, wherein said thiol-containing maytansinoid is a C-3 thiol-containing maytansinoid.

Also contemplated is the cytotoxic conjugate according to the relevant examples above, wherein said C-3 thiol-containing maytansinoid is an N-methyl-alanine-containing C-3 thiol-containing maytansinoid.

Also contemplated is the cytotoxic conjugate according to the relevant examples above, wherein said N-methyl-alanine-containing C-3 thiol-containing maytansinoid is a compound selected from the following formula M1:

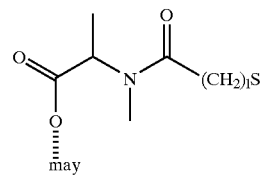

wherein:
l is an integer of from 1 to 10; and
may is a maytansinoid.

Also contemplated is the cytotoxic conjugate according to the relevant examples above, wherein said N-methyl-alanine-containing C-3 thiol-containing maytansinoid is a compound selected from the following formula M2:

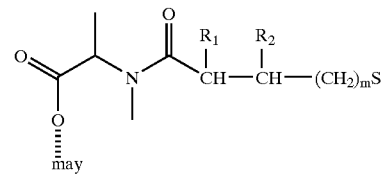

wherein:
$R_1$ and $R_2$ are H, $CH_3$ or $CH_2CH_3$, and may be the same or different;
m is 0, 1, 2 or 3; and
may is a maytansinoid.

Also contemplated is the cytotoxic conjugate according to the relevant examples above, wherein said N-methyl-alanine-containing C-3 thiol-containing maytansinoid is a compound selected from the following formula M3:

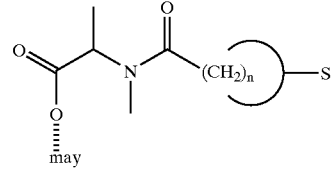

wherein:
n is an integer of from 3 to 8; and
may is a maytansinoid.

Also contemplated is the cytotoxic conjugate according to the relevant examples above, wherein said N-methyl-alanine-containing C-3 thiol-containing maytansinoid is a N-methyl-alanine-containing C-3 thiol-containing maytansinol.

Also contemplated is the cytotoxic conjugate according to the relevant examples above, wherein said N-methyl-alanine-containing C-3 thiol-containing maytansinol is a dechloro maytansinol.

Also contemplated is the cytotoxic conjugate according to the relevant examples above, wherein said N-methyl-alanine-containing C-3 thiol-containing maytansinol is a compound selected from the following formula M6:

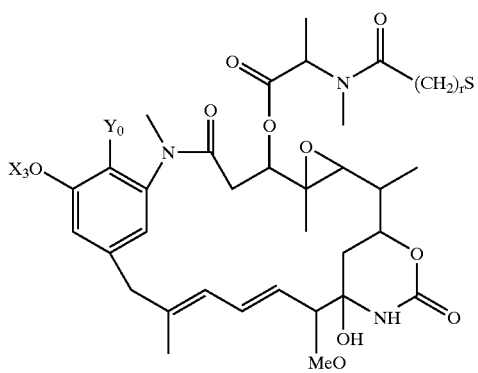

M6 wherein:
l is 1, 2 or 3;
$Y_0$ is Cl or H; and
$X_3$ is H or $CH_3$.

Also contemplated is the cytotoxic conjugate according to the relevant examples above, wherein said C-3 thiol-containing maytansinoid is an N-methyl-cysteine-containing C-3 thiol-containing maytansinoid.

Also contemplated is the cytotoxic conjugate according to the relevant examples above, wherein said N-methyl-cysteine-containing C-3 thiol-containing maytansinoid is a compound selected from the following formula M4:

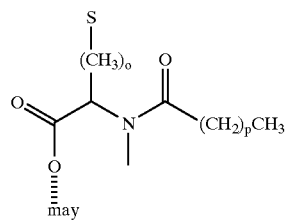

M4 wherein:
o is 1, 2 or 3;
p is an integer of 0 to 10; and
may is a maytansinoid.

Also contemplated is the cytotoxic conjugate according to the relevant examples above, wherein said N-methyl-cysteine-containing C-3 thiol-containing maytansinoid is a N-methyl-cysteine-containing C-3 thiol-containing maytansinol.

Also contemplated is the cytotoxic conjugate according to the relevant examples above, wherein said N-methyl-cysteine-containing C-3 thiol-containing maytansinol is a dechloro maytansinol.

Also contemplated is the cytotoxic conjugate according to the relevant examples above, wherein said N-methyl-cysteine-containing C-3 thiol-containing maytansinol is a compound selected from the following formula M5:

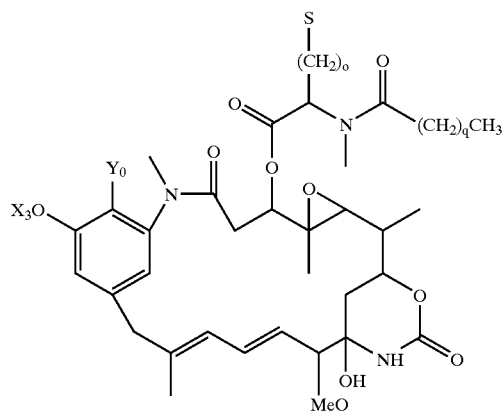

M5 wherein:
o is 1, 2 or 3;
q is an integer of from 0 to 10;
$Y_0$ is Cl or H; and
$X_3$ is H or $CH_3$.

Also contemplated is the cytotoxic conjugate according to the relevant examples above, wherein said thiol-containing taxane is a compound selected from the following formula T1:

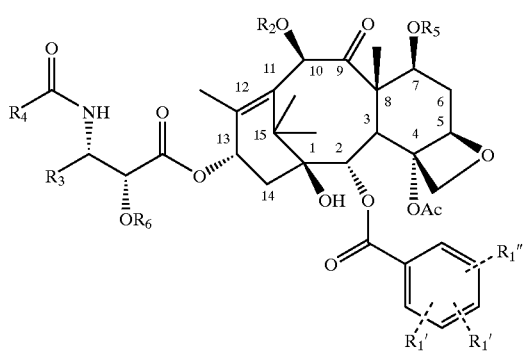

T1 wherein:
$R_1$ is H, an electron withdrawing group, or an electron donating group, and $R_1'$ and $R_1''$ are the same or different and are H, an electron withdrawing group, or an electron donating group;

$R_2$ is heterocyclic, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl;

$R_3$ is an aryl, or a linear, branched, or cyclic alkyl having from 1 to 10 carbon atoms;

$R_4$ is —$OC(CH_3)_3$ or phenyl;

$R_5$ is a thiol moiety; and $R_6$ is heterocyclic, H, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl.

Also contemplated is the compound of the relevant examples above, wherein $R_1$ is F, $NO_2$, CN, Cl, $CHF_2$, $CF_3$, —$OCH_3$, —$OCH_2CH_3$, or $NR_7R_8$, wherein:

$R_7$ and $R_8$ are the same or different and are linear, branched, or cyclic alkyl having 1 to 10 carbon atoms or simple or substituted aryl having 1 to 10 carbon atoms.

Also contemplated is the compound of the relevant examples above, wherein $R_7$ and $R_8$ each has 1 to 4 carbon atoms.

Also contemplated is the compound of the relevant examples above, wherein $R_7$ and $R_8$ are the same.

Also contemplated is the compound of the relevant examples above, wherein $R_7$ and $R_8$ are the same.

Also contemplated is the compound of the relevant examples above, wherein $R_2$ is —$COC_2H_5$, —$CH_2CH_3$, —$CONHCH_2CH_3$—CO-morpholino, —CO-piperidino, —CO-piperazino, or —CO-N-methylpiperazino.

Also contemplated is the compound of the relevant examples above, wherein $R_5$ is —$(CH_2)_nS$, —$CO(CH_2)_nS$, —$(CH_2)_nCH(CH_3)S$, —$CO(CH_2)_nCH(CH_3)S$, —$(CH_2)_nC(CH_3)_2S$, —$CO(CH_2)_nC(CH_3)_2S$, —$CONR_{12}(CH_2)_nS$, —$CONR_{12}(CH_2)_nCH(CH_3)S$, —$CONR_{12}(CH_2)_nC(CH_3)_2S$, —CO-morpholino-XS, —CO-piperidino-XS, —CO-piperazino-XS, or —CO-N-methylpiperazino-XS;

wherein n is an integer of 1 to 10; and wherein $R_{12}$ is H, a linear alkyl, branched alkyl or cyclic alkyl having 1 to 10 carbon atoms, or simple or substituted aryl having from 1 to 10 carbon atoms or heterocyclic.

Also contemplated is the compound of the relevant examples above, wherein $R_1$ is in the meta position when $R_1'$ and $R_1''$ are H or $OCH_3$.

Also contemplated is the compound of the relevant examples above, wherein $R_3$ is —CH=C(CH$_3$)$_2$.

Also contemplated is the cytotoxic conjugate according to the relevant examples above, wherein said thiol-containing taxane is a compound selected from the following formula T1:

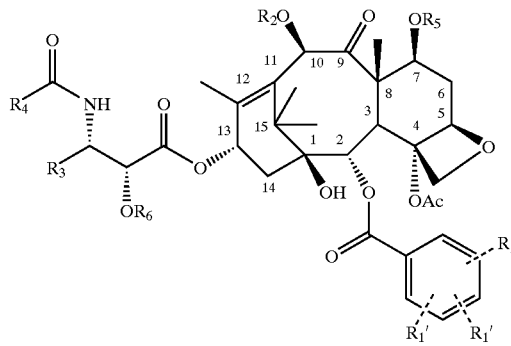

wherein:
$R_1$ is H, an electron withdrawing group, or an electron donating group, and $R_1'$ and $R_1''$ are the same or different and are H, an electron withdrawing group, or an electron donating group;
$R_2$ is a thiol moiety;
$R_3$ is aryl, or is a linear, branched, or cyclic alkyl having from 1 to 10 carbon atoms;
$R_4$ is —$OC(CH_3)_3$ or phenyl;
$R_5$ is heterocyclic, H, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl; and $R_6$ is heterocyclic, H, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl.

Also contemplated is the compound of the relevant examples above, wherein at least one of $R_1$ is F, $NO_2$, CN, Cl, $CHF_2$, $CF_3$, —$OCH_3$, —$OCH_2CH_3$, or $NR_7R_8$ wherein:

$R_7$ and $R_8$ are the same or different and are linear, branched, or cyclic alkyl having 1 to 10 carbon atoms or simple or substituted aryl having 1 to 10 carbon atoms.

Also contemplated is the compound of the relevant examples above, wherein $R_7$ and $R_8$ each has 1 to 4 carbon atoms.

Also contemplated is the compound of the relevant examples above, wherein $R_7$ and $R_8$ are the same.

Also contemplated is the compound of the relevant examples above, wherein $R_7$ and $R_8$ are the same.

Also contemplated is the compound of the relevant examples above, wherein $R_5$ is —$(CH_2)_nS$, —$CO(CH_2)_nS$, —$(CH_2)_nCH(CH_3)S$, —$CO(CH_2)_nCH(CH_3)S$, —$(CH_2)_nC(CH_3)_2S$, —$CO(CH_2)_nC(CH_3)_2S$, —$CONR_{12}(CH_2)_nS$, —$CONR_{12}(CH_2)_nCH(CH_3)S$, —$CONR_{12}(CH_2)_nC(CH_3)_2S$, —CO-morpholino-XS, —CO-piperidino-XS, —CO-piperazino-XS, or —CO-N-methylpiperazino-XS;

wherein n is an integer of 1 to 10; and wherein $R_{12}$ is H, a linear alkyl, branched alkyl or cyclic alkyl having 1 to 10 carbon atoms, or simple or substituted aryl having from 1 to 10 carbon atoms or heterocyclic.

Also contemplated is the compound of the relevant examples above, wherein $R_5$ is —$COC_2H_5$, —$CH_2CH_3$, —$CONHCH_2CH_3$, —CO-morpholino, —CO-piperidino, —CO-piperazino, or —CO-N-methylpiperazino.

Also contemplated is the compound of the relevant examples above, wherein $R_1$ is in the meta position when $R_1'$ and $R_1''$ are H or $OCH_3$.

Also contemplated is the cytotoxic conjugate according to the relevant examples above, wherein said thiol-containing taxane is a compound selected from the following formula T1:

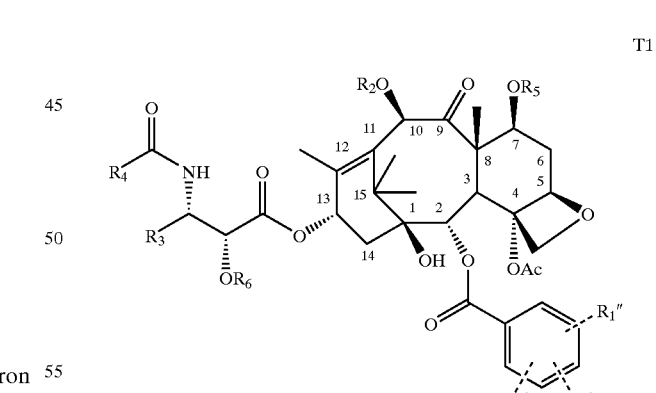

wherein:
$R_1$ is H, an electron withdrawing group, or an electron donating group, and $R_1'$ and $R_1''$ are the same or different and are H, an electron withdrawing group, or an electron donating group;
$R_2$ is heterocyclic, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl;

R₃ is aryl, or is a linear, branched or cyclic alkyl having from 1 to 10 carbon atoms;

R₄ is —OC(CH₃)₃ or phenyl;

R₅ is heterocyclic, H, a linear, branched, or cyclic ester or ether having from 1 to 10 carbon atoms or a carbamate of the formula —CONR₁₀R₁₁, wherein R₁₀ and R₁₁ are the same or different and are H, linear, branched or cyclic alkyl having 1 to 10 carbon atoms or aryl;

R₆ is a thiol moiety.

Also contemplated is the compound of the relevant examples above, wherein R₁ is F, NO₂, CN, Cl, CHF₂, CF₃, —OCH₃, —OCH₂CH₃, or NR₇R₈ wherein:

R₇ and R₈ are the same or different and are linear, branched, or cyclic alkyl having 1 to 10 carbon atoms or simple or substituted aryl having 1 to 10 carbon atoms.

Also contemplated is the compound of the relevant examples above, wherein R₇ and R₈ each has 1 to 4 carbon atoms.

Also contemplated is the compound of the relevant examples above, wherein R₇ and R₈ are the same.

Also contemplated is the compound of the relevant examples above, wherein R₇ and R₈ are the same.

Also contemplated is the compound of the relevant examples above, wherein R₂ is —COC₂H₅, —CH₂CH₃, —CONHCH₂CH₃, —CO-morpholino, —CO-piperidino, —CO-piperazino, or —CO-N-methylpiperazino.

Also contemplated is the compound of the relevant examples above, wherein R₅ is —(CH₂)ₙS, —CO(CH₂)ₙS, —(CH₂)ₙCH(CH₃)S, —CO(CH₂)ₙCH(CH₃)S, —(CH₂)ₙC(CH₃)₂S, —CO(CH₂)ₙC(CH₃)₂S, —CONR₁₂(CH₂)ₙS, —CONR₁₂(CH₂)ₙCH(CH₃)S, —CONR₁₂(CH₂)ₙC(CH₃)₂S, —CO-morpholino-XS, —CO-piperidino-XS, —CO-piperazino-XS, or —CO-N-methylpiperazino-XS;

wherein n is an integer of 1 to 10; and wherein R₁₂ is H, a linear alkyl, branched alkyl or cyclic alkyl having 1 to 10 carbon atoms, or simple or substituted aryl having from 1 to 10 carbon atoms or heterocyclic.

Also contemplated is the compound of the relevant examples above, wherein R₁ is in the meta position when R₁' and R₁" are H or OCH₃.

Also contemplated is the cytotoxic conjugate according to the relevant examples above, wherein said thiol-containing CC-1065 analogue is a cyclopropylbenzindole-containing cytotoxic compound formed from an A subunit of the formulae A-3 or A-4 covalently linked to either a B subunit of the formula F-1 or a B-C subunit of the formulae F-3 or F-7 via an amide bond from the secondary amino group of the pyrrole moiety of the A subunit to the C-2 carboxyl group of the B subunit, wherein the formulae A-3 and A-4 are as follows:

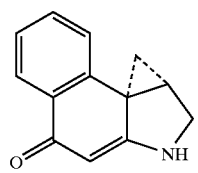
A-3

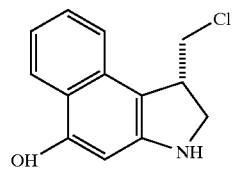
A-4 wherein the formulae F-1, F-3 and F-7 are as follows:

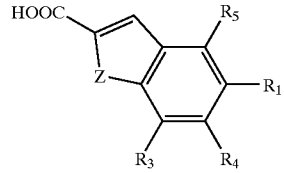
F-1

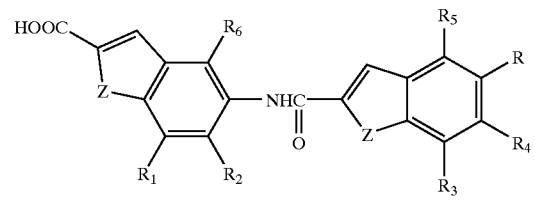
F-3

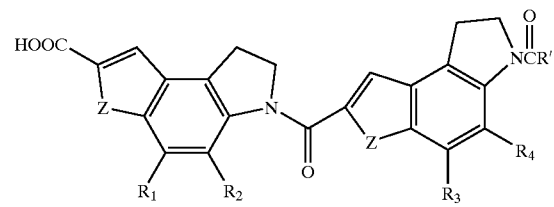
F-7 wherein each Z may be the same or different and may be O or NH; and wherein, in Formula F-1 R₄ is a thiol moiety, in Formula F-3 one of R or R₄ is a thiol moiety, in Formula F-7 one of R' or R₄ is a thiol moiety; when R or R' is a thiol moiety, then R₁ to R₆, which may be the same or different, are hydrogen, C₁-C₃ linear alkyl, methoxy, hydroxyl, primary amino, secondary amino, tertiary amino, or amido; and when R₄ is a thiol moiety, R, R₁, R₂, R₃, R₄, R₅ and R₆, which may be the same or different, are hydrogen, C₁-C₃ linear alkyl, methoxy, hydroxyl, primary amino, secondary amino, tertiary amino, or amido, and R' is NH₂, alkyl, O-alkyl, primary amino, secondary amino, tertiary amino, or amido.

Also contemplated is the cytotoxic conjugate of the relevant examples above, wherein R and R' are thiol moieties and R₁ to R₆ are each hydrogen.

Also contemplated is the cytotoxic conjugate of the relevant examples above, wherein R or R₄ is —NHCO(CH₂)ₗS, —NHCOC₆H₄(CH₂)ₗS, or —O(CH₂)ₗS, and R' is —(CH₂)ₗS, —NH(CH₂)ₗS or —O(CH₂)ₗS wherein:

l is an integer of 1 to 10.

Also contemplated is the cytotoxic conjugate of the relevant examples above, wherein R or R₄ is —NHCO(CH₂)ₗS, —NHCOC₆H₄(CH₂)ₗS, or —O(CH₂)ₗS, and R' is —(CH₂)ₗS, —NH(CH₂)ₗS or —O(CH₂)ₗS wherein:

l is an integer of 1 to 10.

Also contemplated is the cytotoxic conjugate of the relevant examples above, wherein l is 1.

Also contemplated is the cytotoxic conjugate of the relevant examples above, wherein l is 2.

Also contemplated is the cytotoxic conjugate according to the relevant examples above, wherein said thiol-containing doxorubicin analogue is a compound selected from the following formula D2:

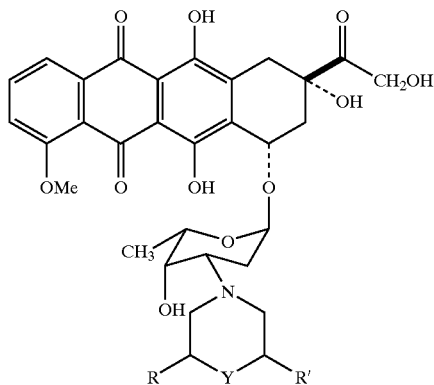

D2 wherein,

Y is O or $NR_2$, wherein $R_2$ is linear or branched alkyl having 1 to 5 carbon atoms;

R is a thiol moiety, H, or liner or branched alkyl having 1 to 5 carbon atoms; and R' is a thiol moiety, H, or —$OR_1$, wherein $R_1$ is linear or branched alkyl having 1 to 5 carbon atoms;

provided that R and R' are not thiol moieties at the same time.

Also contemplated is the compound of the relevant examples above, wherein $NR_2$ is $NCH_3$.

Also contemplated is the compound of the relevant examples above, wherein R' is —O.

Also contemplated is the compound of the relevant examples above, wherein the thiol moiety is —$(CH_2)_nS$, —$O(CH_2)_nS$, —$(CH_2)_nCH(CH_3)S$, —$O(CH_2)_nCH(CH_3)S$, —$(CH_2)_nC(CH_3)_2S$, or —$O(CH_2)_nC(CH_3)_2S$, wherein n is an integer of 1 to 10.

Also contemplated is the cytotoxic conjugate according to the relevant examples above, wherein said thiol-containing daunorubicin analogue is a compound selected from the following

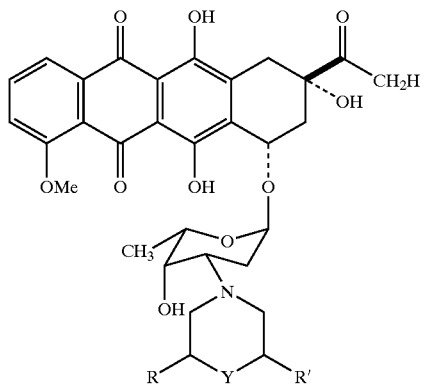

D3 wherein,

Y is O or $NR_2$, wherein $R_2$ is linear or branched alkyl having 1 to 5 carbon atoms;

R is a thiol moiety, H, or liner or branched alkyl having 1 to 5 carbon atoms; and R' is a thiol moiety, H, or —$OR_1$, wherein $R_1$ is linear or branched alkyl having 1 to 5 carbon atoms;

provided that R and R' are not thiol moieties at the same time.

Also contemplated is the compound of the relevant examples above, wherein $NR_2$ is $NCH_3$.

Also contemplated is the compound of the relevant examples above, wherein R' is —O.

Also contemplated is the compound of the relevant examples above, wherein the thiol moiety is —$(CH_2)_nS$, —$O(CH_2)_nS$, —$(CH_2)_nCH(CH_3)S$, —$O(CH_2)_nCH(CH_3)S$, —$(CH_2)_nC(CH_3)_2S$, or —$O(CH_2)_nC(CH_3)_2S$, wherein n is an integer of 1 to 10.

Also contemplated is the cytotoxic conjugate according to the relevant examples above, wherein said cell-binding agent is a monoclonal antibody.

Also contemplated is the cytotoxic conjugate according to the relevant examples above, wherein said cell-binding agent is an antibody fragment.

Also contemplated is the cytotoxic conjugate according to the relevant examples above, wherein said cytotoxic agent is a taxane and said cell-binding agent is a monoclonal antibody.

In a third embodiment of the invention, a therapeutic composition comprising a therapeutically-effective amount of one of the cytotoxic conjugates of the present invention, and a pharmaceutically-acceptable carrier, is disclosed.

Specifically contemplated is a therapeutic composition comprising a therapeutically-effective amount of the cytotoxic conjugate of the relevant examples above, and a pharmaceutically acceptable carrier.

Also contemplated is the therapeutic composition according to the relevant examples above, wherein the therapeutically-effective amount of the cytotoxic conjugate is from 10 ug to 100 mg.

Also contemplated is the therapeutic composition according to the relevant examples above, wherein the therapeutically-effective amount of the cytotoxic conjugate is from 50 ug to 30 mg.

Also contemplated is the therapeutic composition according to the relevant examples above, wherein the therapeutically-effective amount of the cytotoxic conjugate is from 1 mg to 20 mg.

In a fourth embodiment of the invention, a method for producing a cytotoxic agent bearing a PEG linking group having a terminal active ester is disclosed. The method comprises a) reacting a PEG linking group through a disulfide group with a thiol-containing cytotoxic agent, and b) converting the terminal carboxylic acid group or protective chemical group of the product of step a) to an active ester, thereby producing a cytotoxic agent bearing a PEG linking group having a terminal active ester.

In a preferred embodiment, the PEG linking group has from 1 to 20 monomeric units. In an equally preferred embodiment, the PEG linking group has from 21 to 40 monomeric units. In a further equally preferred embodiment, the PEG linking group has from 41 to 1000 monomeric units.

Specifically contemplated is a method for producing a cytotoxic agent, bearing a PEG linking group having a terminal active ester and 1 to 20 monomeric units, of formula 2:

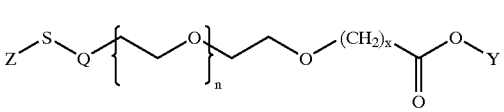

2 wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 0 to 20;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl,
said method comprising the steps of:
a) reacting a PEG linking group having 1 to 20 monomeric units of formula 1:

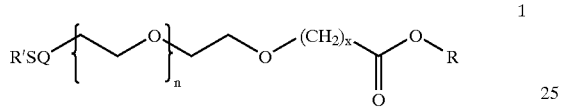

wherein R' is 2-pyridyl, 4-pyridyl, 5-nitro-2-pyridyl, 5-nitro-4-pyridyl, 2-nitrophenyl, 4-nitrophenyl or 2,4-dinitrophenyl;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 0 to 20;
wherein x is 1 or 2; and
wherein R is H, a cation to form a salt or a chemical group to form an ester, with a thiol-containing cytotoxic agent, and
b) converting the R group of the product of step a) to an active ester, thereby producing a cytotoxic agent bearing a PEG linking group having a terminal active ester and 1 to 20 monomeric units.
Also contemplated is a method for producing a cytotoxic agent, bearing a PEG linking group having a terminal active ester and 21 to 40 monomeric units, of formula 2:

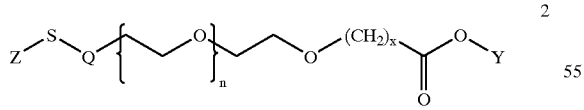

wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 21 to 40;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl,
said method comprising the steps of:
a) reacting a PEG linking group having 21 to 40 monomeric units of formula 1:

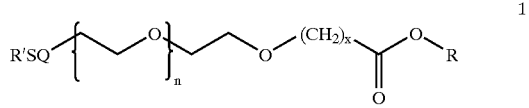

wherein R' is 2-pyridyl, 4-pyridyl, 5-nitro-2-pyridyl, 5-nitro-4-pyridyl, 2-nitrophenyl, 4-nitrophenyl or 2,4-dinitrophenyl;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 21 to 40;
wherein x is 1 or 2; and
wherein R is H, a cation to form a salt or a chemical group to form an ester, with a thiol-containing cytotoxic agent, and
b) converting the R group of the product of step a) to an active ester, thereby producing a cytotoxic agent bearing a PEG linking group having a terminal active ester and 21 to 40 monomeric units.
Also contemplated is a method for producing a cytotoxic agent, bearing a PEG linking group having a terminal active ester and 41 to 1000 monomeric units, of formula 2:

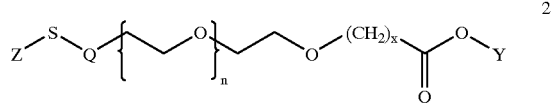

wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 41 to 1000;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl, said method comprising the steps of:
a) reacting a PEG linking group having 41 to 1000 monomeric units of formula 1:

$$R'SQ\left\{\begin{array}{c}O\\\end{array}\right\}_n O-(CH_2)_x \begin{array}{c}O\\\parallel\\O\end{array} O-R \quad 1$$

wherein R' is 2-pyridyl, 4-pyridyl, 5-nitro-2-pyridyl, 5-nitro-4-pyridyl, 2-nitrophenyl, 4-nitrophenyl or 2,4-dinitrophenyl;
wherein Q is $R_2COO—$, $R_2R_3NCOO—$, $R_2OCOO—$, $R_2O—$, $R_2CONR_3—$, $R_2R_3N—$, $R_2OCONR_3—$, or S—,
wherein:
$R_2$ is $SCR_4R_5R_6—$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is an integer of from 41 to 1000;
wherein x is 1 or 2; and
wherein R is H, a cation to form a salt or a chemical group to form an ester, with a thiol-containing cytotoxic agent, and
b) converting the R group of the product of step a) to an active ester, thereby producing a cytotoxic agent bearing a PEG linking group having a terminal active ester and 41 to 1000 monomeric units.

Also contemplated is the method for producing a cytotoxic agent, bearing a PEG linking group having a terminal active ester, according to anyone of the relevant examples above, wherein the chemical group is methyl, ethyl, phenyl, benzyl or tertbutyl.

Also contemplated is the method for producing a cytotoxic agent, bearing a PEG linking group having a terminal active ester, according to any one of the relevant examples above, wherein said cytotoxic agent is selected from the group consisting of an thiol-containing maytansinoid, thiol-containing taxane, thiol-containing CC-1065 analogue, thiol-containing daunorubicin analogue and thiol-containing doxorubicin analogue, and thiol-containing analogues or derivatives thereof.

Also contemplated is the method according to the relevant examples above, wherein said thiol-containing maytansinoid is a C-3 thiol-containing maytansinoid.

Also contemplated is the method according to the relevant examples above, wherein said C-3 thiol-containing maytansinoid is an N-methyl-alanine-containing C-3 thiol-containing maytansinoid.

Also contemplated is the method according to the relevant examples above, wherein said N-methyl-alanine-containing C-3 thiol-containing maytansinoid is a compound selected from the following formula M1:

M1 wherein:
l is an integer of from 1 to 10; and
may is a maytansinoid.

Also contemplated is the method according to the relevant examples above, wherein said N-methyl-alanine-containing C-3 thiol-containing maytansinoid is a compound selected from the following formula M2:

M2 wherein:
$R_1$ and $R_2$ are H, $CH_3$ or $CH_2CH_3$, and may be the same or different;
m is 0, 1, 2 or 3; and
may is a maytansinoid.

Also contemplated is the method according to the relevant examples above, wherein said N-methyl-alanine-containing C-3 thiol-containing maytansinoid is a compound selected from the following formula M3:

M3 wherein:
n is an integer of from 3 to 8; and
may is a maytansinoid.

Also contemplated is the method according to the relevant examples above, wherein said N-methyl-alanine-containing C-3 thiol-containing maytansinoid is a N-methyl-alanine-containing C-3 thiol-containing maytansinol.

Also contemplated is the method according to the relevant examples above, wherein said N-methyl-alanine-containing C-3 thiol-containing maytansinol is a dechloro maytansinol.

Also contemplated is the method according to the relevant examples above, wherein said N-methyl-alanine-containing C-3 thiol-containing maytansinol is a compound selected from the following formula M6:

M6 wherein:
l is 1, 2 or 3;
$Y_0$ is Cl or H; and
$X_3$ is H or $CH_3$.

Also contemplated is the method according to the relevant examples above, wherein said C-3 thiol-containing maytansinoid is an N-methyl-cysteine-containing C-3 thiol-containing maytansinoid.

Also contemplated is the method according to the relevant examples above, wherein said N-methyl-cysteine-containing C-3 thiol-containing maytansinoid is a compound selected from the following formula M4:

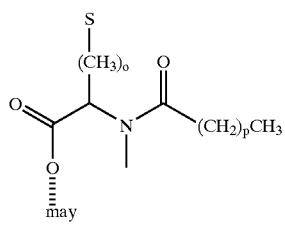

M4 wherein:

o is 1, 2 or 3;

p is an integer of 0 to 10; and may is a maytansinoid.

Also contemplated is the method according to the relevant examples above, wherein said N-methyl-cysteine-containing C-3 thiol-containing maytansinoid is a N-methyl-cysteine-containing C-3 thiol-containing maytansinol.

Also contemplated is the method according to the relevant examples above, wherein said N-methyl-cysteine-containing C-3 thiol-containing maytansinol is a dechloro maytansinol.

Also contemplated is the method according to the relevant examples above, wherein said N-methyl-cysteine-containing C-3 thiol-containing maytansinol is a compound selected from the following formula M5:

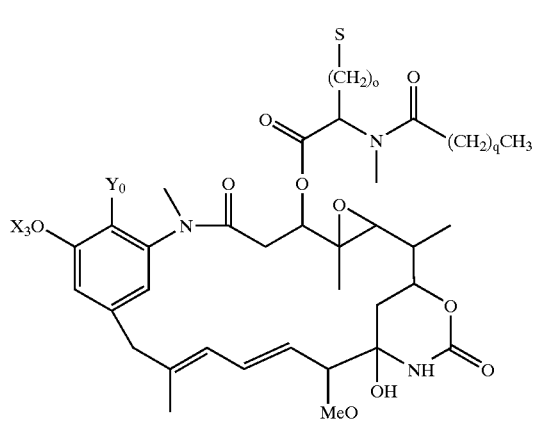

M5 wherein:

o is 1, 2 or 3;

q is an integer of from 0 to 10;

$Y_0$ is Cl or H; and $X_3$ is H or $CH_3$.

Also contemplated is the method according to the relevant examples above, wherein said thiol-containing taxane is a compound selected from the following formula T1:

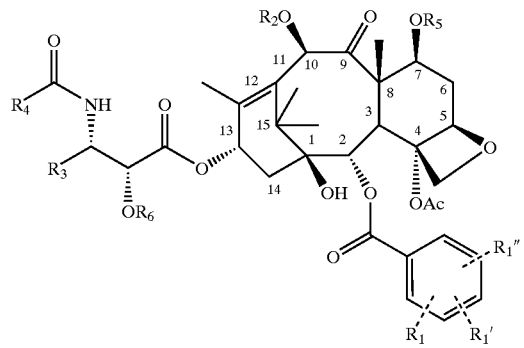

T1 wherein:

$R_1$ is H, an electron withdrawing group, or an electron donating group, and $R_1'$ and $R_1''$ are the same or different and are H, an electron withdrawing group, or an electron donating group;

$R_2$ is heterocyclic, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl;

$R_3$ is an aryl, or a linear, branched, or cyclic alkyl having from 1 to 10 carbon atoms;

$R_4$ is —$OC(CH_3)_3$ or phenyl;

$R_5$ is a thiol moiety; and $R_6$ is heterocyclic, H, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl.

Also contemplated is the method according to the relevant examples above, wherein $R_1$ is F, $NO_2$, CN, Cl, $CHF_2$, $CF_3$, —$OCH_3$, —$OCH_2CH_3$, or $NR_7R_8$, wherein:

$R_7$ and $R_8$ are the same or different and are linear, branched, or cyclic alkyl having 1 to 10 carbon atoms or simple or substituted aryl having 1 to 10 carbon atoms.

Also contemplated is the method according to the relevant examples above, wherein $R_7$ and $R_8$ each has 1 to 4 carbon atoms.

Also contemplated is the method according to the relevant examples above, wherein $R_7$ and $R_8$ are the same.

Also contemplated is the method according to the relevant examples above, wherein $R_7$ and $R_8$ are the same.

Also contemplated is the method according to the relevant examples above, wherein $R_2$ is —$COC_2H_5$, —$CH_2CH_3$, —$CONHCH_2CH_3$—CO-morpholino, —CO-piperidino, —CO-piperazino, or —CO-N-methylpiperazino.

Also contemplated is the method according to the relevant examples above, wherein $R_5$ is —$(CH_2)_nS$, —$CO(CH_2)_nS$, —$(CH_2)_nCH(CH_3)S$, —$CO(CH_2)_nCH(CH_3)S$, —$(CH_2)_nC(CH_3)_2S$, —$CO(CH_2)_nC(CH_3)_2S$, —$CONR_{12}(CH_2)_nS$, —$CONR_{12}(CH_2)_nCH(CH_3)S$, —$CONR_{12}(CH_2)_nC(CH_3)_2S$, —CO-morpholino-XS, —CO-piperidino-XS, —CO-piperazino-XS, or —CO-N-methylpiperazino-XS;

wherein n is an integer of 1 to 10; and wherein $R_{12}$ is H, a linear alkyl, branched alkyl or cyclic alkyl having 1 to 10 carbon atoms, or simple or substituted aryl having from 1 to 10 carbon atoms or heterocyclic.

Also contemplated is the method according to the relevant examples above, wherein $R_1$ is in the meta position when $R_1'$ and $R_1''$ are H or $OCH_3$.

Also contemplated is the method according to the relevant examples above, wherein $R_3$ is $-CH=C(CH_3)_2$.

Also contemplated is the method according to the relevant examples above, wherein said taxane is a compound selected from the following formula T1:

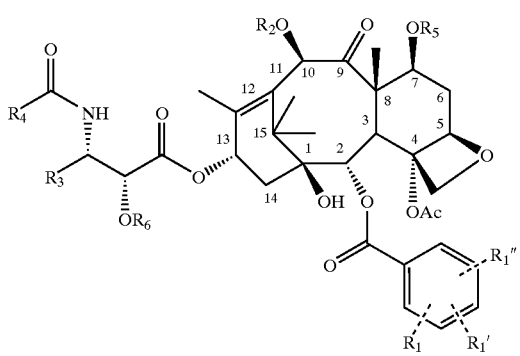

T1 wherein:
$R_1$ is H, an electron withdrawing group, or an electron donating group, and $R_1'$ and $R_1''$ are the same or different and are H, an electron withdrawing group, or an electron donating group;

$R_2$ is a thiol moiety;

$R_3$ is an aryl, or is a linear, branched, or cyclic alkyl having from 1 to 10 carbon atoms;

$R_4$ is $-OC(CH_3)_3$ or phenyl;

$R_5$ is heterocyclic, H, a linear, branched, or cyclic ester or ether having from 1 to 10 carbon atoms or a carbamate of the formula $-CONR_{10}R_{11}$, wherein $R_{10}$ and $R_{11}$ are the same or different and are H, linear, branched or cyclic alkyl having 1 to 10 carbon atoms or aryl; and $R_6$ is heterocyclic, H, a linear, branched, or cyclic ester or ether having from 1 to 10 carbon atoms or a carbamate of the formula $-CONR_{10}R_{11}$, wherein $R_{10}$ and $R_{11}$ are the same or different and are H, linear, branched or cyclic alkyl having 1 to 10 carbon atoms or aryl.

Also contemplated is the method according to the relevant examples above, wherein at least one of $R_1$ is F, $NO_2$, CN, Cl, $CHF_2$, $CF_3$, $-OCH_3$, $-OCH_2CH_3$, or $NR_7R_8$ wherein:
$R_7$ and $R_8$ are the same or different and are linear, branched, or cyclic alkyl having 1 to 10 carbon atoms or simple or substituted aryl having 1 to 10 carbon atoms.

Also contemplated is the method according to the relevant examples above, wherein $R_7$ and $R_8$ each has 1 to 4 carbon atoms.

Also contemplated is the method according to the relevant examples above, wherein $R_7$ and $R_8$ are the same.

Also contemplated is the method according to the relevant examples above, wherein $R_7$ and $R_8$ are the same.

Also contemplated is the method according to the relevant examples above, wherein $R_5$ is $-(CH_2)_nS$, $-CO(CH_2)_nS$, $-(CH_2)_nCH(CH_3)S$, $-CO(CH_2)_nCH(CH_3)S$, $-(CH_2)_nC(CH_3)_2S$, $-CO(CH_2)_nC(CH_3)_2S$, $-CONR_{12}(CH_2)_nS$, $-CONR_{12}(CH_2)_nCH(CH_3)S$, $-CONR_{12}(CH_2)_nC(CH_3)_2S$, $-CO$-morpholino-XS, $-CO$-piperidino-XS, $-CO$-piperazino-XS, or $-CO$-N-methylpiperazino-XS;
wherein n is an integer of 1 to 10; and
wherein $R_{12}$ is H, a linear alkyl, branched alkyl or cyclic alkyl having 1 to 10 carbon atoms, or simple or substituted aryl having from 1 to 10 carbon atoms or heterocyclic.

Also contemplated is the method according to the relevant examples above, wherein $R_5$ is $-COC_2H_5$, $-CH_2CH_3$, $-CONHCH_2CH_3$, $-CO$-morpholino, $-CO$-piperidino, $-CO$-piperazino, or $-CO$-N-methylpiperazino.

Also contemplated is the method according to the relevant examples above, wherein $R_1$ is in the meta position when $R_1'$ and $R_1''$ are H or $OCH_3$.

Also contemplated is the method according to the relevant examples above, wherein said taxane is a compound selected from the following formula T1:

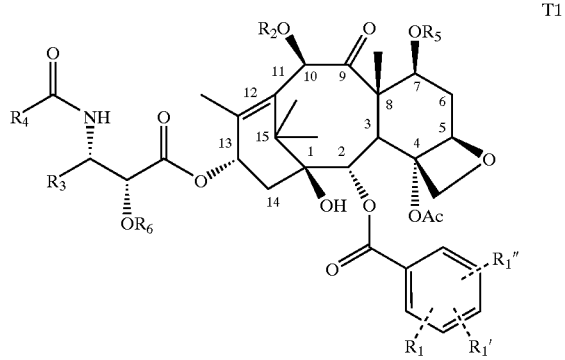

T1 wherein:
$R_1$ is H, an electron withdrawing group, or an electron donating group, and $R_1'$ and $R_1''$ are the same or different and are H, an electron withdrawing group, or an electron donating group;

$R_2$ is heterocyclic, a linear, branched, or cyclic ester or ether having from 1 to 10 carbon atoms or a carbamate of the formula $-CONR_{10}R_{11}$, wherein $R_{10}$ and $R_{11}$ are the same or different and are H, linear, branched or cyclic alkyl having 1 to 10 carbon atoms or aryl;

$R_3$ is an aryl, or is a linear, branched or cyclic alkyl having from 1 to 10 carbon atoms;

$R_4$ is $-OC(CH_3)_3$ or phenyl;

$R_5$ is heterocyclic, H, a linear, branched, or cyclic ester or ether having from 1 to 10 carbon atoms or a carbamate of the formula $-CONR_{10}R_{11}$, wherein $R_{10}$ and $R_{11}$ are the same or different and are H, linear, branched or cyclic alkyl having 1 to 10 carbon atoms or aryl;

$R_6$ is a thiol moiety.

Also contemplated is the method according to the relevant examples above, wherein $R_1$ is F, $NO_2$, CN, Cl, $CHF_2$, $CF_3$, $-OCH_3$, $-OCH_2CH_3$, or $NR_7R_8$ wherein:
$R_7$ and $R_8$ are the same or different and are linear, branched, or cyclic alkyl having 1 to 10 carbon atoms or simple or substituted aryl having 1 to 10 carbon atoms.

Also contemplated is the method according to the relevant examples above, wherein $R_7$ and $R_8$ each has 1 to 4 carbon atoms.

Also contemplated is the method according to the relevant examples above, wherein $R_7$ and $R_8$ are the same.

Also contemplated is the method according to the relevant examples above, wherein $R_7$ and $R_8$ are the same.

Also contemplated is the method according to the relevant examples above, wherein $R_2$ is $-COC_2H_5$, $-CH_2CH_3$, $-CONHCH_2CH_3$, $-CO$-morpholino, $-CO$-piperidino, $-CO$-piperazino, or $-CO$-N-methylpiperazino.

Also contemplated is the method according to the relevant examples above, wherein $R_5$ is —$(CH_2)_nS$, —$CO(CH_2)_nS$, —$(CH_2)_nCH(CH_3)S$, —$CO(CH_2)_nCH(CH_3)S$, —$(CH_2)_nC(CH_3)_2S$, —$CO(CH_2)_nC(CH_3)_2S$, —$CONR_{12}(CH_2)_nS$, —$CONR_{12}(CH_2)_nCH(CH_3)S$, —$CONR_{12}(CH_2)_nC(CH_3)_2S$, —CO-morpholino-XS, —CO-piperidino-XS, —CO-piperazino-XS, or —CO-N-methylpiperazino-XS;

wherein n is an integer of 1 to 10; and wherein $R_{12}$ is H, a linear alkyl, branched alkyl or cyclic alkyl having 1 to 10 carbon atoms, or simple or substituted aryl having from 1 to 10 carbon atoms or heterocyclic.

Also contemplated is the method according to the relevant examples above, wherein $R_1$ is in the meta position when $R_1'$ and $R_1''$ are H or $OCH_3$.

Also contemplated is the method according to the relevant examples above, wherein said thiol-containing CC-1065 analogue is acyclopropylbenzindole-containing cytotoxic compound formed from an A subunit of the formulae A-3 or A-4 covalently linked to either a B subunit of the formula F-1 or a B-C subunit of the formulae F-3 or F-7 via an amide bond from the secondary amino group of the pyrrole moiety of the A subunit to the C-2 carboxyl group of the B subunit, wherein the formulae A-3 and A-4 are as follows:

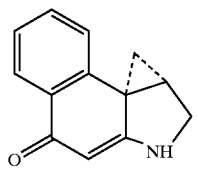

A-3

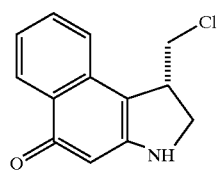

A-4 wherein the formulae F-1, F-3 and F-7 are as follows:

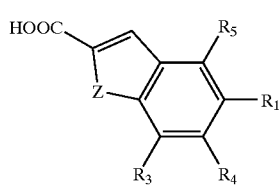

F-1

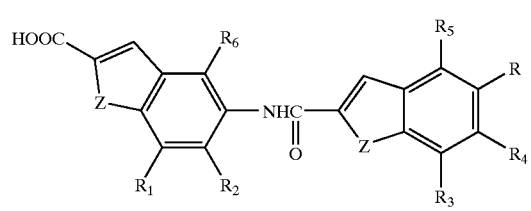

F-3

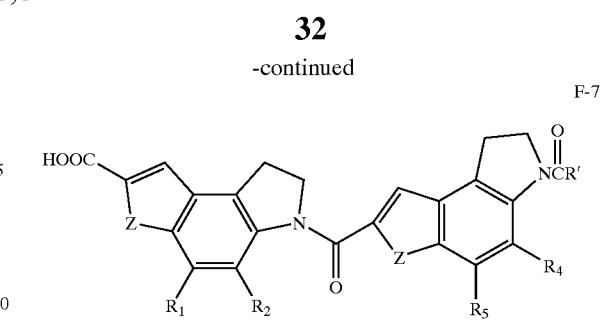

F-7 wherein each Z may be the same or different and may be O or NH; and wherein, in Formula F-1 $R_4$ is a thiol moiety, in Formula F-3 one of R or $R_4$ is a thiol moiety, in Formula F-7 one of R' or $R_4$ is a thiol moiety; when R or R' is a thiol moiety, then $R_1$ to $R_6$, which may be the same or different, are hydrogen, $C_1$–$C_3$ linear alkyl, methoxy, hydroxyl, primary amino, secondary amino, tertiary amino, or amido; and when $R_4$ is a thiol moiety, R, $R_1$, $R_2$, $R_3$, $R_4$, $R_5$ and $R_6$, which may be the same or different, are hydrogen, $C_1$–$C_3$ linear alkyl, methoxy, hydroxyl, primary amino, secondary amino, tertiary amino, or amido, and R' is $NH_2$, alkyl, O-alkyl, primary amino, secondary amino, tertiary amino, or amido.

Also contemplated is the method according to the relevant examples above, wherein R and R' are thiol moieties and $R_1$ to $R_6$ are each hydrogen.

Also contemplated is the method according to the relevant examples above, wherein R or $R_4$ is $NHCO(CH_2)_lS$, $NHCOC_6H_4(CH_2)_nS$, or $O(CH_2)_lS$, and R' is $(CH_2)_lS$, $NH(CH_2)_lS$ or $O(CH_2)_lS$ wherein:

l is an integer of 1 to 10.

Also contemplated is the method according to the relevant examples above, wherein R or $R_4$ is $NHCO(CH_2)_lS$, $NHCOC_6H_4(CH_2)_lS$, or $O(CH_2)_lS$, and R' is $(CH_2)_lS$, $NH(CH_2)_lS$ or $O(CH_2)_lS$ wherein:

l is an integer of 1 to 10.

Also contemplated is the method according to the relevant examples above, wherein l is 1.

Also contemplated is the method according to the relevant examples above, wherein l is 2.

Also contemplated is the method according to the relevant examples above, wherein said thiol-containing doxorubicin analogue is a compound selected from the following formula D2:

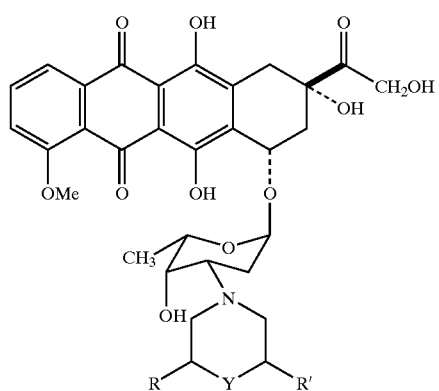

D2 wherein,

Y is O or $NR_2$, wherein $R_2$ is linear or branched alkyl having 1 to 5 carbon atoms;

R is a thiol moiety, H, or liner or branched alkyl having 1 to 5 carbon atoms; and R' is a thiol moiety, H, or —$OR_1$, wherein $R_1$ is linear or branched alkyl having 1 to 5 carbon atoms;

provided that R and R' are not thiol moieties at the same time.

Also contemplated is the method according to the relevant examples above, wherein $NR_2$ is $NCH_3$.

Also contemplated is the method according to the relevant examples above, wherein R' is —O.

Also contemplated is the method according to the relevant examples above, wherein the thiol moiety is —$(CH_2)_nS$, —$O(CH_2)_nS$, —$(CH_2)_nCH(CH_3)S$, —$O(CH_2)_nCH(CH_3)S$, —$(CH_2)_nC(CH_3)_2S$, or —$O(CH_2)_nC(CH_3)_2S$, wherein n is an integer of 1 to 10.

Also contemplated is the method according to the relevant examples above, wherein said thiol-containing daunorubicin analogue is a compound selected from the following formula D3:

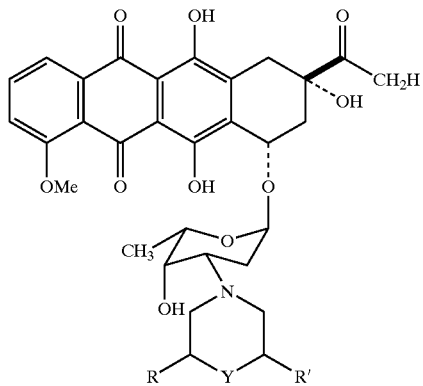

wherein,

Y is O or $NR_2$, wherein $R_2$ is linear or branched alkyl having 1 to 5 carbon atoms;

R is a thiol moiety, H, or liner or branched alkyl having 1 to 5 carbon atoms; and R' is a thiol moiety, H, or —$OR_1$, wherein $R_1$ is linear or branched alkyl having 1 to 5 carbon atoms;

provided that R and R' are not thiol moieties at the same time.

Also contemplated is the method according to the relevant examples above, wherein $NR_2$ is $NCH_3$.

Also contemplated is the method according to the relevant examples above, wherein R' is —O.

Also contemplated is the method according to the relevant examples above, wherein the thiol moiety is —$(CH_2)_nS$, —$O(CH_2)_nS$, —$(CH_2)_nCH(CH_3)S$, —$O(CH_2)_nCH(CH_3)S$, —$(CH_2)_nC(CH_3)_2S$, or —$O(CH_2)_nC(CH_3)_2S$, wherein n is an integer of 1 to 10.

In a fifth embodiment of the invention, a method for producing a cytotoxic conjugate comprising one or more cytotoxic agents covalently bonded to a cell-binding agent through a PEG linking group is disclosed. The method comprises reacting one or more cytotoxic agents with a cell-binding agent, wherein each cytotoxic agent bears a PEG linking group having a terminal active ester, thereby producing a cytotoxic conjugate.

In a preferred embodiment, the PEG linking group has from 1 to 20 monomeric units. In an equally preferred embodiment, the PEG linking group has from 21 to 40 monomeric units. In a further equally preferred embodiment, the PEG linking group has from 41 to 1000 monomeric units.

Specifically contemplated is a method for producing a cytotoxic conjugate which comprises one or more cytotoxic agents covalently bonded to a cell-binding agent through a PEG linking group having 1 to 20 monomeric units, said method comprising reacting one or more cytotoxic agents with a cell-binding agent, wherein said one or more cytotoxic agents each bears a PEG linking group having a terminal active ester and 1 to 20 monomeric units, and wherein said cytotoxic agent bearing a PEG linking group having a terminal active ester and 1 to 20 monomeric units is a compound of formula 2:

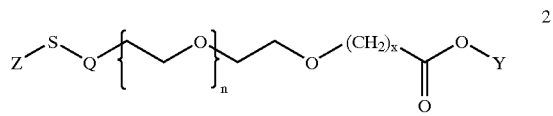

wherein Z is said cytotoxic agent;

wherein Q is $R_2COO$—, $R_2R_3NCOO$—, $R_2OCOO$—, $R_2O$—, $R_2CONR_3$—, $R_2R_3N$—, $R_2OCONR_3$—, or S—, wherein:

$R_2$ is $SCR_4R_5R_6$—, $R_4$, $R_5$ and $R_6$ are each H, linear alkyl, cyclic alkyl or branched alkyl, and may be the same or different, $R_3$ is H or a linear alkyl, cyclic alkyl or branched alkyl;

wherein n is an integer of from 0 to 20;

wherein x is 1 or 2; and wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl, thereby producing a cytotoxic conjugate, illustrated in formula 3 with a linkage of one of said one or more cytotoxic agents

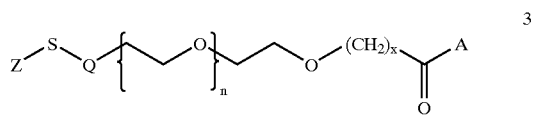

wherein Z is said cytotoxic agent;

wherein Q is $R_2COO$—, $R_2R_3NCOO$—, $R_2OCOO$—, $R_2O$—, $R_2CONR_3$—, $R_2R_3N$—, $R_2OCONR_3$—, or S—, wherein:

$R_2$ is $SCR_4R_5R_6$—, $R_4$, $R_5$ and $R_6$ are each H, linear alkyl, cyclic alkyl or branched alkyl, and may be the same or different, $R_3$ is H or a linear alkyl, cyclic alkyl or branched alkyl;

wherein n is an integer of from 0 to 20;

wherein x is 1 or 2; and wherein A is said cell-binding agent.

Also specifically contemplated is a method for producing a cytotoxic conjugate which comprises one or more cytotoxic agents covalently bonded to a cell-binding agent through a PEG linking group having 21 to 40 monomeric units, said method comprising reacting one or more cytotoxic agents with a cell-binding agent, wherein said one or more cytotoxic agents each bears a PEG linking group having a terminal active ester and 21 to 40 monomeric units, and wherein said cytotoxic agent bearing a PEG linking group having a terminal active ester and 21 to 40 monomeric units is a compound of formula 2:

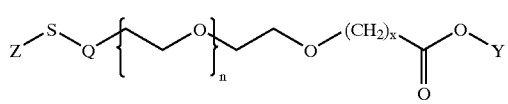

2 wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or S—,
  wherein:
  $R_2$ is $SCR_4R_5R_6-$,
    $R_4$, $R_5$ and $R_6$ are each H, linear alkyl, cyclic alkyl or branched alkyl, and may be the same or different,
  $R_3$ is H or a linear alkyl, cyclic alkyl or branched alkyl;
wherein n is an integer of from 21 to 40;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl,
  thereby producing a cytotoxic conjugate, illustrated in formula 3 with a linkage of one of said one or more cytotoxic agents

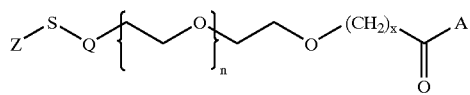

3 wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or S—,
  wherein:
  $R_2$ is $SCR_4R_5R_6-$,
    $R_4$, $R_5$ and R are each H, linear alkyl, cyclic, alkyl or branched alkyl, and may be the same or different,
  $R_3$ is H or a linear alkyl, cyclic alkyl or branched alkyl;
wherein n is an integer of from 21 to 40;
wherein x is 1 or 2; and
wherein A is said cell-binding agent.

Also specifically contemplated is a method for producing a cytotoxic conjugate which comprises one or more cytotoxic agents covalently bonded to a cell-binding agent through a PEG linking group having 41 to 1000 monomeric units, said method comprising reacting one or more cytotoxic agents with a cell-binding agent, wherein said one or more cytotoxic agents each bears a PEG linking group having a terminal active ester and 41 to 1000 monomeric units, and wherein said cytotoxic agent bearing a PEG linking group having a terminal active ester and 41 to 1000 monomeric units is a compound of formula 2:

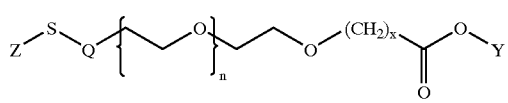

2 wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or S—,
  wherein:
  $R_2$ is $SCR_4R_5R_6-$,
    $R_4$, $R_5$ and $R_6$ are each H, linear alkyl, cyclic alkyl or branched alkyl, and may be the same or different,
  $R_3$ is H or a linear alkyl, cyclic alkyl or branched alkyl;
wherein n is an integer of from 41 to 1000;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl,
  thereby producing a cytotoxic conjugate, illustrated in formula 3 with a linkage of one of said one or more cytotoxic agents

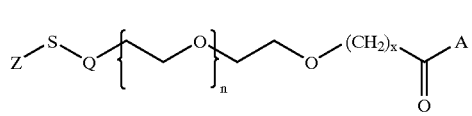

3 wherein Z is said cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or S—,
  wherein:
  $R_2$ is $SCR_4R_5R_6-$,
    $R_4$, $R_5$ and $R_6$ are each H, linear alkyl, cyclic alkyl or branched alkyl, and may be the same or different,
  $R_3$ is H or a linear alkyl, cyclic alkyl or branched alkyl;
wherein n is an integer of from 41 to 1000;
wherein x is 1 or 2; and
wherein A is said cell-binding agent.

Also contemplated is the method for producing a cytotoxic conjugate according to any one of the relevant examples above, wherein said cytotoxic agent is selected from the group consisting of an thiol-containing maytansinoid, thiol-containing taxane, thiol-containing CC-1065 analogue, thiol-containing daunorubicin analogue and thiol-containing doxorubicin analogue, and thiol-containing analogues or derivatives thereof, and said cell-binding agent is selected from the group consisting of a polyclonal antibody, monoclonal antibody, antibody fragment, interferon, lymphokine, hormone, growth factor, vitamin and nutrient-transport molecule.

Also contemplated is the method according to the relevant examples above, wherein said thiol-containing maytansinoid is a C-3 thiol-containing maytansinoid.

Also contemplated is the method according to the relevant examples above, wherein said C-3 thiol-containing maytansinoid is an N-methyl-alanine-containing C-3 thiol-containing maytansinoid.

Also contemplated is the method according to the relevant examples above, wherein said N-methyl-alanine-containing C-3 thiol-containing maytansinoid is a compound selected from the following formula M1:

M1

[Structure M1]

wherein:

l is an integer of from 1 to 10; and may is a maytansinoid.

Also contemplated is the method according to the relevant examples above, wherein said N-methyl-alanine-containing C-3 thiol-containing maytansinoid is a compound selected from the following formula M2:

M2

[Structure M2]

wherein:

R₁ and R₂ are H, CH₃ or CH₂CH₃, and may be the same or different;

m is 0, 1, 2 or 3; and may is a maytansinoid.

Also contemplated is the method according to the relevant examples above, wherein said N-methyl-alanine-containing C-3 thiol-containing maytansinoid is a compound selected from the following formula M3:

M3

[Structure M3]

wherein:

n is an integer of from 3 to 8; and may is a maytansinoid.

Also contemplated is the method according to the relevant examples above, wherein said N-methyl-alanine-containing C-3 thiol-containing maytansinoid is a N-methyl-alanine-containing C-3 thiol-containing maytansinol.

Also contemplated is the method according to the relevant examples above, wherein said N-methyl-alanine-containing C-3 thiol-containing maytansinol is a dechloro maytansinol.

Also contemplated is the method according to the relevant examples above, wherein said N-methyl-alanine-containing C-3 thiol-containing maytansinol is a compound selected from the following formula M6:

M6

[Structure M6]

wherein:

l is 1, 2 or 3;

Y₀ is Cl or H; and

X₃ is H or CH₃.

Also contemplated is the method according to the relevant examples above, wherein said C-3 thiol-containing maytansinoid is an N-methyl-cysteine-containing C-3 thiol-containing maytansinoid.

Also contemplated is the method according to the relevant examples above, wherein said N-methyl-cysteine-containing C-3 thiol-containing maytansinoid is a compound selected from the following formula M4:

M4

[Structure M4]

wherein:

o is 1, 2 or 3;

p is an integer of 0 to 10; and may is a maytansinoid.

Also contemplated is the method according to the relevant examples above, wherein said N-methyl-cysteine-containing C-3 thiol-containing maytansinoid is a N-methyl-cysteine-containing C-3 thiol-containing maytansinol.

Also contemplated is the method according to the relevant examples above, wherein said N-methyl-cysteine-containing C-3 thiol-containing maytansinol is a dechloro maytansinol.

Also contemplated is the method according to the relevant examples above, wherein said N-methyl-cysteine-containing C-3 thiol-containing maytansinol is a compound selected from the following formula M5:

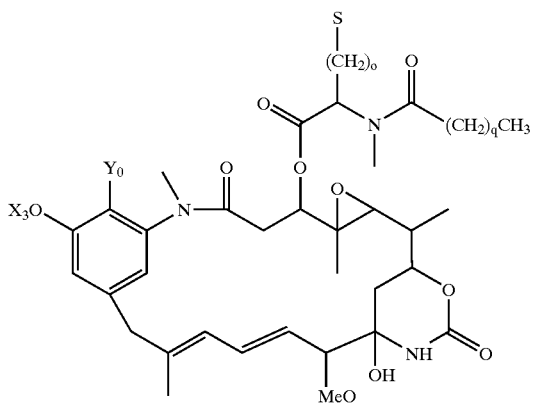

wherein:
o is 1, 2 or 3;
q is an integer of from 0 to 10;
$Y_0$ is Cl or H; and
$X_3$ is H or $CH_3$.

Also contemplated is the method according to the relevant examples above, wherein said thiol-containing taxane is a compound selected from the following formula T1:

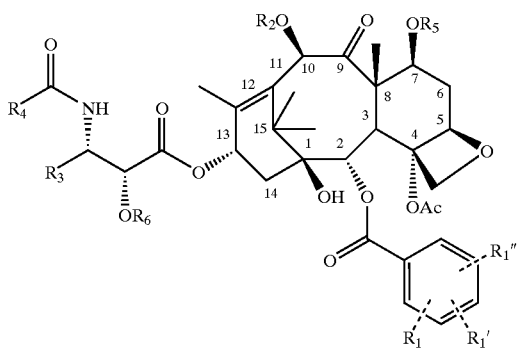

wherein:
$R_1$ is H, an electron withdrawing group, or an electron donating group, and $R_1'$ and $R_1''$ are the same or different and are H, an electron withdrawing group, or an electron donating group;
$R_2$ is heterocyclic, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl;
$R_3$ is an aryl, or a linear, branched, or cyclic alkyl having from 1 to 10 carbon atoms;
$R_4$ is —$OC(CH_3)_3$ or phenyl;
$R_5$ is a thiol moiety; and
$R_6$ is heterocyclic, H, a linear, branched, or cyclic ester or ether having from 1 to 10 carbon atoms or a carbamate of the formula —$CONR_1OR_{11}$, wherein $R_{10}$ and $R_{11}$ are the same or different and are H, linear, branched or cyclic alkyl having 1 to 10 carbon atoms or aryl.

Also contemplated is the method according to the relevant examples above, wherein $R_1$ is F, $NO_2$, CN, Cl, $CHF_2$, $CF_3$, —$OCH_3$, —$OCH_2CH_3$, or $NR_7R_8$, wherein:

$R_7$ and $R_8$ are the same or different and are linear, branched, or cyclic alkyl having 1 to 10 carbon atoms or simple or substituted aryl having 1 to 10 carbon atoms.

Also contemplated is the method according to the relevant examples above, wherein $R_7$ and $R_8$ each has 1 to 4 carbon atoms.

Also contemplated is the method according to the relevant examples above, wherein $R_7$ and $R_8$ are the same.

Also contemplated is the method according to the relevant examples above, wherein $R_7$ and $R_8$ are the same.

Also contemplated is the method according to the relevant examples above, wherein $R_2$ is —$COC_2H_5$, —$CH_2CH_3$, —$CONHCH_2CH_3$—CO-morpholino, —CO-piperidino, —CO-piperazino, or —CO-N-methylpiperazino.

Also contemplated is the method according to the relevant examples above, wherein $R_5$ is —$(CH_2)_nS$, —$CO(CH_2)_nS$, —$(CH_2)_nCH(CH_3)S$, —$CO(CH_2)_nCH(CH_3)S$, —$(CH_2)_nC(CH_3)_2S$, —$CO(CH_2)_nC(CH_3)_2S$, —$CONR_{12}(CH_2)_nS$, —$CONR_{12}(CH_2)_nCH(CH_3)S$, —$CONR_{12}(CH_2)_nC(CH_3)_2S$, —CO-morpholino-XS, —CO-piperidino-XS, —CO-piperazino-XS, or —CO-N-methylpiperazino-XS;
wherein n is an integer of 1 to 10; and
wherein $R_{12}$ is H, a linear alkyl, branched alkyl or cyclic alkyl having 1 to 10 carbon atoms, or simple or substituted aryl having from 1 to 10 carbon atoms or heterocyclic.

Also contemplated is the method according to the relevant examples above, wherein $R_1$ is in the meta position when $R_1'$ and $R_1''$ are H or $OCH_3$.

Also contemplated is the method according to the relevant examples above, wherein $R_3$ is —CH=$C(CH_3)_2$.

Also contemplated is the method according to the relevant examples above, wherein said taxane is a compound selected from the following formula T1:

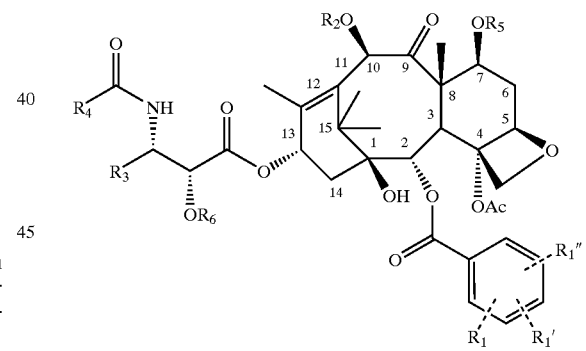

wherein:
$R_1$ is H, an electron withdrawing group, or an electron donating group, and $R_1'$ and $R_1''$ are the same or different and are H, an electron withdrawing group, or an electron donating group;
$R_2$ is a thiol moiety;
$R_3$ is an aryl, or is a linear, branched, or cyclic alkyl having from 1 to 10 carbon atoms;
$R_4$ is —$OC(CH_3)_3$ or phenyl;
$R_5$ is heterocyclic, H, a linear, branched, or cyclic ester or ether having from 1 to 10 carbon atoms or a carbamate of the formula —$CONR_{10}R_{11}$, wherein $R_{10}$ and $R_{11}$ are the same or different and are H, linear, branched or cyclic alkyl having 1 to 10 carbon atoms or aryl; and
$R_6$ is heterocyclic, H, a linear, branched, or cyclic ester or ether having from 1 to 10 carbon atoms or a carbamate of the formula —CONR$_{10}$R$_{11}$, wherein R$_{10}$ and R$_{11}$ are the same or different and are H, linear, branched or cyclic alkyl having 1 to 10 carbon atoms or aryl.

Also contemplated is the method according to the relevant examples above, wherein at least one of R$_1$ is F, NO$_2$, CN, Cl, CHF$_2$, CF$_3$, —OCH$_3$, —OCH$_2$CH$_3$, or NR$_7$R$_8$ wherein:
R$_7$ and R$_8$ are the same or different and are linear, branched, or cyclic alkyl having 1 to 10 carbon atoms or simple or substituted aryl having 1 to 10 carbon atoms.

Also contemplated is the method according to the relevant examples above, wherein R$_7$ and R$_8$ each has 1 to 4 carbon atoms.

Also contemplated is the method according to the relevant examples above, wherein R$_7$ and R$_8$ are the same.

Also contemplated is the method according to the relevant examples above, wherein R$_7$ and R$_8$ are the same.

Also contemplated is the method according to the relevant examples above, wherein R$_5$ is —(CH$_2$)$_n$S, —CO(CH$_2$)$_n$S, —(CH$_2$)$_n$CH(CH$_3$)S, —CO(CH$_2$)$_n$CH(CH$_3$)S, —(CH$_2$)$_n$C(CH$_3$)$_2$S, —CO(CH$_2$)$_n$C(CH$_3$)$_2$S, —CONR$_{12}$(CH$_2$)$_n$S, —CONR$_{12}$(CH$_2$)$_n$CH(CH$_3$)S, —CONR$_{12}$(CH$_2$)$_n$C(CH$_3$)$_2$S, —CO-morpholino-XS, —CO-piperidino-XS, —CO-piperazino-XS, or —CO-N-methylpiperazino-XS;
wherein n is an integer of 1 to 10; and
wherein R$_{12}$ is H, a linear alkyl, branched alkyl or cyclic alkyl having 1 to 10 carbon atoms, or simple or substituted aryl having from 1 to 10 carbon atoms or heterocyclic.

Also contemplated is the method according to the relevant examples above, wherein R$_5$ is —COC$_2$H$_5$, —CH$_2$CH$_3$, —CONHCH$_2$CH$_3$, —CO-morpholino, —CO-piperidino, —CO-piperazino, or —CO-N-methylpiperazino.

Also contemplated is the method according to the relevant examples above, wherein R$_1$ is in the meta position when R$_1$' and R$_1$" are H or OCH$_3$.

Also contemplated is the method according to the relevant examples above, wherein said taxane is a compound selected from the following formula T1:

T1 wherein:
R$_1$ is H, an electron withdrawing group, or an electron donating group, and R$_1$' and R$_1$" are the same or different and are H, an electron withdrawing group, or an electron donating group;
R$_2$ is heterocyclic, a linear, branched, or cyclic ester or ether having from 1 to 10 carbon atoms or a carbamate of the formula —CONR$_{10}$R$_{11}$, wherein R$_{10}$ and R$_{11}$ are the same or different and are H, linear, branched or cyclic alkyl having 1 to 10 carbon atoms or aryl;
R$_3$ is an aryl, or is a linear, branched or cyclic alkyl having from 1 to 10 carbon atoms;
R$_4$ is —OC(CH$_3$)$_3$ or phenyl;
R$_5$ is heterocyclic, H, a linear, branched, or cyclic ester or ether having from 1 to 10 carbon atoms or a carbamate of the formula —CONR$_{10}$R$_{11}$, wherein R$_{10}$ and R$_{11}$ are the same or different and are H, linear, branched or cyclic alkyl having 1 to 10 carbon atoms or aryl;
R$_6$ is a thiol moiety.

Also contemplated is the method according to the relevant examples above, wherein R$_1$ is F, NO$_2$, CN, Cl, CHF$_2$, CF$_3$, —OCH$_3$, —OCH$_2$CH$_3$, or NR$_7$R$_8$ wherein:
R$_7$ and R$_8$ are the same or different and are linear, branched, or cyclic alkyl having 1 to carbon atoms or simple or substituted aryl having 1 to 10 carbon atoms.

Also contemplated is the method according to the relevant examples above, wherein R$_7$ and R$_8$ each has 1 to 4 carbon atoms.

Also contemplated is the method according to the relevant examples above, wherein R$_7$ and R$_8$ are the same.

Also contemplated is the method according to the relevant examples above, wherein R$_7$ and R$_8$ are the same.

Also contemplated is the method according to the relevant examples above, wherein R$_2$ is —COC$_2$H$_5$, —CH$_2$CH$_3$, —CONHCH$_2$CH$_3$, —CO-morpholino, —CO-piperidino, —CO-piperazino, or —CO-N-methylpiperazino.

Also contemplated is the method according to the relevant examples above, wherein R$_5$ is —(CH$_2$)$_n$S, —CO(CH$_2$)$_n$S, —(CH$_2$)$_n$CH(CH$_3$)S, —CO(CH$_2$)$_n$CH(CH$_3$)S, —(CH$_2$)$_n$C(CH$_3$)$_2$S, —CO(CH$_2$)$_n$C(CH$_3$)$_2$S, —CONR$_{12}$(CH$_2$)$_n$S, —CONR$_{12}$(CH$_2$)$_n$CH(CH$_3$)S, —CONR$_{12}$(CH$_2$)$_n$C(CH$_3$)$_2$S, —CO-morpholino-XS, —CO-piperidino-XS, —CO-piperazino-XS, or —CO-N-methylpiperazino-XS;
wherein n is an integer of 1 to 10; and
wherein R$_{12}$ is H, a linear alkyl, branched alkyl or cyclic alkyl having 1 to 10 carbon atoms, or simple or substituted aryl having from 1 to 10 carbon atoms or heterocyclic.

Also contemplated is the method according to the relevant examples above, wherein R$_1$ is in the meta position when R$_1$' and R$_1$" are H or OCH$_3$.

Also contemplated is the method according to the relevant examples above, wherein said thiol-containing CC-1065 analogue is a cyclopropylbenzindole-containing cytotoxic compound formed from an A subunit of the formulae A-3 or A-4 covalently linked to either a B subunit of the formula F-1 or a B-C subunit of the formulae F-3 or F-7 via an amide bond from the secondary amino group of the pyrrole moiety of the A subunit to the C-2 carboxyl group of the B subunit, wherein the formulae A-3 and A-4 are as follows:

A-3

A-4 wherein the formulae F-1, F-3 and F-7 are as follows:

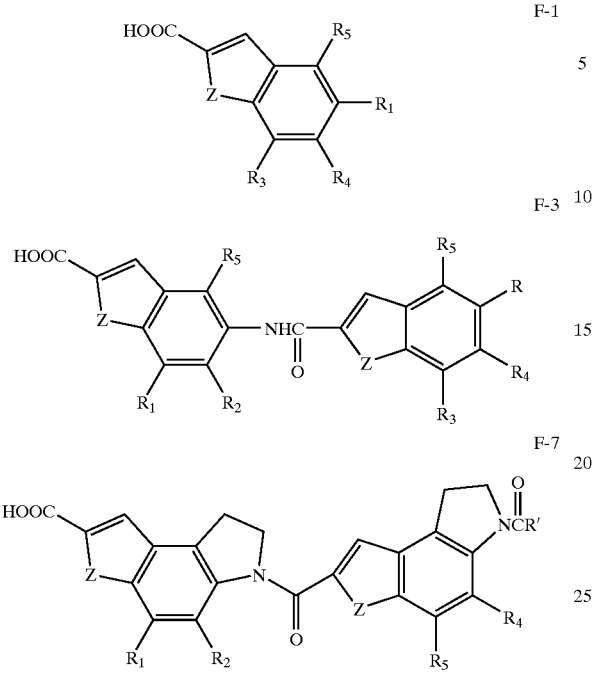

wherein each Z may be the same or different and may be O or NH; and wherein, in Formula F-1 R$_4$ is a thiol moiety, in Formula F-3 one of R or R$_4$ is a thiol moiety, in Formula F-7 one of R' or R$_4$ is a thiol moiety; when R or R' is a thiol moiety, then R$_1$ to R$_6$, which may be the same or different, are hydrogen, C$_1$–C$_3$ linear alkyl, methoxy, hydroxyl, primary amino, secondary amino, tertiary amino, or amido; and when R$_4$ is a thiol moiety, R, R$_1$, R$_2$, R$_3$, R$_4$, R$_5$ and R$_6$, which may be the same or different, are hydrogen, C$_1$–C$_3$ linear alkyl, methoxy, hydroxyl, primary amino, secondary amino, tertiary amino, or amido, and R' is NH$_2$, alkyl, O-alkyl, primary amino, secondary amino, tertiary amino, or amido.

Also contemplated is the method according to the relevant examples above, wherein R and R' are thiol moieties and R$_1$ to R$_6$ are each hydrogen.

Also contemplated is the method according to the relevant examples above, wherein R or R$_4$ is NHCO(CH$_2$)$_l$S, NHCOC$_6$H$_4$(CH$_2$)$_l$S, or O(CH$_2$)$_l$S, and R' is (CH$_2$)$_l$S, NH(CH$_2$)$_l$S or O(CH$_2$)$_l$S wherein:

l is an integer of 1 to 10.

Also contemplated is the method according to the relevant examples above, wherein R or R$_4$ is NHCO(CH$_2$)$_l$S, NHCOC$_6$H$_4$(CH$_2$)$_l$S, or O(CH$_2$)$_l$S, and R' is (CH$_2$)$_l$S, NH(CH$_2$)$_l$S or O(CH$_2$)$_l$S wherein:

l is an integer of 1 to 10.

Also contemplated is the method according to the relevant examples above, wherein l is 1.

Also contemplated is the method according to the relevant examples above, wherein l is 2.

Also contemplated is the method according to the relevant examples above, wherein said thiol-containing doxorubicin analogue is a compound selected from the following formula D2:

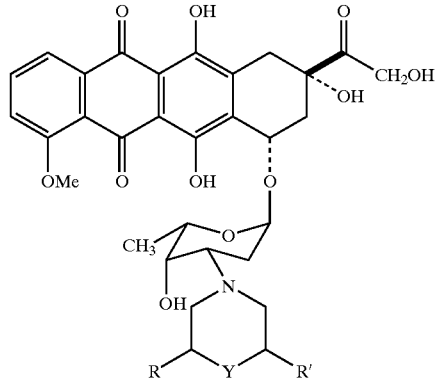

wherein,
Y is O or NR$_2$, wherein R$_2$ is linear or branched alkyl having 1 to 5 carbon atoms;
R is a thiol moiety, H, or liner or branched alkyl having 1 to 5 carbon atoms; and
R' is a thiol moiety, H, or —OR$_1$, wherein R$_1$ is linear or branched alkyl having 1 to 5 carbon atoms;
provided that R and R' are not thiol moieties at the same time.

Also contemplated is the method according to the relevant examples above, wherein NR$_2$ is NCH$_3$.

Also contemplated is the method according to the relevant examples above, wherein R' is —O.

Also contemplated is the method according to the relevant examples above, wherein the thiol moiety is —(CH$_2$)$_n$S, —O(CH$_2$)$_n$S, —(CH$_2$)$_n$CH(CH$_3$)S, —O(CH$_2$)$_n$CH(CH$_3$)S, —(CH$_2$)$_n$C(CH$_3$)$_2$S, or —O(CH$_2$)$_n$C(CH$_3$)$_2$S, wherein n is an integer of 1 to 10.

Also contemplated is the method according to the relevant examples above, wherein said thiol-containing daunorubicin analogue is a compound selected from the following formula D3:

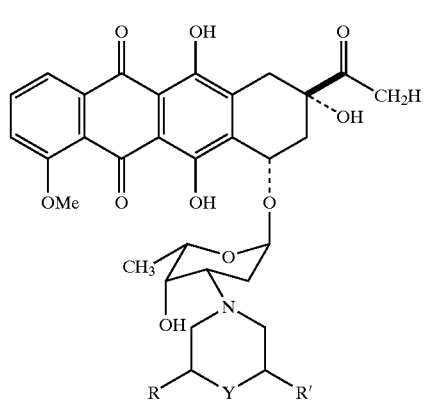

wherein,
Y is O or NR$_2$, wherein R$_2$ is linear or branched alkyl having 1 to 5 carbon atoms;
R is a thiol moiety, H, or liner or branched alkyl having 1 to 5 carbon atoms; and
R' is a thiol moiety, H, or OR$_1$, wherein R$_1$ is linear or branched alkyl having 1 to 5 carbon atoms;
provided that R and R' are not thiol moieties at the same time.

Also contemplated is the method according to the relevant examples above, wherein $NR_2$ is $NCH_3$.

Also contemplated is the method according to the relevant examples above, wherein R' is —O.

Also contemplated is the method according to the relevant examples above, wherein the thiol moiety is —$(CH_2)_nS$, —$O(CH_2)_nS$, —$(CH_2)_nCH(CH_3)S$, —$O(CH_2)_nCH(CH_3)S$, —$(CH_2)_nC(CH_3)_2S$, or —$O(CH_2)_nC(CH_3)_2S$, wherein n is an integer of 1 to 10.

Also contemplated is the method according to the relevant examples above, wherein said cell-binding agent is a monoclonal antibody.

Also contemplated is the method according to the relevant examples above, wherein said cell-binding agent is an antibody fragment.

Also contemplated is the method according to the relevant examples above, wherein said cytotoxic agent is a taxane and said cell-binding agent is a monoclonal antibody.

Also contemplated is the method according to any one of the relevant examples above, wherein said method further comprises the initial step of preparing a cytotoxic agent, bearing a PEG linking group having a terminal active ester, said initial step comprising reacting a thiol-containing cytotoxic agent with a PEG linking group of formula 1:

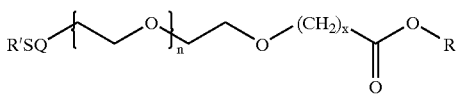

wherein R' is 2-pyridyl, 4-pyridyl, 5-nitro-2-pyridyl, 5-nitro-4-pyridyl, 2-nitrophenyl, 4-nitrophenyl or 2,4-dinitrophenyl;

wherein Q is $R_2COO$—, $R_2R_3NCOO$—, $R_2OCOO$—, $R_2O$—, $R_2CONR_3$—, $R_2R_3N$—, $R_2OCONR_3$—, or S—, wherein:
$R_2$ is $SCR_4R_5R_6$—,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;

wherein n is an integer of from 0 to 20, n is an integer of from 21 to 40, or n is an integer of from 41 to 1000;

wherein x is 1 or 2; and wherein R is H, a cation to form a salt or a chemical group to form an ester.

In a final embodiment of the invention, a method of killing selected cell populations comprising contacting target cells, or tissue containing target cells, with an effective amount of one of the cytotoxic conjugates or therapeutic compositions disclosed herein, is disclosed.

Specifically contemplated is a method of killing selected cell populations comprising contacting target cells, or tissue containing target cells, with an effective amount of the cytotoxic conjugate of the relevant examples above.

BRIEF DESCRIPTION OF THE DRAWINGS

In FIG. 1, n is any integer; X is a chemical group to form an ester; and x is 1 or 2.

FIG. 2 shows the conversion of carboxy-PEG linkers into ω-mercaptocarboxy-PEG linkers, followed by their further conversion into hetero-bifunctional PEG linking groups of the formula 13. The protective chemical group on the terminus of compounds of formula 13 may be removed to yield a carboxylate compound of formula 14. In turn, a salt of a compound of formula 14 may be prepared to yield a compound of formula 15. In FIG. 2, n is any integer; x is 1 or 2; X is a chemical group to form an ester; R' is 2-pyridyl, 4-pyridyl, 5-nitro-2-pyridyl, 5-nitro-4-pyridyl, 2-nitrophenyl, 4-nitrophenyl or 2,4-dinitrophenyl; and M is a cation to form a salt.

FIG. 3A shows the formation of compounds of formula 19 through two alternative reaction schemes. Compounds of formula 19 are then converted to hetero-bifunctional PEG linking groups of formulae 20, 23 and 26, as shown in FIGS. 3B, 3C and 3D, respectively. In each of the latter three figures, the removal of the protective chemical group to yield carboxylate compounds of formulae 21, 24 and 27 is also shown. Similarly, the production of a salt of the compounds, to yield compounds of formulae 22, 25 and 28 are also shown. In FIG. 3A, n is any integer; x is 1 or 2; X is a chemical group to form an ester; and $R_3$ is H or a linear alkyl, cyclic alkyl or branched alkyl. In FIGS. 3B, 3C and 3D, $R_3$ is H or a linear alkyl, cyclic alkyl or branched alkyl; n is any integer; x is 1 or 2; X is a chemical group to form an ester; $R_2$ is $R'SSCR_4R_5R_6$—; R' is 2-pyridyl, 4-pyridyl, 5-nitro-2-pyridyl, 5-nitro-4-pyridyl, 2-nitrophenyl, 4-nitrophenyl or 2,4-dinitrophenyl; $R_4$, $R_5$ and $R_6$ are each H, linear alkyl, cyclic alkyl or branched alkyl, and may be the same or different; and M is a cation to form a salt.

FIGS. 4A–4D show the conversion of carboxy-PEG linkers into hetero-bifunctional PEG linking groups of formulae 29, 32, 35 and 38. FIG. 4A shows the production of compounds of formula 29, followed by the removal of the protective chemical group to yield carboxylate compounds of formula 30, followed by the production of a salt of compounds of formula 30 to yield compounds of formula 31. Similarly, FIGS. 4B–4D show the production of compounds of formulae 32, 35 and 38, followed by the removal of the protective chemical group to yield carboxylate compounds of formulae 33, 36 and 39, followed by the production of salts of compounds of formulae 33, 36 and 39 to yield a compound of formulae 34, 37 and 40, respectively. In FIGS. 4A, 4C and 4D; n is any integer; x is 1 or 2; X is a chemical group to form an ester; $R_2$ is $R'SSCR_4R_5R_6$—; R' is 2-pyridyl, 4-pyridyl, 5-nitro-2-pyridyl, 5-nitro-4-pyridyl, 2-nitrophenyl, 4-nitrophenyl or 2,4-dinitrophenyl; $R_4$, $R_5$ and $R_6$ are each H, linear alkyl, cyclic alkyl or branched alkyl, and may be the same or different; and M is a cation to form a salt. In FIG. 4B, $R_3$ is H or a linear alkyl, cyclic alkyl or branched alkyl; n is any integer; x is 1 or 2; X is a chemical group to form an ester; $R_2$ is $R'SSCR_4R_5R_6$—; R' is 2-pyridyl, 4-pyridyl, 5-nitro-2-pyridyl, 5-nitro-4-pyridyl, 2-nitrophenyl, 4-nitrophenyl or 2,4-dinitrophenyl; $R_4$, $R_5$ and $R_6$ are each H, linear alkyl, cyclic alkyl or branched alkyl, and may be the same or different; and M is a cation to form a salt.

FIG. 7 shows the preparation of hetero-bifunctional PEG linking group 15-(2-pyridyldithio)-4,7,10,13-tetraoxapentadecanoic acid tert-butyl ester 13a, followed by its conversion to 15-(2-pyridyldithio)-4,7,10,13-tetraoxapentadecanoic acid 14a.

FIG. 8 shows the preparation of hetero-bifunctional PEG linking group 15-[N-(3-(2-pyridyldithio)-propionyl)]-4,7,10,13-tetraoxapentadecanoic acid tert-butyl ester 20a, followed by its conversion to 15-[N-(3-(2-pyridyldithio)-propionyl]-4,7,10,13-tetraoxapentadecanoic acid 21a.

FIG. 9 shows the preparation of hetero-bifunctional PEG linking group 15-[O-{3-(2-pyridyldithio)-propionyl}]-4,7,10,13-tetraoxapentadecanoic acid tert-butyl ester 29a, followed by its conversion to 15-[O-(3-(2-pyridyldithio)-propionate)-hydroxy]-4,7,10,13-tetraoxapentadecanoic acid 30a.

FIG. 10 shows the preparation of a cytotoxic agent comprising a 15-[N-(3-(L-DM1-dithio)-propionyl]-4,7,10,13-tetraoxapentadecanoic acid-N-hydroxysuccinimide ester linking group 2a.

FIG. 11 shows the preparation of a cytotoxic agent comprising a 15-(L-DM1-dithio)-4,7,10,13-tetraoxapentadecanoic acid-N-hydroxysuccinimide ester linking group 2b.

FIG. 12 shows the preparation of a cytotoxic conjugate 3a using a 15-[N-(3-(L-DM1-dithio)-propionyl]-4,7,10,13-tetraoxapentadecanoic acid-N-hydroxysuccinimide linking group. mAb is mouse anti-Epidermal Growth Factor Receptor monoclonal antibody KS-77.

FIG. 13 shows preferred examples of the four primary embodiments of taxanes of formula T1.

DETAILED DESCRIPTION OF THE INVENTION

Figure 1:
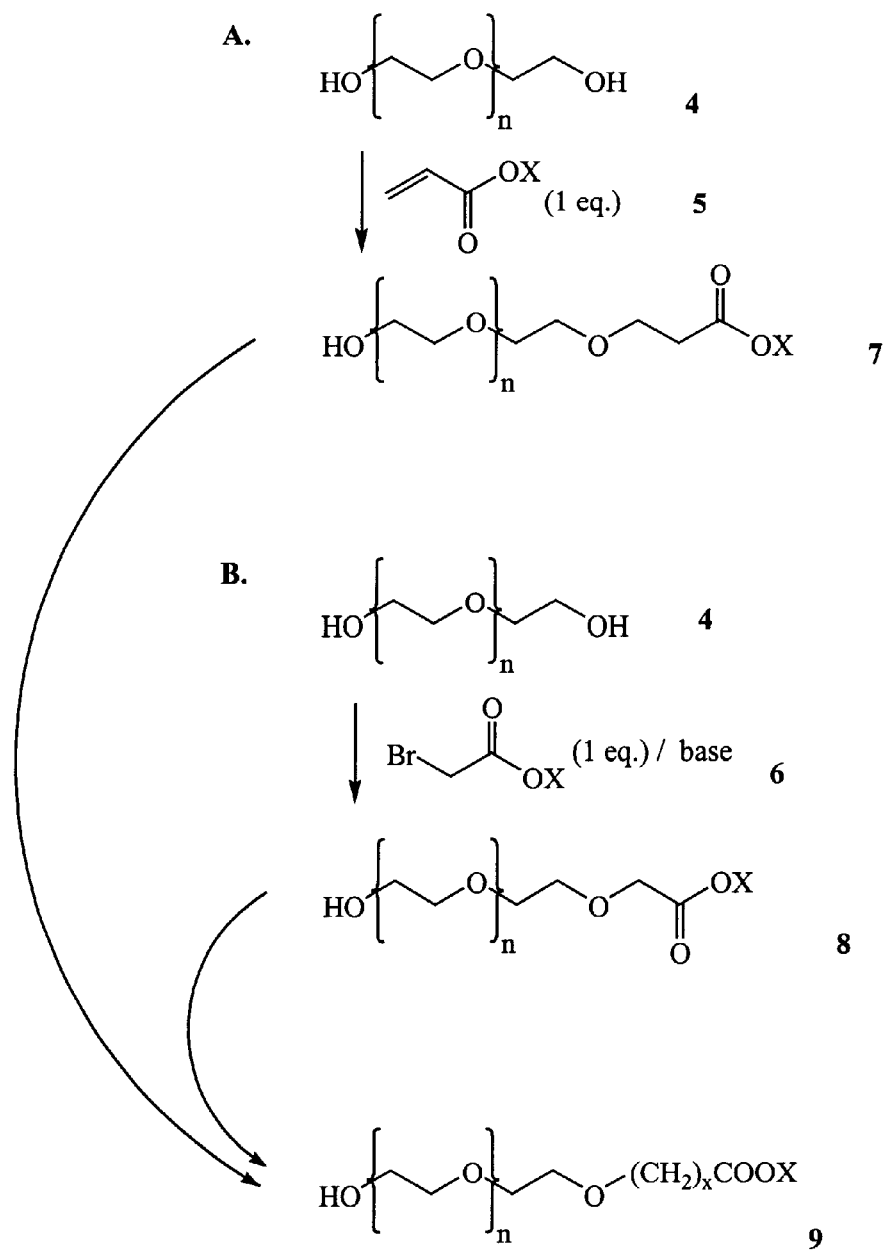
FIG. 1 shows the preparation of carboxy-PEG linkers. Polyethylene glycol 4 is combined with either an acrylate ester 5 or a bromoacetate ester 6 to produce a PEG monoester 7 or 8, respectively. Compounds of PEG 7 and PEG 8 are represented by the consensus formula 9.

Each embodiment of the present invention is based on the use of a hetero-bifunctional polyethylene glycol (PEG) linking group. As discussed herein, the use of PEG as a mono-functional group for attachment to drug molecules has previously been disclosed as a means to convert cytotoxic drugs into prodrugs, improving the half-life and water solubility of the drugs. The PEG linking groups disclosed herein are hetero-bifunctional in that they bind to cytotoxic agents and cell-binding agents at opposite ends of the linkers through a functional sulfhydryl or disulfide group at one end, and an active ester at the other end. Thus, the novel approach disclosed herein is to utilize a PEG linking group containing two separate and unique functional groups to link two different substituents, specifically, cytotoxic agents, including cytotoxic drugs, to cell-binding agents.

PEG Linking Groups

The PEG linking groups of the present invention have a two-fold advantage over other linking groups in that (1) they can be chemically joined to a cytotoxic agent in a non-aqueous solvent via a disulfide bond, thereby surmounting the hydrophobic nature of the agent and making it soluble in both non-aqueous and aqueous solvents, and (2) cytotoxic conjugates produced using the linking groups have greater solubility in water, thereby permitting much greater flexibility in the formulation of pharmaceutical solutions for administration to patients.

The PEG linking groups of the present invention comprise a range of differently sized molecules based on the following formula 1:

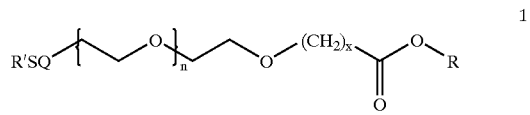

wherein R' is 2-pyridyl, 4-pyridyl, 5-nitro-2-pyridyl, 5-nitro-4-pyridyl, 2-nitrophenyl, 4-nitrophenyl or 2,4-dinitrophenyl;

wherein Q is $R_2COO$—, $R_2R_3NCOO$—, $R_2OCOO$—, $R_2O$—, $R_2CONR_3$—, $R_2R_3N$—, $R_2OCONR_3$—, or S—, wherein:
$R_2$ is $SCR_4R_5R_6$—,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;

wherein n is any integer;

wherein x is 1 or 2; and wherein R is H, a cation to form a salt or a chemical group to form an ester.

In a preferred embodiment, n is an integer of from 0 to 1000. In more preferred embodiments, n is an integer of from 0 to 20, of from 21 to 40, or of from 41 to 1000.

Preferred examples of linear alkyls include methyl, ethyl, propyl, butyl, pentyl and hexyl.

Preferred examples of branched alkyls include isopropyl, isobutyl, sec.-butyl, tert-butyl, isopentyl and 1-ethyl-propyl.

Preferred examples of cyclic alkyls include cyclopropyl, cyclobutyl, cyclopentyl and cyclohexyl.

Each PEG linking group bears a terminal reactive disulfide moiety on one end, separated by the polyethylene glycol chain from either a terminal carboxylic acid moiety or a protected carboxylic acid, preferably in the form of an ester, or a carboxylate salt at the other end. Preferably, the protective ester is methyl, ethyl, phenyl, benzyl or tert.-butyl ester, or other esters that can be readily converted to the corresponding carboxylic acid.

As noted above, in a preferred embodiment n may be any integer of from 0 to 1000 in the PEG linking groups of formula 1. The skilled artisan will understand that the selection of the commercially available forms of PEG for use in each of the synthesis reactions for producing the PEG linking groups can be selected based on achieving the optimal solubility in aqueous solvents, thereby producing the PEG linking groups wherein n is from 0 to 20, n is from 21 to 40, or n is from 41 to 1000.

The synthesis of the PEG linking groups of formula 1 is shown in FIGS. 1, 2, 3A–3D and 4A–4D. Briefly, hetero-bifunctional PEG linking groups may be prepared by first adding sodium metal to anhydrous THF and polyethylene glycol 4 (comprising from 1 to 1000 monomeric units) with stirring. After the sodium completely dissolves, an acrylate ester, such as tert-butyl acrylate 5, is added. The solution is then stirred at room temperature to completion, followed by neutralization with HCl. The solvent is removed, preferably in vacuo, and the residue is suspended in brine, followed by extraction with ethyl acetate. The combined organic layers are washed with brine, then water, dried over sodium sulfate, and the solvent is then removed. The resulting colorless oil is dried under vacuum to yield a compound of formula 7 (FIG. 1).

Alternatively, a bromoacetate ester may be used in place of an acrylate ester. The 33 protocol is the same as above, except that tert-butyl bromoacetate 6 is added in place of tert-butyl acrylate 5. The resulting compound is one of those of formula 8 (FIG. 1).

Together, compounds of formula 7 and formula 8 are encompassed within formula 9 (FIG. 1).

A compound of formula 9 may then be converted to one of a number of hetero-bifunctional PEG linking groups, such as those compounds of formulae 13–15 and 20–40, shown in FIGS. 2, 3A–3D and 4A–4D.

Compounds of the first group are those of formulae 13–15 (FIG. 2). These are produced by reacting compounds of formula 9 with pyridine under cold conditions, followed by slow addition of phosphorus tribromide. The reaction solution is allowed to stir to completion. Water is then poured into the reaction vessel and the organics are extracted into methylene chloride. The combined organic layers are washed with sodium bicarbonate, followed by brine, dried over magnesium sulfate, and the solvent is removed in vacuo. The residue is purified, such as on silica gel using neat ethyl acetate as the eluant, to yield a compound of formula 10 (FIG. 2).

Compounds of formula 10 are then converted to compounds of formula 12 by first preparing a flask charged with Amberlite ion exchange resin IRA-400 (Cl— form) and a solution of sodium hydrosulfide hydrate (NaSH.H$_2$O) dissolved in methanol (MeOH). After allowing the reaction to became cloudy while stirring, a solution of triethylamine hydrochloride in MeOH is added. A solution of a compound of formula 10 in MeOH is then added drop wise and the resulting solution is allowed to stir until reaction completion. The resulting resin is then filtered off and hydrochloric acid is added. The organic layer is separated, and the aqueous layer is extracted into methylene chloride twice. The combined organic layers are dried over anhydrous sodium sulfate, and the solvent removed in vacuo. The resulting residue is purified, such as on silica gel using neat ethyl acetate as the eluant, to yield a thiol compound of formula 12 (FIG. 2).

Alternatively, thiourea followed by aqueous sodium hydroxide (thiourea/OH$^-$) or potassium thiolacetate followed by aqueous sodium hydroxide (KSAc/OH$^-$) may be used in place of sodium hydrosulfide hydrate.

Thiol compounds of formula 12 may alternatively be produced by reacting a compound of formula 9 with tosyl chloride (TsCl) to yield a compound of formula 11. Compounds of formula 11 can then be converted to thiol compounds of formula 12 by reaction with NaSH or thiourea/OH$^-$ or KSAc/OH$^-$, as described for the conversion of compounds of formula 10 to thiol compounds of formula 12.

To a solution of a resulting thiol compound of formula 12, in ethanol, is added 2,2'-dithiodipyridine and glacial acetic acid. The mixture is stirred until completion under an argon atmosphere, and the solvent is evaporated. The residue is purified, such as by silica gel chromatography to yield a compound of formula 13, a hetero-bifunctional PEG linking group (FIG. 2).

If desired, the protective chemical group may be removed from a compound of formula 13 by adding trifluoroacetic acid (TFA) and triethylsilane (Et$_3$SiH) to such a compound, in dichloromethane. After stirring to completion, the mixture is diluted with toluene. The mixture is then evaporated, followed by co-evaporation with toluene and drying in vacuo to yield a compound of formula 14 (FIG. 2).

Finally, a salt of a compound of formula 14 may be produced by the addition of one equivalent of a base, such as sodium or potassium hydroxide to yield a compound of formula 15 (FIG. 2).

Figure 3A:
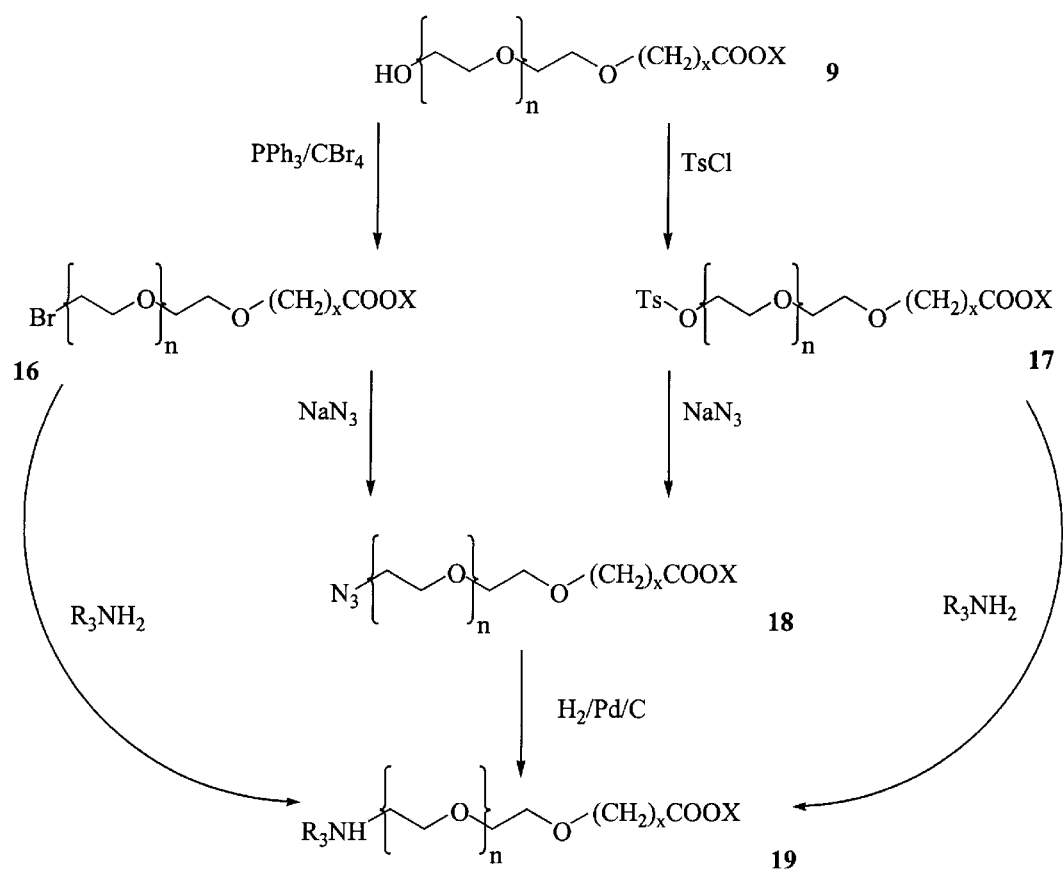
FIGS. 3A–3D show the conversion of carboxy-PEG linkers into ω-aminocarboxy-PEG linkers, followed by their further conversion into hetero-bifunctional PEG linking groups of formulae 20, 23 and 26.
Figure 3B:
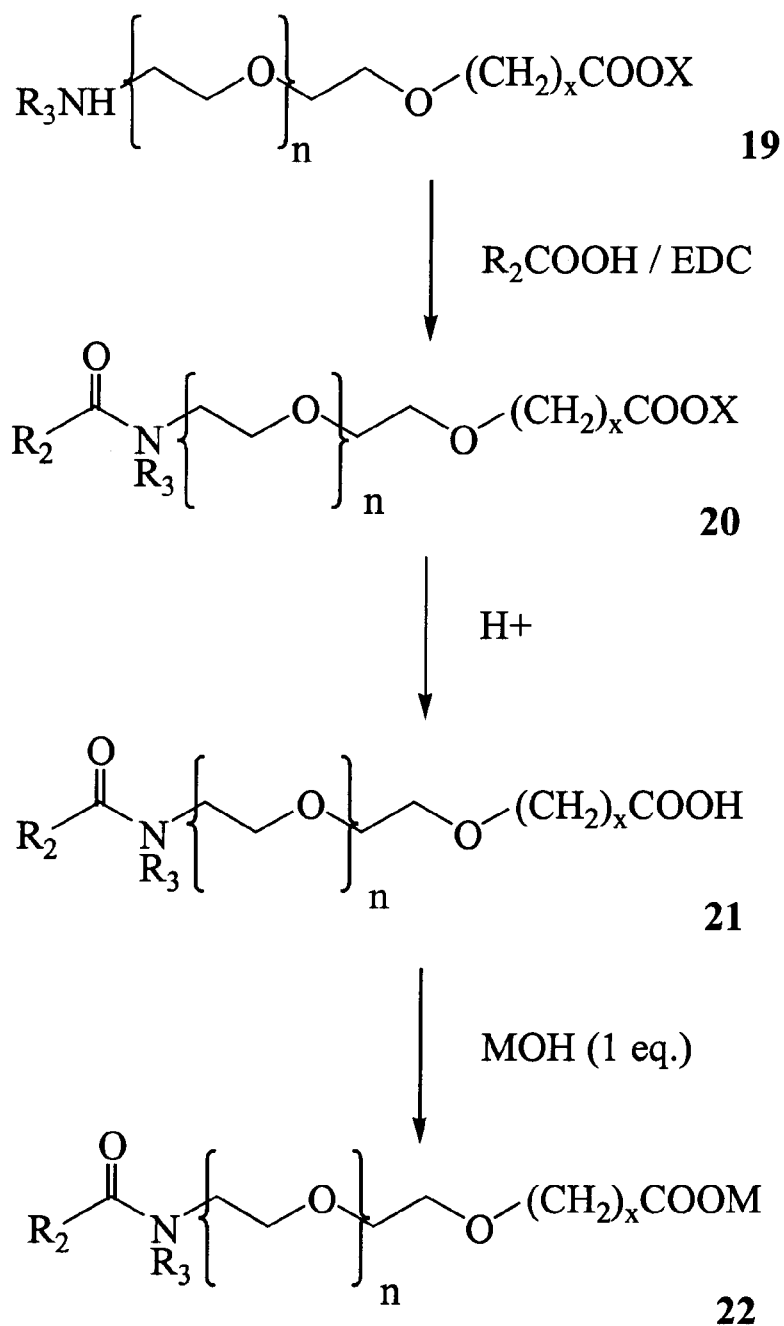
Figure 3C:
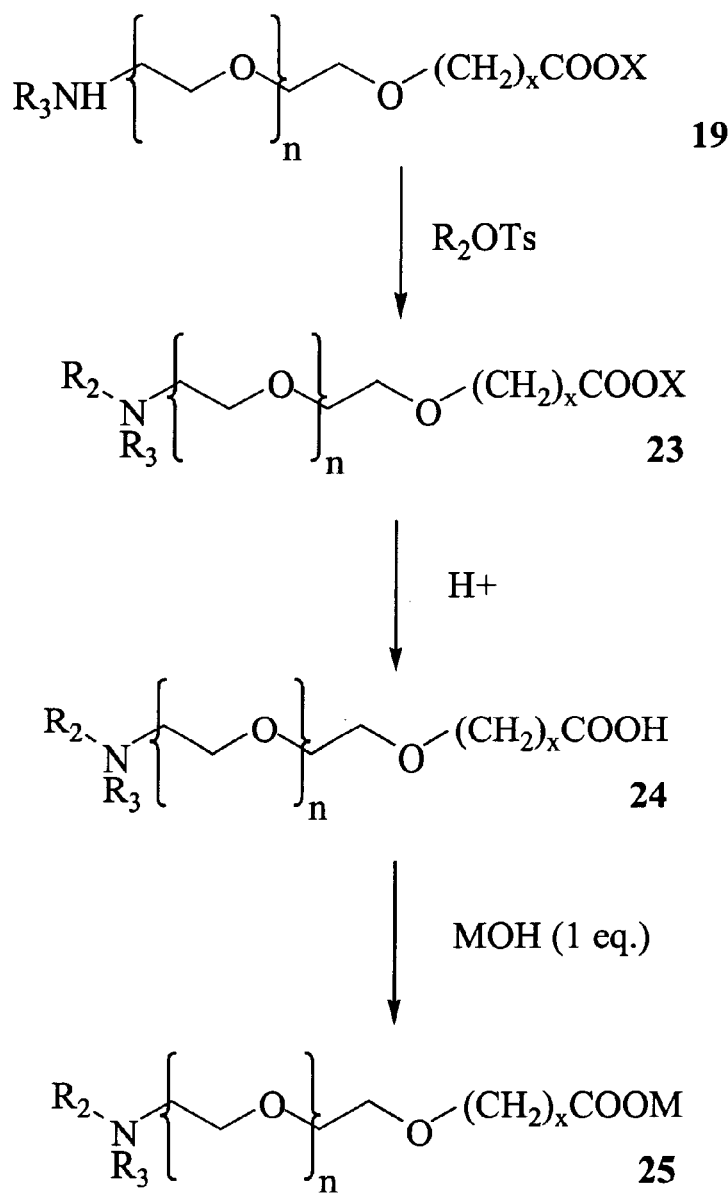
Figure 3D:
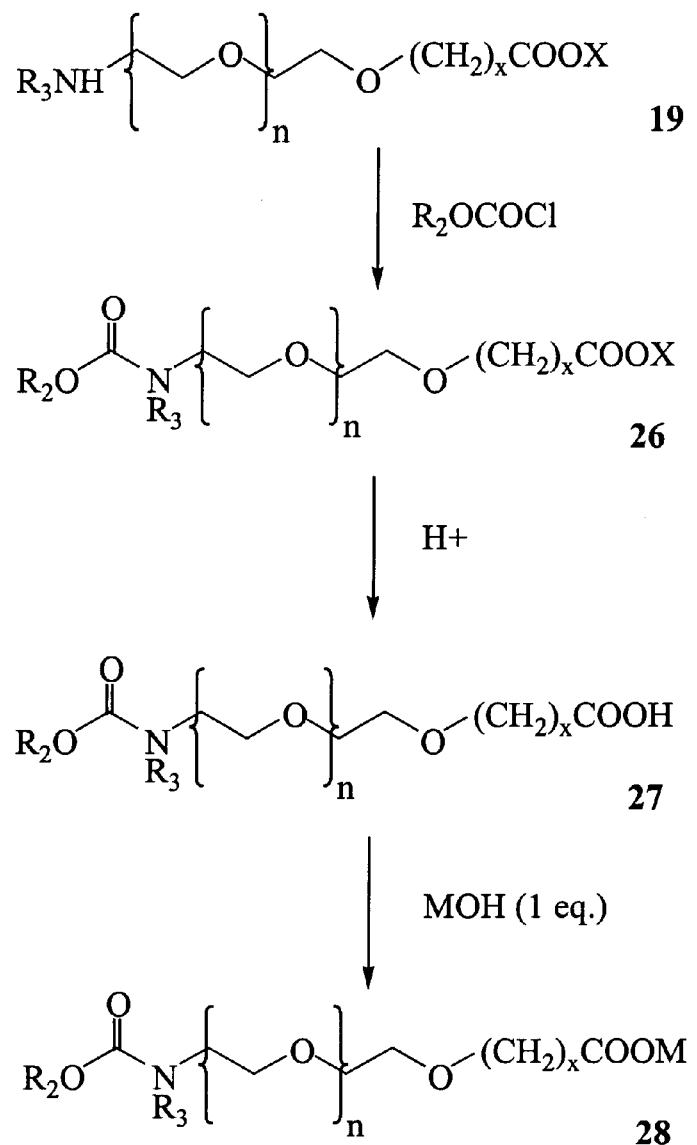

The second group of hetero-bifunctional PEG linking groups into which compounds of formula 9 may be converted are those compounds of formulae 20–28, shown in FIGS. 3B–3D. These are produced by treating a solution of a compound of formula 9, in acetonitrile, with triethylamine. A solution of tosyl chloride in acetonitrile is then added drop wise via an addition funnel over approximately 30 minutes. Thin layer chromatography (TLC) analysis may be used to track completion of the reaction. The triethylamine hydrochloride that forms is filtered off and the solvent is removed. The residue is purified, such as by silica gel by loading the column with 20% ethyl acetate in hexane and eluting with neat ethyl acetate, to yield a compound of formula 17 (FIG. 3A).

Alternatively, a compound of formula 9 may be reacted with triphenylphosphine and carbontetrabromide in methylene chloride to yield compound 10 (FIG. 3A).

Compounds of formulae 10 and 17 are then treated identically to yield a compound of formula 18. To N,N,-dimethylformamide (DMF) is added a compound of formula 10 or 17, and sodium azide, with stirring. The reaction is heated and may be monitored for completion by TLC. The reaction is then cooled and quenched with water. The aqueous layer is separated and extracted into ethyl acetate. The combined organic layers are dried over anhydrous magnesium sulfate, filtered, and the solvent is removed in vacuo. The crude azide of formula 18 may be used without further purification (FIG. 3A).

A compound of formula 18 may then be converted to a compound of formula 19 by dissolving the crude azide in ethanol and adding palladium on carbon catalyst (Pd/C). The system is evacuated under vacuum and placed under 1 atm of hydrogen gas via balloon with vigorous stirring, which is repeated four times to ensure a pure hydrogen atmosphere. The reaction is then stirred overnight at room temperature. TLC may be used to confirm reaction completion. The crude reaction is passed through a short pad of celite, rinsing with ethyl acetate. The solvent is removed and the amine purified, such as on silica gel using a mixture of 15% methanol and 2.5% triethylamine in methylene chloride as the eluant, to yield the desired amine of formula 19 (FIG. 3A).

The amines of formula 19 may then be converted to any of several different hetero-bifunctional PEG linking groups, some of which are represented by formulae 20–68 (FIGS. 3B–3D).

For conversion to linking groups of formulae 20–22, a small flask is charged with an amine of formula 19, 3-(2-pyridyldithio)-propionic acid, 1-(3-dimethylaminopropyl)-3-ethylcarbodiimide hydrochloride (EDC), 4-(dimethylamino)pyridine (DMAP), and methylene chloride. The reaction is stirred at room temperature overnight to completion. The reaction is quenched with ammonium chloride and extracted into ethyl acetate, dried over anhydrous magnesium sulfate, and the solvent is removed in vacuo. The residue is purified, such as on alumina using neat ethyl acetate by TLC monitoring in 5% methanol in methylene chloride, to yield a hetero-bifunctional PEG linking group of formula 20 (FIG. 3B).

If desired, the protective ester group may be removed from a compound of formula 20 by adding an acid in an organic solvent such as trifluoroacetic acid in methylene chloride or anhydrous hydrogen chloride in ethyl acetate. The mixture is then purified by chromatography or crystallization to yield a compound of formula 21 (FIG. 3B).

Finally, a salt of a compound of formula 21 may be produced by the addition of one equivalent of a base such as sodium or potassium hydroxide to yield a compound of formula 22 (FIG. 3B).

For conversion to linking groups of formulae 23–25, an amine of formula 19 is subjected to an alkylation reaction, for example by treating with an alkyl tosylate. The reaction mixture is then purified to yield a hetero-bifunctional PEG linking group of formula 23 (FIG. 3C).

If desired, the protective ester group may be removed from a compound of formula 23 by adding an acid in an organic solvent such as trifluoroacetic acid in methylene chloride or anhydrous hydrogen chloride in ethyl acetate. The mixture is then purified to yield a compound of formula 24 (FIG. 3C).

Finally, a salt of a compound of formula 24 may be produced by the addition of one equivalent of a base such as sodium or potassium hydroxide to yield a compound of formula 25 (FIG. 3C).

For conversion to linking groups of formulae 26–28, an amine of formula 19 is treated with an alkyl chloroformate. The reaction mixture is then purified to yield a hetero-bifunctional PEG linking group of formula 26 (FIG. 3D).

If desired, the protective ester group may be removed from a compound of formula 26 by adding an acid in an organic solvent such as trifluoroacetic acid in methylene chloride or anhydrous hydrogen chloride in ethyl acetate. The mixture is then purified by crystallization or chromatography to yield a compound of formula 27 (FIG. 3D).

Finally, a salt of a compound of formula 27 may be produced by the addition of one equivalent of a base such as sodium or potassium hydroxide to yield a compound of formula 28 (FIG. 3D).

Hetero-bifunctional PEG linking groups may also be prepared from compounds of formula 9 to yield those compounds of formulae 29–40, shown in FIGS. 4A–4D.

Compounds of formulae 29–31 are produced by charging a small flask with alcohol 9, 3-(2-pyridyldithio)-propionic acid, 1-(3-dimethylaminopropyl)-3-ethylcarbodiimide hydrochloride (EDC), 4-(dimethylamino)pyridine (DMAP), and methylene chloride. The reaction is stirred at room temperature overnight to completion. The reaction is quenched with ammonium chloride and extracted into ethyl acetate, dried over anhydrous magnesium sulfate, and the solvent is then removed in vacuo. The residue is purified, such as on silica gel using neat ethyl acetate as the eluant, to yield a hetero-bifunctional PEG linking group of formula 29 (FIG. 4A).

The protective ester group may be removed from a compound of formula 29 by adding such a compound to a small flask in methylene chloride. To this solution is added TFA with stirring until the reaction is complete. Toluene is then added to the reaction mixture and the solvent is removed in vacuo. The residue is purified, such as on silica gel using neat ethyl acetate as the eluant, to yield a compound of formula 30 (FIG. 4A).

Figure 4A:
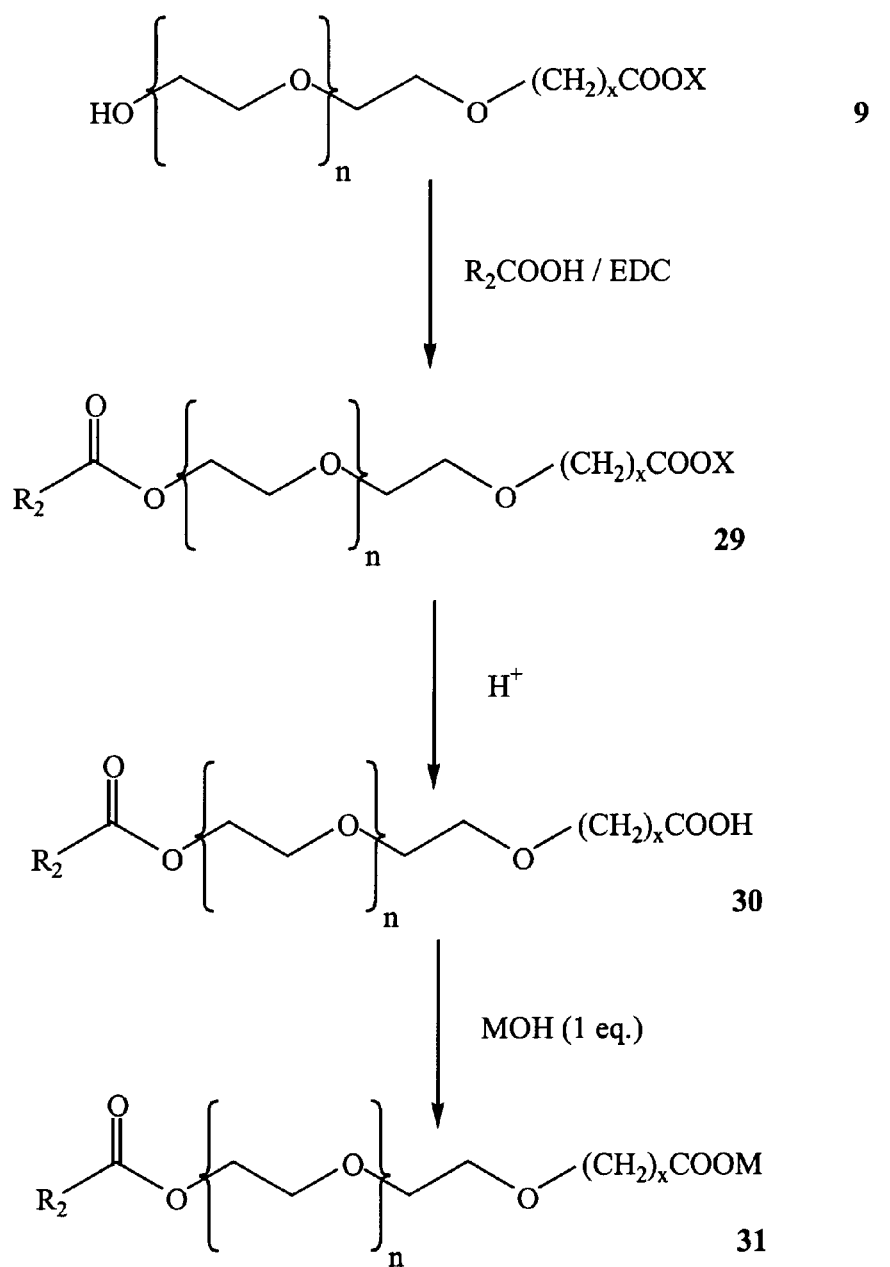

Finally, a salt of a compound of formula 30 may be produced by the addition of one equivalent of a base such as sodium or potassium hydroxide to yield a compound of formula 31 (FIG. 4A).

Compounds of formulae 32–34 are produced by charging a small flask with alcohol 9, phosgene, and ammonia, a primary or secondary amine in a suitable organic solvent such as toluene or methylene chloride. The residue is purified, such as on silica gel using neat ethyl acetate as the eluant, to yield a hetero-bifunctional PEG linking group of formula 32 (FIG. 4B).

The protective ester group may be removed from a compound of formula 32 by reaction with an acid in an organic solvent such as trifluoroacetic acid in methylene chloride or anhydrous hydrogen chloride in ethyl acetate. The residue is purified, such as on silica gel using neat ethyl acetate as the eluant, to yield a compound of formula 33 (FIG. 4B).

A salt of a compound of formula 33 may be produced by the addition of one equivalent of a base such as sodium or potassium hydroxide to yield a compound of formula 34 (FIG. 4B).

Compounds of formulae 35–37 are produced by charging a small flask with alcohol 9, phosgene, and an alcohol. The residue is purified, such as on silica gel using neat ethyl acetate as the eluant, to yield a hetero-bifunctional PEG linking group of formula 35 (FIG. 4C).

The protective ester group may be removed from a compound of formula 35 by reaction with an acid in an organic solvent such as trifluoroacetic acid in methylene chloride or anhydrous hydrogen chloride in ethyl acetate. The residue is purified, such as on silica gel using neat ethyl acetate as the eluant, to yield a compound of formula 36 (FIG. 4C).

Figure 4C:
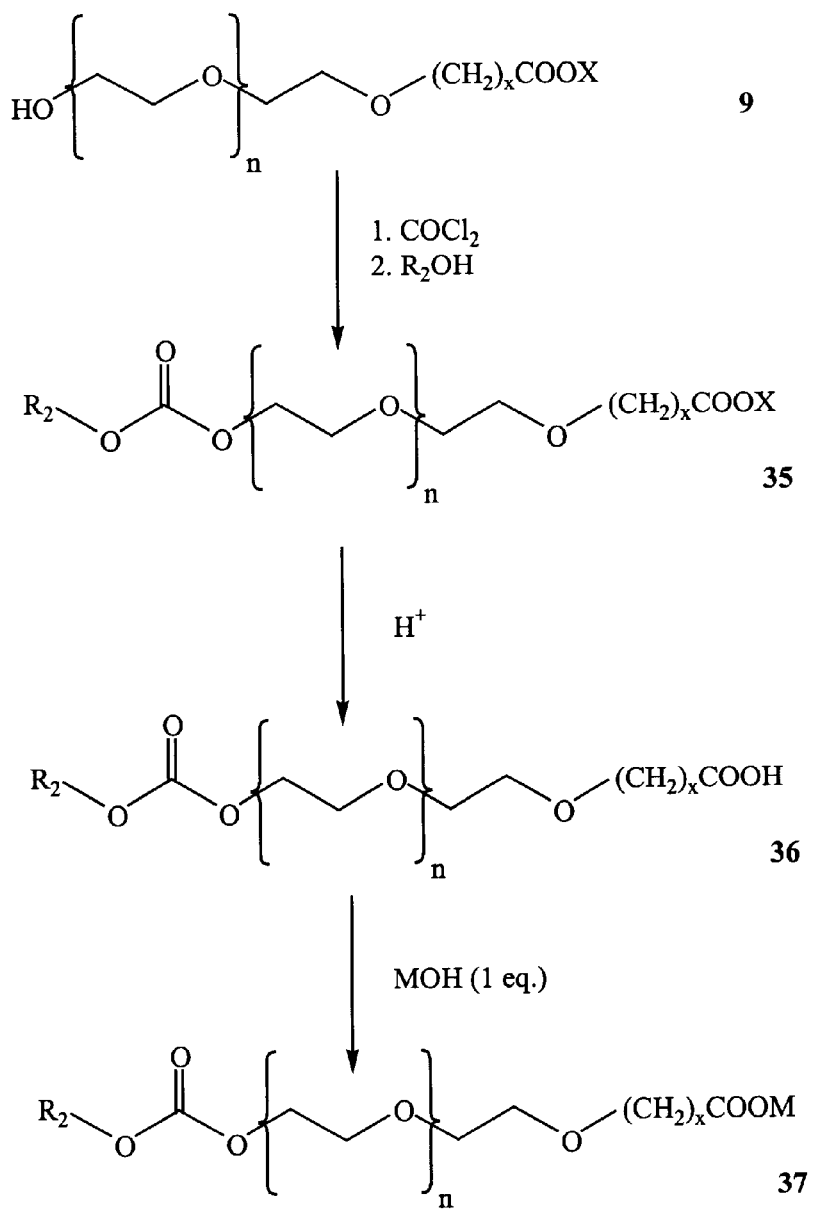

A salt of a compound of formula 36 may be produced by the addition of one equivalent of a base such as sodium or potassium hydroxide to yield a compound of formula 37 (FIG. 4C).

Compounds of formulae 38–40 are produced by charging a small flask with alcohol 9, triphenylphosphine, and carbon tetrabromide in a solvent such as methylene chloride. The residue is purified, such as on silica gel using neat ethyl acetate as the eluant, to yield a hetero-bifunctional PEG linking group of formula 38 (FIG. 4D).

The protective ester group may be removed from a compound of formula 38 by reaction with an acid in an organic solvent such as trifluoroacetic acid in methylene chloride or anhydrous hydrogen chloride in ethyl acetate. The residue is purified, such as on silica gel using neat ethyl acetate as the eluant, to yield a compound of formula 39 (FIG. 4D).

Figure 4D:
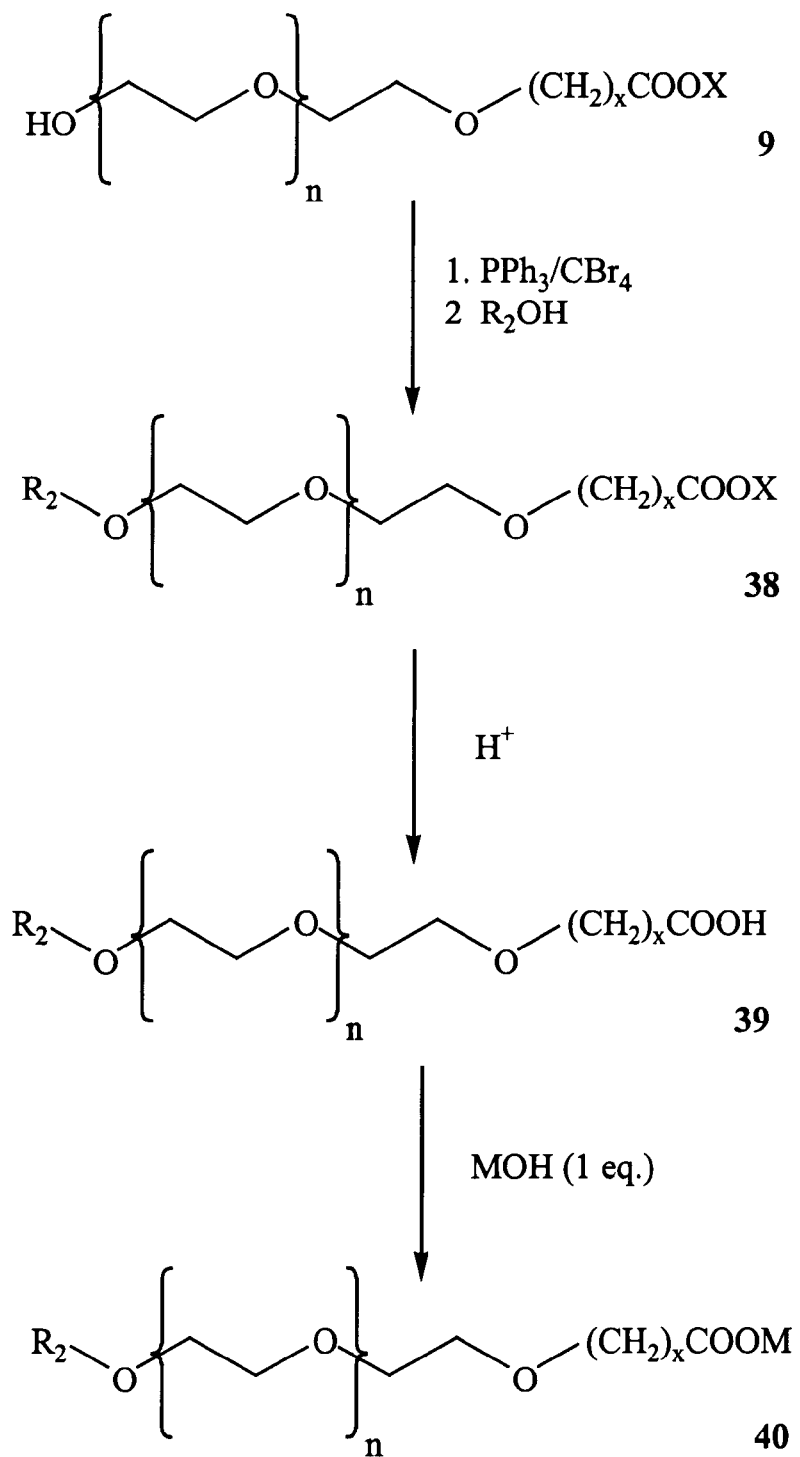

Finally, a salt of a compound of formula 39 may be produced by the addition of one equivalent of a base such as sodium or potassium hydroxide to yield a compound of formula 40 (FIG. 4D).

The hetero-bifunctional PEG linking groups of the present invention include those compounds encompassed by formulae 13–15 and 20–40. Together, these compounds are represented by formula 1.

Cytotoxic Agents Bearing a Reactive PEG Moiety

The cytotoxic agents in the embodiments of the present invention each bears a PEG linking group having a terminal active ester.

Cytotoxic agents bearing PEG linking groups having a terminal active ester (cytotoxic agent-PEG) are illustrated by formula 2.

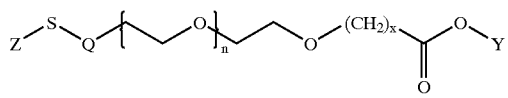

2 wherein Z is a cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl;
wherein n is any integer;
wherein x is 1 or 2; and
wherein Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

In a preferred embodiment, n is an integer of from 0 to 1000. In more preferred embodiments, n is an integer of from 0 to 20, of from 21 to 40, or of from 41 to 1000.

Preferred examples of linear alkyls include methyl, ethyl, propyl, butyl, pentyl and hexyl.

Preferred examples of branched alkyls include isopropyl, isobutyl, sec.-butyl, tert-butyl, isopentyl and 1-ethyl-propyl.

Preferred examples of cyclic alkyls include cyclopropyl, cyclobutyl, cyclopentyl and cyclohexyl.

The cytotoxic agents may be any compound that results in the death of a cell, or induces cell death, or in some manner decreases cell viability, wherein each cytotoxic agent comprises a thiol moiety. Preferred cytotoxic agents are maytansinoids, taxanes, CC-1065 analogues, daunorubicin and doxorubicin analogues, and analogues or derivatives thereof, defined below.

In each linking group, the active ester is one that reacts readily with amino groups in aqueous solvents or buffers. In preferred embodiments, the active ester is a N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl ester.

Figure 5:
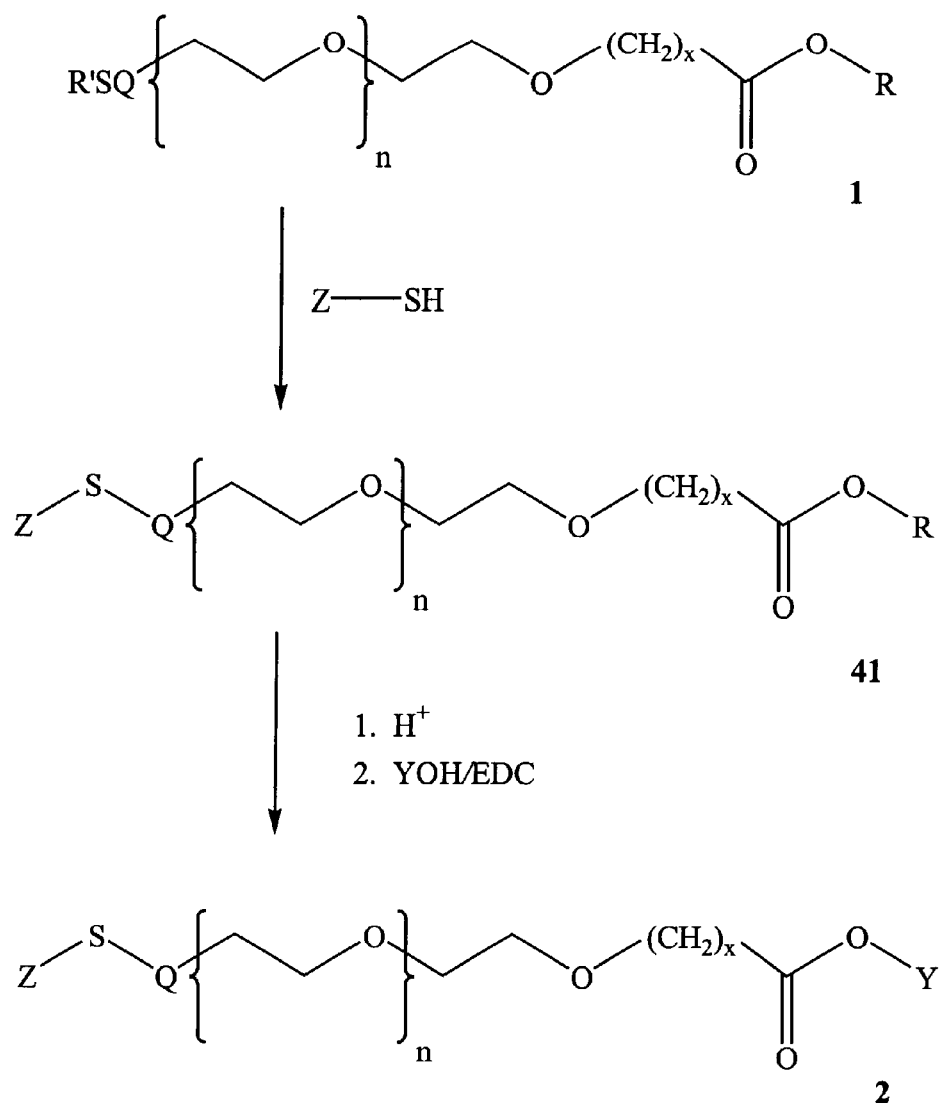
FIG. 5 shows the preparation of cytotoxic agents bearing a reactive PEG moiety. Hetero-bifunctional PEG linking groups 13–15 and 20–40 are represented by consensus formula 1. Hetero-bifunctional PEG linking groups of formula 1 are reacted with a cytotoxic agent bearing a thiol group to produce intermediate compounds of formula 41. Intermediate compounds of formula 41 are then converted to compounds of formula 2, wherein they bear an active terminal ester. R' is 2-pyridyl, 4-pyridyl, 5-nitro-2-pyridyl, 5-nitro-4-pyridyl, 2-nitrophenyl, 4-nitrophenyl or 2,4-dinitrophenyl; Q is $R_2COO$—, $R_2R_3NCOO$—, $R_2OCOO$—, $R_2O$—, $R_2CONR_3$—, $R_2R_3N$—, $R_2OCONR_3$—, or S—, wherein: $R_2$ is $SCR_4R_5R_6$—, $R_4$, $R_5$ and $R_6$ are each H, linear alkyl, cyclic alkyl or branched alkyl, and may be the same or different, and $R_3$ is H or a linear alkyl, cyclic alkyl or branched alkyl; n is any integer; x is 1 or 2; R is H, a cation to form a salt or a chemical group to form an ester; Z is a cytotoxic agent; and Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

The synthesis of cytotoxic agents bearing a reactive PEG moiety of the present invention is illustrated in FIG. 5. A PEG linking group is joined to a cytotoxic agent through disulfide exchange reaction at the terminus containing the reactive disulfide moiety. The resulting disulfide bond serves as the site of release of fully active cytotoxic agents in or near a target cell. Synthesis begins with the reaction of a PEG linking group of formula 1 with a thiol-containing cytotoxic agent, such as maytansinoid, taxane, CC-1065 analogue, daunorubicin analogue and doxorubicin analogue, or analogues or derivatives thereof, wherein each cytotoxic agent contains a thiol moiety. Briefly, a cytotoxic agent and a PEG linking group of formula 1 are dissolved in ethyl alcohol. Potassium phosphate buffer is then added and the solution is stirred under an argon atmosphere until reaction completion. The reaction mixture may then be purified by HPLC. The desired product is collected and the solvent is removed by rotary evaporation under vacuum to yield a compound of formula 41 (FIG. 5).

The PEG linking group joined to the cytotoxic agent can be in at least two forms. One is the PEG linking group of formula 1 where R is a protective chemical group. During the formation of the terminal reactive disulfide moiety at one end of the polyethylene chain, the carboxylic acid at the other end is protected by the chemical group. The protective chemical group may be left on the PEG linking group during the reaction of the linker and a cytotoxic agent. After joining of the PEG linking group with a cytotoxic agent, the protective chemical group can then be replaced with a chemical moiety to generate an active ester for use in joining the cytotoxic agent-PEG linking group to a cell-binding agent.

Another form of PEG linking group that may be joined to a cytotoxic agent is the PEG linking group of formula 1 where R is hydrogen. In this latter version, the protective chemical group is removed from the PEG linking group after the formation of the terminal reactive disulfide moiety (see, e.g., FIG. 4A, conversion of a compound of formula 29 to a compound of formula 30), and before the joining of the PEG linking group with a cytotoxic agent. As above, after completion of the joining reaction, an active ester is formed on the free end of the linking group.

After the disulfide exchange reaction and the formation of a compound of formula 2 occurs, if the PEG linking group of formula 1 wherein R is a hydrogen is used, the terminal carboxylic acid is converted to an active ester. Briefly, a compound of formula 41 is dissolved in methylene chloride to which is added N-hydroxysuccinimide and 1-(3-dimethylaminopropyl)-3-ethylcarbodiimide hydrochloride. The solution is stirred at room temperature until reaction completion and may then be purified by silica chromatography. Solvent is removed under vacuum to yield a cytotoxic agent containing a reactive PEG moiety of formula 2. The resulting compound of formula 2 may be purified by standard chemical means, such as high performance liquid chromatography (HPLC), silica gel chromatography or crystallization.

Alternatively, if the PEG linking group of formula 1 wherein R is a protective chemical group is used, the terminal protective chemical group is removed and replaced with a hydrogen, followed by conversion to an active ester. Briefly, the protective chemical group is removed by acid hydrolysis and the resulting carboxylic acid is converted to an active ester in the usual way. Again, the result is a cytotoxic agent containing a reactive PEG moiety of formula 2.

The cytotoxic agents of the present invention are not limited in their use to the formation of cytotoxic conjugates comprising cytotoxic agents covalently bonded to a cell-binding agent through a PEG linking group, as described above. The skilled artisan will understand that there are a number of uses for which the cytotoxic agents bearing a reactive PEG moiety of the present invention may be used. Such additional uses include, for example, the preparation of affinity resins, which may then be used to isolate the cellular component, e.g., a protein or enzyme which interacts with the cytotoxic agent.

Cytotoxic Conjugates

The cytotoxic conjugates of the present invention each comprises one or more cytotoxic agents covalently bonded to a cell-binding agent through a PEG linking group. Formula 3 illustrates embodiments of the cytotoxic conjugates, illustrating the linkage of one cytotoxic agent through a PEG linking group described above:

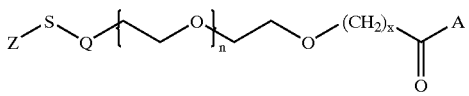

wherein Z is a cytotoxic agent;
wherein Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$,
$R_4$, $R_5$ and $R_6$ are each H, linear alkyl, cyclic alkyl or branched alkyl, and may be the same or different,
$R_3$ is H or a linear alkyl, cyclic alkyl or branched alkyl,
wherein n is any integer;
wherein x is 1 or 2; and
wherein A is a cell-binding agent.

In a preferred embodiment, n is an integer of from 0 to 1000. In more preferred embodiments, n is an integer of from 0 to 20, of from 21 to 40, or of from 41 to 1000.

Preferred examples of linear alkyls include methyl, ethyl, propyl, butyl, pentyl and hexyl.

Preferred examples of branched alkyls include isopropyl, isobutyl, sec.-butyl, tert-butyl, isopentyl and 1-ethyl-propyl.

Preferred examples of cyclic alkyls include cyclopropyl, cyclobutyl, cyclopentyl and cyclohexyl.

More than one cytotoxic agent, linked through a PEG linking group, may be joined to each cell-binding agent molecule.

The cytotoxic agent may be any compound that results in the death of a cell, or induces cell death, or in some manner decreases cell viability, wherein each cytotoxic agent comprises a thiol moiety. Preferred cytotoxic agents are a maytansinoid, taxane, CC-1065 analogue, daunorubicin analogue and doxorubicin analogue, and analogues or derivatives thereof, defined below. The cell-binding agent may be any compound that can bind a cell, either in a specific or non-specific manner. Preferably, the cell-binding agent is a polyclonal antibody, monoclonal antibody, antibody fragment, interferon, lymphokine, hormone, growth factor, vitamin or nutrient-transport molecule, as further discussed below.

Figure 6:
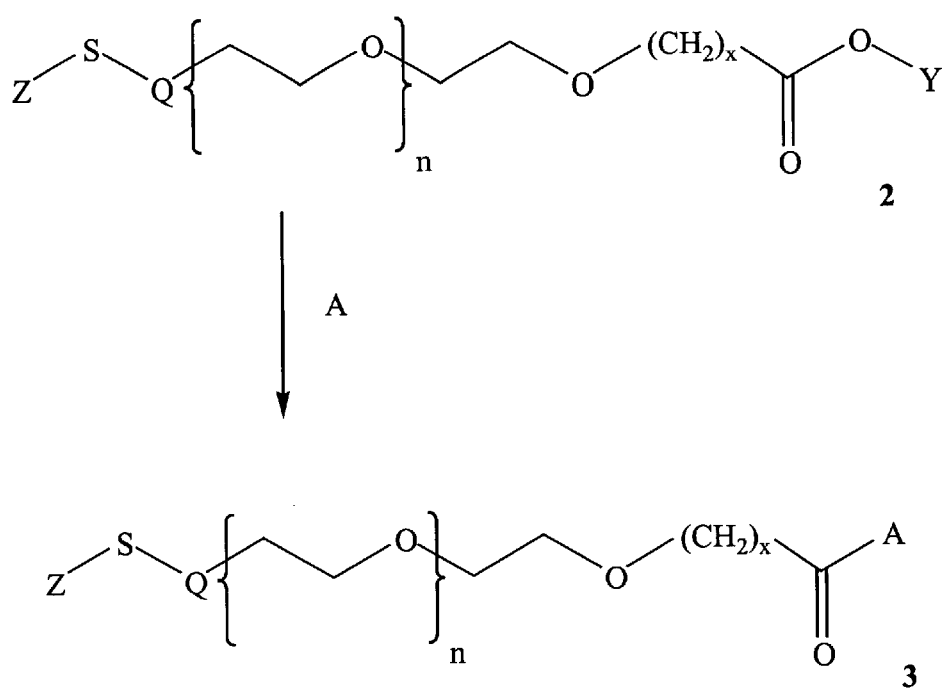
FIG. 6 shows the preparation of cytotoxic conjugates of formula 3. Cytotoxic agents bearing a reactive PEG moiety of formula 2 are combined with a cell-binding agent to yield cytotoxic conjugates of formula 3. Z is a cytotoxic agent; Q is $R_2COO$—, $R_2R_3NCOO$—, $R_2OCOO$—, $R_2O$—, $R_2CONR_3$—, $R_2R_3N$—, $R_2OCONR_3$—, or S—, wherein: $R_2$ is $SCR_4R_5R_6$—, $R_4$, $R_5$ and $R_6$ are each H, linear alkyl, cyclic alkyl or branched alkyl, and may be the same or different, and $R_3$ is H or a linear alkyl, cyclic alkyl or branched alkyl; n is any integer; x is 1 or 2; Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl; and A is a cell-binding agent.

The synthesis of representative cytotoxic conjugates of the present invention is illustrated in FIG. 6. Synthesis begins with the reaction of one or more of the cytotoxic agents bearing a reactive PEG moiety 2 with a cell-binding agent, resulting in displacement of the terminal active ester of each reactive PEG moiety by an amino acid residue of the cell-binding agent, to yield a cytotoxic conjugate comprising one or more cytotoxic agents covalently bonded to a cell-binding agent through a PEG linking group. For example, a compound of formula 2 is dissolved in anhydrous ethanol to obtain a stock concentration. A solution of a cell binding agent, such as a monoclonal antibody, in potassium phosphate buffer, containing NaCl and ethylenediaminetetraacetic acid is then treated with a molar excess of the compound of formula 2. The reaction mixture is incubated at ambient temperature for approximately 2 hours. The cytotoxic conjugate may then be purified by size-exclusion chromatography over a Sephadex G25 column that had been previously equilibrated in phosphate-buffered saline to remove unreacted compound 2 and other low molecular weight materials.

Importantly, the cell-binding agent does not need to be modified in any way prior to its joining with each cytotoxic agent-PEG. The cell-binding agent need only to possess an amino group.

The cytotoxic conjugate may be purified by standard biochemical means, such as gel filtration on a Sephadex G25 or Sephacryl S 300 column, or by dialysis as previously described.

Maytansinoids

Maytansinoids that can be used in the present invention are well known in the art and can be isolated from natural sources according to known methods or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring include:

(1) C-19-dechloro (U.S. Pat. No. 4,256,746) (prepared by LAH reduction of ansamytocin P2);

(2) C-20-hydroxy (or C-20-demethyl) +/−C-19-dechloro (U.S. Pat. Nos. 4,361,650 and 4,307,016) (prepared by demethylation using Streptomyces or Actinomyces or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl (demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from Nocardia);

(4) C-15-hydroxy/acyloxy (U.S. Pat. No. 4,364,866) (prepared by the conversion of maytansinol by Streptomyces);

(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322,348) (prepared by the demethylation of maytansinol by Streptomyces); and (7) 4,5-deoxy (U.S. Pat. No. 4,371,533) (prepared by the titanium trichloride/LAH reduction of maytansinol).

Maytansinoids used in the present invention contain a thiol moiety. Such thiol-containing maytansinoids are covalently bonded to a PEG linking group via disulfide exchange between the thiol of the maytansinoid and the disulfide substituent of the PEG linking group. The synthesis of thiol-containing maytansinoids used in the present invention is fully disclosed in U.S. Patent Nos. 5,208,020 and 5,416,064, incorporated herein in their entirety.

Addition of a PEG linking group to a thiol-containing maytansinoid can occur at more than one position. For example, maytansinoids with a thiol moiety at the C-3 position, the C-14 position, the C-15 position or the C-20 position are all expected to be useful. The C-3 position is preferred and the C-3 position of maytansinol is especially preferred. Also preferred is an N-methyl-alanine-containing C-3 thiol moiety maytansinoid, and an N-methyl-cysteine-containing C-3 thiol moiety maytansinoid, and analogues of each.

Specific examples of N-methyl-alanine-containing C-3 thiol moiety maytansinoid derivatives useful in the present invention are represented by the formulae M1, M2, M3 and M6.

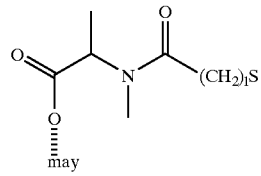

M1 wherein:
l is an integer of from 1 to 10; and
may is a maytansinoid.

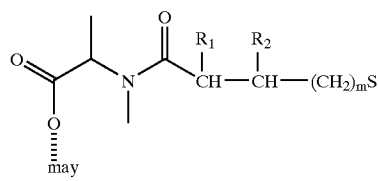

M2 wherein:
$R_1$ and $R_2$ are H, $CH_3$ or $CH_2CH_3$, and may be the same or different;
m is 0, 1, 2 or 3; and
may is a maytansinoid.

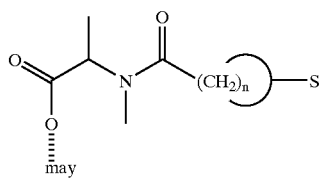

M3 wherein:
n is an integer of from 3 to 8; and
may is a maytansinoid.

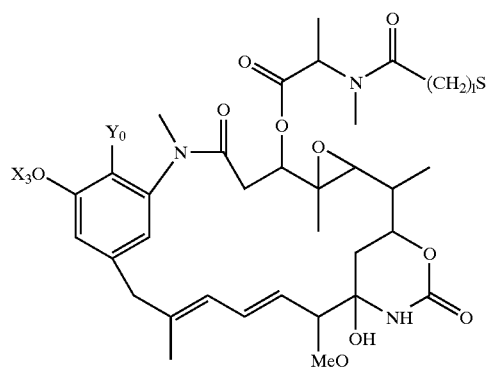

M6 wherein:
l is 1, 2 or 3;
$Y_0$ is Cl or H; and
$X_3$ is H or $CH_3$.

Specific examples of N-methyl-cysteine-containing C-3 thiol moiety maytansinoid derivatives useful in the present invention are represented by the formulae M4 and M5.

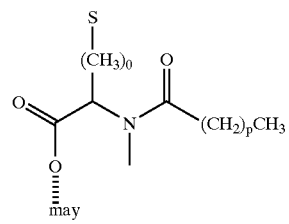

M4 wherein:
o is 1, 2 or 3;
p is an integer of 0 to 10; and
may is a maytansinoid.

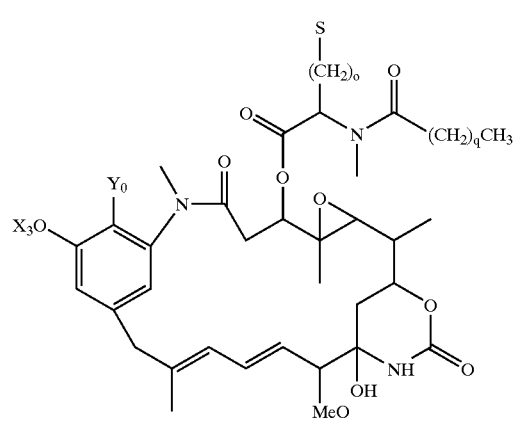

M5 wherein:
o is 1, 2 or 3;
q is an integer of from 0 to 10;
$Y_0$ is Cl or H; and
$X_3$ is H or $CH_3$.

Taxanes

The cytotoxic agent, comprising the cytotoxic agent bearing a reactive PEG moiety and the cytotoxic conjugates according to the present invention, may also be a taxane.

Taxanes that can be used in the present invention can be modified to contain a thiol moiety, to which a PEG linking group is covalently bonded via disulfide exchange between the thiol and the disulfide substituent of the PEG linking group.

The taxanes useful in the present invention have the formula T1 shown below:

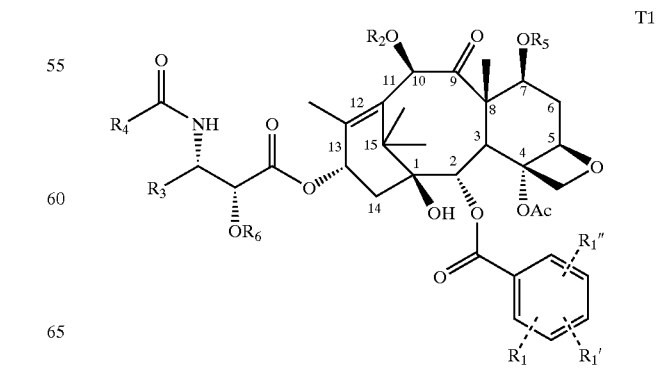

T1

These novel taxanes can be divided into four primary embodiments, taxanes of compounds (1), (2), (3) and (4). Preferred examples of the four embodiments are shown in FIG. 13.

In embodiments (1) to (4), $R_1$ is an electron withdrawing group, such as F, $NO_2$, CN, Cl, $CHF_2$, or $CF_3$ or an electron donating group such as $-OCH_3$, $-OCH_2CH_3$, $-NR_7R_8$, $-OR_9$, where $R_7$ and $R_8$ are the same or different and are linear, branched, or cyclic alkyl groups having 1 to 10 carbon atoms or simple or substituted aryl having 1 to 10 carbon atoms. Preferably the number of carbon atoms for $R_7$ and $R_8$ is 1 to 4. Also, preferably $R_7$ and $R_8$ are the same. Examples of preferred $-NR_7R_8$ groups include dimethyl amino, diethyl amino, dipropyl amino, and dibutyl amino, where the butyl moiety is any of primary, secondary, tertiary or isobutyl. $R_9$ is linear, branched or cyclic alkyl having 1 to 10 carbon atoms.

$R_1$ can also be H.

$R_1'$ and $R_1''$ are the same or different and are H, an electron withdrawing group, or an electron donating group.

$R_1$ is preferably $OCH_3$, F, $NO_2$, or $CF_3$.

Preferably, $R_1$ is in the meta position and $R_1'$ and $R_1''$ are H or $OCH_3$.

In embodiments (1), (2) and (4), $R_2$ is heterocyclic, a linear, branched, or cyclic ester having from 1 to 10 carbon atoms or heterocyclic, a linear, branched, or cyclic ether having from 1 to 10 carbon atoms or a carbamate of the formula $-CONR_{10}R_{11}$, wherein $R_{10}$ and $R_{11}$ are the same or different and are H, linear, branched, or cyclic alkyl having 1 to 10 atoms or simple or substituted aryl having 1 to 10 carbon atoms. For esters, preferred examples include $-COCH_2CH_3$ and $-COCH_2CH_2CH_3$. For ethers, preferred examples include $-CH_2CH_3$ and $-CH_2CH_2CH_3$. For carbamates, preferred examples include $-CONHCH_2CH_3$, $-CONHCH_2CH_2CH_3$, $-CO$-morpholino, $-CO$-piperazino, $-CO$-piperidino, or $-CO$-N-methylpiperazino.

In embodiment (3), $R_2$ is a thiol-containing moiety.

In embodiments (1), (3) and (4), $R_3$ is aryl, or is linear, branched or cyclic alkyl having 1 to 10 carbon atoms, preferably $-CH_2CH(CH_3)_2$.

In embodiment (2), $R_3$ is $-CH=C(CH_3)_2$.

In all embodiments, $R_4$ is $-OC(CH_3)_3$ or $-C_6H_5$.

In embodiments (1) and (2), $R_5$ is a thiol-containing moiety and $R_6$ is H or has the same definition as above for $R_2$ for embodiments (1), (2) and (4).

In embodiment (3), $R_5$ is H or has the same definition as above for $R_2$ for embodiments (1), (2) and (4).

In embodiment (3), $R_6$ is H or has the same definition as above for $R_2$ for embodiments (1), (2) and (4).

In embodiment (4), $R_5$ is H or has the same definition as above for $R_2$ for embodiments (1), (2) and (4) and $R_6$ is a thiol moiety.

The preferred positions for introduction of the thiol-containing moiety are $R_2$ and $R_5$, with $R_2$ being the most preferred.

The side chain carrying the thiol moiety can be linear or branched, aromatic or heterocyclic. One of ordinary skill in the art can readily identify suitable side chains. Specific examples of thiol moieties include $-(CH_2)_nS$, $-CO(CH_2)_nS$, $-(CH_2)_nCH(CH_3)S$, $-CO(CH_2)_nCH(CH_3)S$, $-(CH_2)_nC(CH_3)_2S$, $-CO(CH_2)_nC(CH_3)_2S$, $-CONR_{12}(CH_2)_nS$, $-CONR_{12}(CH_2)_nCH(CH_3)S$, or $-CONR_{12}(CH_2)_nC(CH_3)_2S$, $-CO$-morpholino-XS, $-CO$-piperazino-XS, $-CO$-piperidino-XS, and $-CO$-N-methylpiperazino-XS wherein X is a linear alkyl or branched alkyl having 1–10 carbon atoms.

$R_{12}$ is a linear alkyl, branched alkyl or cyclic alkyl having 1 to 10 carbon atoms, or simple or substituted aryl having from 1 to 10 carbon atoms or heterocyclic, and can be H, and n is an integer of 0 to 10.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

Examples of cyclic alkyls include cyclopropyl, cyclobutyl, cyclopentyl and cyclohexyl.

Examples of simple aryls include phenyl and naphthyl.

Examples of substituted aryls include aryls such as those described above substituted with alkyl groups, with halogens, such as Cl, Br, F, nitro groups, amino groups, sulfonic acid groups, carboxylic acid groups, hydroxy groups or alkoxy groups.

Examples of heterocyclics are compounds wherein the heteroatoms are selected from O, N, and S, and include morpholino, piperidino, piperazino, N-methylpiperazino, pyrrollyl, pyridyl, furyl and thiophene.

The taxanes having a thiol moiety can be synthesized according to known methods. The starting material for the synthesis is the commercially available 10-deacetylbaccatin III. The chemistry to introduce various substituents is described in several publications (Ojima et al, *J. Med. Chem.* 39:3889–3896 (1996); Ojima et al., *J. Med. Chem.* 40:267–278 (1997); Ojima et al., *Proc. Natl. Acad. Sci.*, 96:42564261 (1999), U.S. Pat. No. 5,475,011 and U.S. Pat. No. 5,811,452).

The substituent $R_1$ on the phenyl ring and the position of the substituent $R_1$ can be varied until a compound of the desired toxicity is obtained. Furthermore, the degree of substitution on the phenyl ring can be varied to achieve a desired toxicity. That is, the phenyl ring can have one or more substituents (e.g., mono-, di-, or tri-substitution of the phenyl ring) which provide another means for achieving a desired toxicity. One of ordinary skill in the art can determine the appropriate chemical moiety for $R_1$ and the appropriate position for $R_1$ using only routine experimentation.

For example, electron withdrawing groups at the meta position increase the cytotoxic potency, while substitution at the para position is not expected to increase the potency as compared to the parent taxane. Typically, a few representative taxanes with substituents at the different positions (ortho, meta and para) will be initially prepared and evaluated for in vitro cytotoxicity.

The thiol moiety can be introduced at one of the positions where a hydroxyl group already exists. The chemistry to protect the various hydroxyl groups, while reacting the desired one, has been described previously (see, for example, the references cited supra). The substituent is introduced by simply converting the free hydroxyl group to a disulfide-containing ether, a disulfide-containing ester, or a disulfide-containing carbamate. This transformation is achieved as follows. The desired hydroxyl group is deprotonated by treatment with the commercially-available reagent lithium hexamethyldisilazane (1.2 equivalents) in tetrahydrofuran at −40° C as described in Ojima et al. (1999), supra. The resulting alkoxide anion is then reacted with an excess of a dihalo compound, such as dibromoethane, to give a halo ether. Displacement of the halogen with a thiol (by reaction with potassium thioacetate and treatment with mild base or hydroxylamine) will provide the desired thiol-containing taxane.

Alternatively, the desired hydroxyl group can be esterified directly by reaction with an acyl halide, such as 3-bromopropionyl chloride, to give a bromo ester. Displacement of the bromo group by treatment with potassium thioacetate and further processing as described above will provide the thiol-containing taxane ester.

CC-1065 Analogues

The cytotoxic agent, comprising the cytotoxic agent bearing a reactive PEG moiety and the cytotoxic conjugates according to the present invention, may also be a CC-1065 analogue.

According to the present invention, the CC-1065 analogues must contain an A subunit and a B or a B-C subunit. The A subunits are CPI (cyclopropapyrroloindole unit) in its natural closed cyclopropyl form or in its open chloromethyl form, or the closely related CBI unit (cyclopropylbenzindole unit) in the closed cyclopropyl form or the open chloromethyl form. The B and C subunits of CC-1065 analogues are very similar and are 2-carboxy-indole and a 2-carboxy-benzofuran derivatives. For activity, the analogues of CC-1065 need at least one such 2-carboxy-indole subunit or 2-carboxy-benzofuran subunit, although two subunits (i.e., B-C) render the analogue more potent. As is obvious from the natural CC-1065 and from the analogues published (e.g., Warpehoski et al, *J. Med. Chem.* 31:590–603 (1988)), the B and C subunits can also carry different substituents at different positions on the indole or benzofuran rings.

In order to join CC-1065 analogues to a PEG linking group, the analogues are first modified to include a thiol moiety. A PEG linking group may then be covalently bonded to the CC-1065 analogue via disulfide exchange between the thiol and the disulfide substituent of the PEG linking group.

CC-1065 analogues containing a thiol moiety can be any of the following A subunits of the formulae A-1 {CPI (Cyclopropyl form)}, A-2 {CPI (Chloromethyl form)}, A-3 {CBI (Cyclopropyl form)}, and A-4 {CBI (Chloromethyl form)} covalently linked via an amide bond from the secondary amino group of the pyrrole moiety of the A subunit to the C-2 carboxy group of either a B subunit of the formula F-1 or a B-C subunit of the formulae F-3 or F-7.

A Subunits

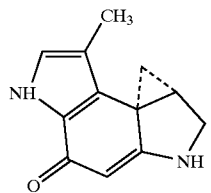
A-1

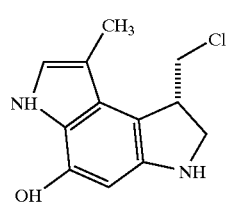
A-2

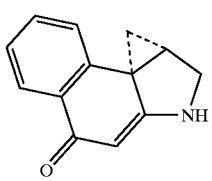
A-3

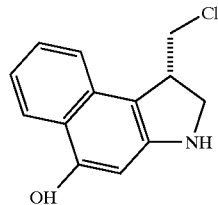
A-4

B and Covalently Bound B and C Subunits

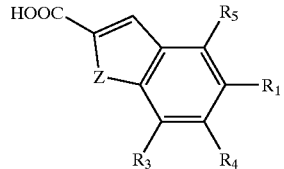
F-1

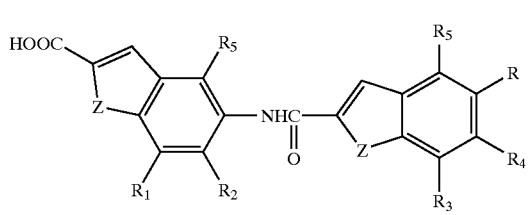
F-3

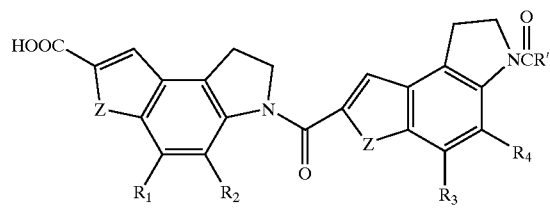
F-7 wherein each Z may be the same or different and may be O or NH; and wherein, in Formula F-1 $R_4$ is a thiol moiety, in Formula F-3 one of R or $R_4$ is a thiol moiety, in Formula F-7 one of R' or $R_4$ is a thiol-containing moiety; when R or R' is a thiol moiety, then $R_1$ to $R_6$, which maybe the same or different, are hydrogen, $C_1$–$C_3$ linear alkyl, methoxy, hydroxyl, primary amino, secondary amino, tertiary amino, or amido; and when $R_4$ is a thiol moiety, R, $R_1$, $R_2$, $R_3$, $R_4$, $R_5$ and $R_6$, which may be the same or different, are hydrogen, $C_1$–$C_3$ linear alkyl, methoxy, hydroxyl, primary amino, secondary amino, tertiary amino, or amido, and R' is $NH_2$, alkyl, O-alkyl, primary amino, secondary amino, tertiary amino, or amido.

In a preferred embodiment, R and R' are thiol moieties and $R_1$ and $R_2$ are each hydrogen. In another preferred embodiment, R and R' are thiol moieties and $R_1$ to $R_6$ are each hydrogen.

In an especially preferred embodiment, R or $R_4$ is —NHCO(CH$_2$)$_l$S, —NHCOC$_6$H$_4$(CH$_2$)$_l$S, or —O(CH$_2$)$_l$S, and R' is —(CH$_2$)$_l$S, —NH(CH$_2$)$_l$S or —O(CH$_2$)$_l$S wherein l is an integer of 1 to 10.

Examples of primary amines include methyl amine, ethyl amine and isopropyl amine.

Examples of secondary amines include dimethyl amine, diethylamine and ethylpropyl amine.

Examples of tertiary amines include trimethyl amine, triethyl amine, and ethyl-isopropyl-methyl amine.

Examples of amido groups include N-methylacetamido, N-methyl-propionamido, N-acetamido, and N-propionamido.

Examples of alkyl represented by R', when R' is not a linking group, include $C_1$–$C_5$ linear or branched alkyl.

Examples of O-alkyl represented by R' when R' is not a linking group, include compounds where the alkyl moiety is a $C_1$–$C_5$ linear or branched alkyl.

The above-described CC-1065 analogues may be isolated from natural sources and methods for their preparation, involving subsequent modification, synthetic preparation, or a combination of both, are well-described (see, e.g., U.S. Pat. Nos. 5,475,092, 5,585,499 and 5,846,545).

Daunorubicin/Doxorubicin Analogues

The cytotoxic agent, comprising the cytotoxic agent bearing a reactive PEG moiety and the cytotoxic conjugates according to the present invention, may also be a daunorubicin analogue or a doxorubicin analogue.

The daunorubicin and doxorubicin analogues of the present invention can be modified to comprise a thiol moiety. A PEG linking group may then be covalently bonded to the daunorubicin/doxorubicin analogues via disulfide exchange between the thiol and the disulfide substituent of the PEG linking group.

The modified doxorubicin/daunorubicin analogues useful in the present invention have the formula D1 shown below:

D1 wherein,

X is H or OH;

Y is O or $NR_2$, wherein $R_2$ is linear or branched alkyl having 1 to 5 carbon atoms;

R is a thiol moiety, H, or liner or branched alkyl having 1 to 5 carbon atoms; and R' is a thiol moiety, H, or —$OR_1$, wherein $R_1$ is linear or branched alkyl having 1 to 5 carbon atoms;

provided that R and R' are not thiol moieties at the same time.

In a preferred embodiment, $NR_2$ is $NCH_3$. In another preferred embodiment, R' is —O.

In an especially preferred embodiment, the thiol moiety is —$(CH_2)_nS$, —$O(CH_2)_nS$, —$(CH_2)_nCH(CH_3)S$, —$O(CH_2)_nCH(CH_3)S$, —$(CH_2)_nC(CH_3)_2S$, or —$O(CH_2)_nC(CH_3)_2S$, wherein n is an integer of 0 to 10.

Examples of the linear or branched alkyl having 1 to 5 carbon atoms, represented by R, $R_1$, and $R_2$, include methyl, ethyl, n-propyl, isopropyl, n-butyl, isobutyl, sec.-butyl, tert.-butyl, and pentyl, in any of its eight isomeric arrangements.

$R_1$ and $R_2$ preferably are methyl.

Examples of linear alkyls include methyl, ethyl, propyl, butyl, pentyl and hexyl.

Examples of branched alkyls include isopropyl, isobutyl, sec.-butyl, tert.-butyl, isopentyl and 1-ethyl-propyl.

When either R or R' is not a linking group, the substituent in that position can be varied until a compound of the desired toxicity is obtained. High toxicity is defined as having an $IC_{50}$ towards cultured cancer cells in the range of $1\times10^{-12}$ to $1\times10^{-9}$ M, upon a 72 hour exposure time. Representative examples of substituents are H, alkyl, and O-alkyl, as described above. One of ordinary skill in the art can determine the appropriate chemical moiety for R and R' using only routine experimentation.

For example, methyl and methoxy substituents are expected to increase the cytotoxic potency, while a hydrogen is not expected to increase the potency as compared to the parent doxorubicin or daunorubicin analogues. Typically a few representative modified doxorubicin or daunorubicin analogues with substituents at the different positions will be initially prepared and evaluated for in vitro cytotoxicity.

The modified doxorubicin/daunorubicin analogues of the present invention, which have a thiol moiety are described in WO 01/38318. The modified doxorubicin/daunorubicin analogues can be synthesized according to known methods (see, e.g., U.S. Pat. No. 5,146,064).

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

Cell-binding Agents

The cell-binding agent that comprises each of the cytotoxic conjugates of the present invention may be of any kind presently known, or that become known, and include peptides and non-peptides. The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

More specific examples of cell-binding agents that can be used include:

resurfaced antibodies (U.S. Pat. No. 5,639,641);

fragments of antibodies such as sFv, Fab, Fab', and F(ab')$_2$ (Parham, *J. Immunol.* 131:2895–2902 (1983); Spring et al, *J. Immunol.* 113:470–478 (1974); Nisonoff et al, *Arch. Biochem. Biophys.* 89:230–244 (1960));

interferons (e.g. α, β, γ);

lymphokines such as IL-2, IL-3, IL-4, IL-6;

hormones such as insulin, TRH (thyrotropin releasing hormones), MSH (melanocyte-stimulating hormone), steroid hormones, such as androgens and estrogens;

vitamins such as folic acid;

growth factors and colony-stimulating factors such as EGF, TGF-α, G-CSF, M-CSF and GM-CSF (Burgess, *Immunology Today* 5:155–158 (1984)); and transferrin (O'Keefe et al, *J. Biol. Chem.* 260:932–937 (1985)).

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of sFv (single chain variable region), specifically human sFv (see, e.g., Griffiths et al, U.S. Pat. No. 5,885,793; McCafferty et al, WO 92/01047; Liming et al, WO 99/06587.)

Selection of the appropriate cell-binding agent is a matter of choice that depends upon the particular cell population that is to be targeted, but in general monoclonal antibodies are preferred, if an appropriate one is available.

For example, the monoclonal antibody My9 is a murine $IgG_{2a}$ antibody that is specific for the CD33 antigen found on Acute Myeloid Leukemia (AML) cells (Roy et al. *Blood* 77:2404–2412 (1991)) and can be used to treat AML patients. Similarly, the monoclonal antibody anti-B4 is a murine $IgG_1$, that binds to the CD19 antigen on B cells (Nadler et al, *J. Immunol.* 131:244–250 (1983)) and can be used if the target cells are B cells or diseased cells that express this antigen such as in non-Hodgkin's lymphoma or chronic lymphoblastic leukemia. Similarly, the antibody N901 is a murine monoclonal $IgG_1$ antibody that binds to CD56 found on small cell lung carcinoma cells and on cells of other tumors of neuroendocrine origin (Roy et al. *J. Nat. Cancer Inst.* 88:1136–1145 (1996)).

Additionally, GM-CSF, which binds to myeloid cells, can be used as a cell-binding agent to diseased cells from acute myelogenous leukemia. IL-2, which binds to activated T-cells, can be used for prevention of transplant graft rejection, for therapy and prevention of graft-versus-host disease, and for treatment of acute T-cell leukemia MSH, which binds to melanocytes, can be used for the treatment of melanoma. Folic acid, which targets the folate receptor expressed on ovarian and other cancers is also a suitable cell-binding agent.

Cancers of the breast and testes can be successfully targeted with estrogen (or estrogen analogues) or androgen (or androgen analogues), respectively, as cell-binding agents.

Cytotoxicity Assays

The cytotoxic conjugates of the present invention can be evaluated for their ability to suppress proliferation of various unwanted cell lines in vitro. For example, cell lines such as the human epidermoid carcinoma line A-431, the human small cell lung cancer cell line SW2, the human breast tumor line $SKBR_3$ and the Burkitt's lymphoma line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

Cytotoxicity can also be measured by back-extrapolation of cell proliferation curves as described in Goldmacher et al, *J. Immunol.* 135:3648–3651 (1985), or by clonogenic assays as described in Goldmacher et al, *J. Cell Biol.* 102:1312–1319 (1986).

Therapeutic Composition

The present invention also provides a therapeutic composition comprising:

(A) an effective amount of one or more cytotoxic conjugate, and
(B) a pharmaceutically acceptable carrier.

Similarly, the present invention provides a method for killing selected cell populations comprising contacting target cells, or tissue containing target cells, with an effective amount of a cytotoxic conjugate, or therapeutic agent comprising a cytotoxic conjugate.

The cytotoxic conjugate is prepared as described above.

Cytotoxic conjugates can be evaluated for in vitro potency and specificity by methods previously described (see, e.g., R. V. J., Chari et al, *Cancer Res.* 55:4079–4084 (1995)). Anti-tumor activity can be evaluated in human tumor xenograft models in mice by methods also previously described (see, e.g., Liu et al, *Proc. Natl. Acad. Sci.* 93:8618–8623 (1996)).

Suitable pharmaceutically-acceptable carriers are well known and can be determined by those of ordinary skill in the art as the clinical situation warrants. As used herein, carriers include diluents and excipients.

Examples of suitable carriers, diluents and/or excipients include: (1) Dulbecco's phosphate buffered saline, pH~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20.

The method for killing selected cell populations can be practiced in vitro, in vivo, or ex vivo. As used herein, killing means causing the death of a cell, lysing a cell, inducing cell death, or decreasing cell viability.

Examples of in vitro uses include treatments of autologous bone marrow prior to their transplant into the same patient in order to kill diseased or malignant cells; treatments of bone marrow prior to its transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogeneic bone marrow or tissue prior to transplant in order to prevent graft versus host disease (GVHD). Treatment can be carried out as follows. Bone marrow is harvested from the patient or other individual and then incubated in medium containing serum to which is added the cytotoxic agent of the invention. Concentrations range from about 10 $\mu$M to 1 $\mu$M, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels. Examples of suitable protocols of cytotoxic conjugate administration are as follows. Conjugates are given weekly for 4 weeks as an i.v. bolus each week. Bolus doses are given in 50 to 100 ml of normal saline to which 5 to 10 ml of human serum albumin can be added. Dosages will be 10 $\mu$g to 100 mg per administration, i.v. (range of 100 ng to 1 mg/kg per day).

More preferably, dosages will range from 50 µg to 30 mg. Most preferably, dosages will range from 1 mg to 20 mg. After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

EXAMPLES

Example 1

Synthesis of Exemplary PEG Linking Groups
15-Hydroxy-4,7,10,13-tetraoxapentadecanoic Acid tert-Butyl Ester (9a)

Figure 7:
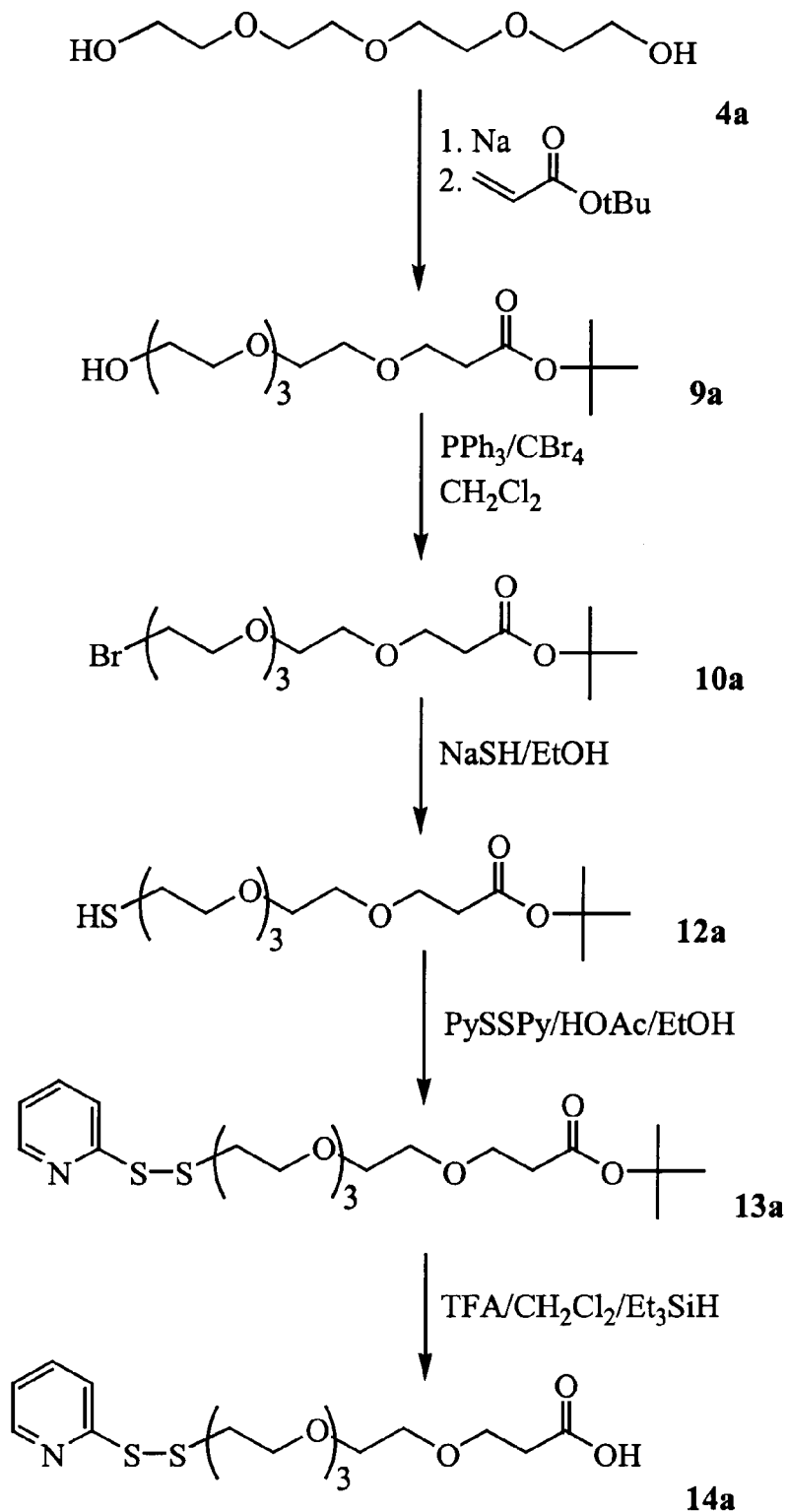

To 300 mL of anhydrous THF was added 80 mg (0.0025 mol) of sodium metal and 128 mL of tetraethylene glycol 4a (0.94 mol) with stirring (Seitz and Kunz, *J. Org. Chem.*, 62:813–826 (1997)). After the sodium had completely dissolved, tert-butyl acrylate (24 mL, 0.33 mol) was added. The solution was stirred for 20 hrs at room temperature and neutralized with 8 mL of 1.0 M HCl. The solvent was removed in vacuo and the residue was suspended in brine (250 mL) and extracted with ethyl acetate (3×125 mL). The combined organic layers were washed with brine (100 mL) then water (100 mL), dried over sodium sulfate, and the solvent was removed. The resulting colorless oil was dried under vacuum to give 77.13 g (73% yield) of product 9a (FIG. 7). $^1$H NMR: 1.40 (s, 9H), 2.49 (t, 2H, J=6.4 Hz), 3.59–3.73 (m, 18H).

15-Bromo-4,7,10,13-tetraoxapentadecanoic Acid tert-Butyl Ester (10a)

To a stirred solution of 9a (1.0 g, 3.11 mmol) in 1 mL of pyridine at 0° C. was slowly added phosphorus tribromide (0.116 mL, 1.22 mmol) via syringe (Bradshaw et al., *J. Het. Chem.*, 27:347–349 (1990)). The solution was allowed to stir overnight, at which time TLC analysis indicated that the reaction was complete. Water (25 mL) was poured into the reaction vessel and the organics were extracted into methylene chloride (3×25 mL). The combined organic layers were washed with sodium bicarbonate (25 mL), followed by brine (25 mL), dried over magnesium sulfate, and the solvent was removed in vacuo. The residue was purified on silica gel using neat ethyl acetate as the eluant to give 400 mg (35% yield) of pure product 10a (FIG. 7). $^1$H NMR: 1.37 (s, 9H), 2.43 (t, 2H, J=6.4 Hz), 3.40 (t, 2H, J=6.4 Hz), 3.53–3.61 (m, 12H), 3.64 (t, 2H, J=6.4 Hz), 3.74 (t, 2H, J=6.4 Hz). $^{13}$C NMR: 27.90, 30.13, 36.06, 66.68, 70.17, 70.31, 70.32, 70.39, 70.46, 70.99, 80.22, 170.65.

Alternatively, 1.61 g (5.03 mmol) of 9a was co-evaporated successively with 100% ethanol and toluene, then dried over anhydrous sodium sulfate and 4A molecular sieves in dichloromethane. The mixture was filtered and concentrated. To the dried compound (1.42 g) in 20 ml of dichloromethane was added 2.48 g of carbontetrabromide (CBr$_4$, 7.47 mmol) and 1.50 g of triphenylphosphine (PPh$_3$, 5.71 mmol). After stirring under an atmosphere of argon overnight, the reaction mixture was filtered through a silica gel bed, then concentrated and purified by silica gel chromatography. (EtOAc/Hexane Gradient starting at a ratio of 1:2 and changing to a ratio of 2:3) to yield 0.92 g of the 10a. (62%). R$_f$=0.64 (EtOAc); $^1$H NMR (CDCl$_3$) 3.785 (t, 2H, J=6.3+6.3 Hz), 3.68 (t, 2H, J=6.5+6.5 Hz), 3.650 (m, 8H), 3.615 (m, 4H), 3.462 (t, 2H, J=6.3+6.4 Hz), 2.491 (t, 2H, J=6.5+6.5 Hz), 1.434 (s, 9H); $^{13}$C NMR 171.063, 80.656, 71.368, 70.831, 70.764, 70.706, 70.678, 70.545, 67.061, 36.431, 30.474, 28.263; MS m/z 408.74 (M+Na)$^+$, 406.70, 405.70, 404.73.

15-Mercapto-4,7,10,13-tetraoxapentadecanoic Acid tert-Butyl Ester (12a)

A flask was charged with Amberlite ion exchange resin IRA-400(Cl$^-$ form) (1.3g, 4.94 mmol of Cl$^-$) and a solution of NaSH.H$_2$O (0.218 g, 3.9 mmol) dissolved in 8 mL of MeOH was added with stirring (Choi and Yoon, *Syn.*, 373–375 (1995)). After allowing to stir for one hour, at which time the reaction became cloudy, a solution of triethylamine hydrochloride (0.180 g, 1.30 mmol) in 1.5 mL of MeOH was added. A solution of 10a (0.500 g, 1.3 mmol) in 2 mL of MeOH was then added dropwise and allowed to stir at room temperature for 16 hrs. The resin was then filtered off and 30 mL of 0.5 M HCl was added. The organic layer was separated, and the aqueous layer was extracted into methylene chloride (2×25 mL). The combined organic layers were dried over anhydrous sodium sulfate, and the solvent removed in vacuo. The residue was purified on silica gel using neat ethyl acetate as the eluant to give 250 mg (60% yield) of the thiol 12a (FIG. 7). $^1$H NMR: 1.41 (s, 9H), 2.46 (t, 2H, J=6.4 Hz), 2.85 (t, 2H, J=6.4 Hz), 3.55–3.62 (m, 12H), 3.64–3.71 (m, 4H). $^{13}$C NMR: 27.98, 36.14, 38.27, 66.77, 69.51, 70.25, 70.27, 70.39, 70.41, 70.48, 70.52, 80.36, 170.77. MS m/z Calculated: 361.17, Found: 361.94.

Alternatively, 800 mg of NaHS.xH$_2$O in pure ethanol was stirred until completely dissolved. To the ethanol solution was added 500 mg of 10a in 3 ml of tetrahydrofuran. After stirring under argon for 5 hrs, 0.5 ml of acetic acid was added. The mixture was evaporated to dryness, then suspended with THF/EtOAc and filtered through a silica gel bed. The filtrate was concentrated and purified by silica gel chromatography (EtOAc/Hexane 2:1) to yield 382 mg of 12a (87%). R$_f$=0.47 (EtOAc); $^1$H NMR (CDCl$_3$) 3.810 (t, 2H, J=6.5+6.5 Hz), 3.693 (t, 2H, J=6.6+6.6 Hz), 3.653 (m, 8H), 3.620 (m, 4H), 3.161 (t, 1H, J=6.4+6.4 Hz), 3.072 (t, 1H, J=6.6+6.6 Hz), 2.503 (t, 2H, J=6.6+6.6 Hz), 1.447 (s, 9H); $^{13}$C NMR 171.098, 80.700, 70.862, 70.815, 70.746, 70.720, 70.698, 70.669, 70.575, 69.629, 69.468, 67.105, 38.191, 36.475, 28.307; MS m/z 361.56 (M+Na)$^+$.

15-(2-Pyridyldithio)-4,7,10,13-tetraoxapentadecanoic Acid tert-Butyl Ester (13a)

To a solution of 15-mercapto-4,7,10,13-tetraoxapentadecanoic acid tert-butyl ester (12a) (125 mg. 0.37 mmol) in 5 ml of ethanol was added 2,2'-dithiodipyridine (300 mg, 2.1 mmol) and 20 µl of glacial acetic acid. The mixture was stirred overnight under an argon atmosphere, and the solvent was evaporated. The residue was purified by silica gel chromatography (EtOAc/Hexane 3:2) to yield 146 mg (88% yield) of the title compound 13a (FIG. 7). R$_f$=0.44 (EtOAc/Hexane 2:1); $^1$H NMR (CDCl$_3$) 8.380 (ddd, 1H, J=0.7, 1.4, 4.8 Hz), 7.710 (dd, 1H, J=0.8, 7.2 Hz), 7.600 (dt, 1H, J=1.8, 7.5, 7.5 Hz), 7.015 (m, 1H), 3.663–3.492 (m, 16H), 2.92 (t, 2H, J=6.4+6.4 Hz), 2.425 (t, 2H, J+6.6+6.5 Hz), 1.372 (s, 9H); $^{13}$C NMR 170.844, 160.421, 149.467, 137.136, 120.604, 119.578, 80.431, 70.647, 70.589, 70.486, 70.400, 70.353, 68.895, 66.872, 38.475, 36.257, 28.091; MS 470.77 (M+Na)$^+$.

15-(2-Pyridyldithio)-4,7,10,13-tetraoxapentadecanoic Acid (14a)

To a solution of 140 mg of 15-(2-pyridyldithio)-4,7,10, 13-tetraoxapentadecanoic acid tert-butyl ester (13a) in 5 ml of dichloromethane was added 1.0 ml of TFA and 250 μl of Et$_3$SiH. After stirring for 2 hrs, the mixture was diluted with 5 ml of toluene. The mixture was evaporated and then co-evaporated three times with 5 ml of toluene and dried under vacuum to yield of 122 mg (99% yield) of the title compound 14a (FIG. 7). $^1$H NMR (CDCl$_3$) 13.331 (s, OH), 8.770 (d, 1H, J=5.4 Hz), 8.299 (t, 1H, J=7.7+7.7 Hz), 8.130 (d, 1H, J=8.2 Hz), 7.677 (t, 1H J=6.3+6.4 Hz), 3.703–3.556 (m, 16H), 3.109 (t, 2H, J=6.4+6.4 Hz), 2.538 (t, 2H, J=6.1+ 6.1 Hz); $^{13}$C NMR 175.900, 157.402, 144.807, 129.114, 124.746, 123.635, 70.452, 70.327, 70.206, 70.184, 69.881, 69.862, 67.229, 66.407, 39.320, 34.866; MS 392.73 (M+H)$^+$, 390.76 (M–H)$^–$.

15-O-Tosyl-4,7,10,13-tetraoxapentadecanoic Acid tert-Butyl Ester (17a)

Figure 8:
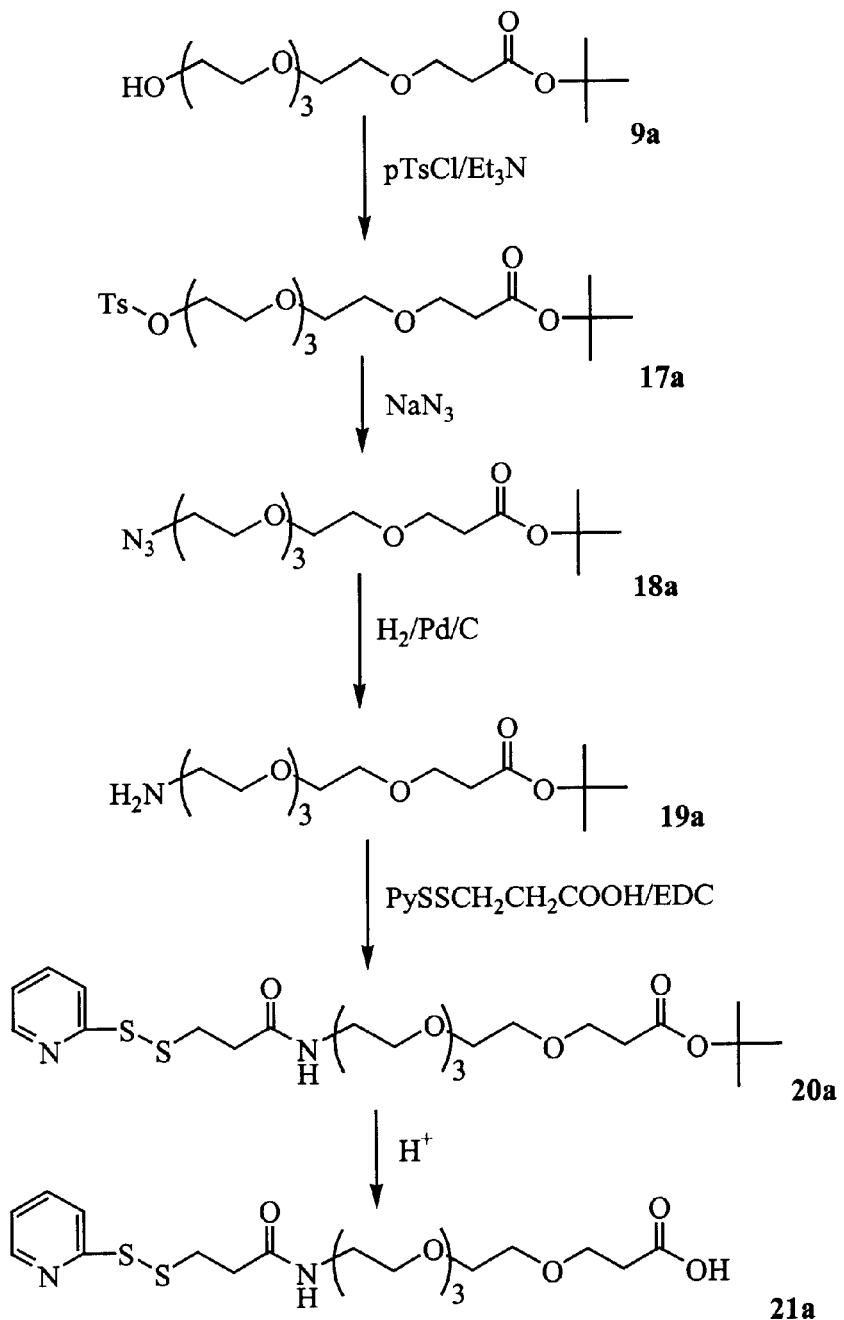

A solution of 9a (10 g, 31 mmol) in acetonitrile (100 mL) was treated with triethylamine (5.18 mL). A solution of tosyl chloride (7.12 g, 37.3 mmol) in 50 mL acetonitrile was added dropwise via an addition funnel over 30 minutes. After 5 hrs TLC analysis revealed that the reaction was complete. The triethylamine hydrochloride that had formed was filtered off and the solvent was removed. The residue was purified on silica gel by loading the column with 20% ethyl acetate in hexane and eluting with neat ethyl acetate to give 11.2 g (76% yield) of 17a (FIG. 8). $^1$H NMR: 1.40 (s, 9H), 2.40 (s, 3H), 2.45 (t, 2H, J=6.4 Hz), 3.52–3.60 (m, 12H), 3.62–3.68 (m, 4H), 4.11 (t, 2H, J=4.8 Hz), 7.30 (d, 2H, J=8.0 Hz), 7.75 (d, 2H, J=8.0 Hz), $^{13}$C NMR: 21.48, 27.94, 36.12, 66.73, 68.50, 69.12, 70.20, 70.34, 70.36, 70.41, 70.45, 70.57, 80.31, 127.82, 129.68, 132.86, 144.64, 170.72.

15-Azido-4,7,10,13-tetraoxapentadecanoic Acid tert-Butyl Ester (18a)

To 10 mL of DMF was added 17a (4.0 g, 8.4 mmol) and sodium azide (0.737 g, 11.3 mmol) with stirring. The reaction was heated to 80° C. and monitored by TLC. After 5 hrs TLC analysis revealed that the reaction was complete. The reaction was cooled to room temperature and quenched with water (25 mL). The aqueous layer was separated and extracted into ethyl acetate (3×25 mL). The combined organic layers were dried over anhydrous magnesium sulfate, filtered, and the solvent removed in vacuo. The crude azide 18a was used without further purification (FIG. 8). 1H NMR: 1.39 (s, 9H), 2.44 (t, 2H, J=6.4 Hz), 3.32 (t, 2H, J=5.2 Hz), 3.52–3.65 (m, 16H).

15-Amino-4,7,10,13-tetraoxapentadecanoic Acid tert-Butyl Ester (19a)

The crude material 18a (3.0 g, 8.0 mmol) was dissolved in ethanol (20 mL) and 300 mg of 10% Pd/C was added. The system was evacuated under vacuum and placed under 1 atm of hydrogen gas via balloon with vigorous stirring, and repeated 4 times to ensure a pure hydrogen atmosphere. The reaction was then stirred overnight at room temperature. TLC showed that the reaction was complete after 16 hrs. The crude reaction was passed through a short pad of celite rinsing with ethyl acetate. The solvent was removed and the amine purified on silica gel using a mixture of 15% methanol and 2.5% triethylamine in methylene chloride as the eluant to give 2.3 g (85% yield) of the desired amine 19a (FIG. 8). $^1$H NMR: 1.36 (s, 9H), 2.27 (br s., 2H), 2.42 (t, 2H, J=6.4 Hz), 2.80 (t, 2H, J=5.2 Hz), 3.45 (d, 2H, J=5.2 Hz), 3.51–3.59 (m, 12H), 3.63 (d, 2H, J=6.4 Hz). MS: m/z Calculated: 322.21, Found: 321.97.

15-[N-(3-(2-Pyridyldithio)-propionyl)]-4,7,10,13-tetraoxapentadecanoic Acid tert-Butyl Ester (20a)

A small flask was charged with amine 19a (0.550 g, 1.7 mmol), 3-(2-pyridyldithio)-propionic acid (0.550 g, 2.6 mmol), EDC (0.694 g, 3.4 mmol), DMAP (0.103 g, 0.88 mmol), and methylene chloride (12 mL). The reaction was stirred at room temperature overnight. TLC revealed that all starting material had been consumed after 16 hours. The reaction was quenched with ammonium chloride (50 mL) and extracted into ethyl acetate (3×50 mL), dried over anhydrous magnesium sulfate, and the solvent was remove in vacuo. The residue was purified on alumina using neat ethyl acetate by TLC monitoring in 5% methanol in methylene chloride to obtain 562 mg (65% yield) of the desired coupled product 20a (FIG. 8). $^1$H NMR: 1.40 (s, 9H), 2.46 (t, 2H, J=6.4 Hz), 2.58 (t, 2H, J=6.8 Hz), 3.05 (t, 2H, J=6.8 Hz), 3.43 (m, 2H), 3.50–3.62 (m, 14H), 3.66 (t, 2H, J=6.4 Hz), 7.07 (m, 1H), 7.61–7.63 (m, 2H), 8.45 (m, 1H). MS for C$_{23}$H$_{38}$N$_2$O$_7$S$_2$—Na$^+$: m/z calculated: 541.20; found: 541.11.

15-[N-(3-(2-Pyridyldithio)-propionyl]-4,7,10,13-tetraoxapentadecanoic Acid (21a)

To a small flask was added 20a (35 mg, 0.0674 mmol) in 3 mL of methylene chloride. To this solution was added 0.5 mL of TFA with stirring. After 1 hr the reaction was complete by TLC. Toluene (3 mL) was added to the reaction mixture and the solvent removed in vacuo. The residue was purified on silica gel using a mixture of 10% methanol and 2% acetic acid in methylene chloride as the eluant to give 14 mg (45% yield) of the desired product 21a (FIG. 8). $^1$H NMR: 2.61 (t, 2H, J=6.4 Hz), 2.64 (t, 2H, J=6.8 Hz), 3.06 (t, 2H, J=6.8 Hz), 3.45 (m, 2H), 3.57–3.68 (m, 16H), 3.78 (t, 2H, J=6.4 Hz), 7.13 (m, 1H), 7.66–7.74 (m, 2H), 8.48 (d, 1H, J=5.2 Hz). m/z LC/MS for C$_{19}$H$_{30}$N$_2$O$_7$S$_2$—Na$^+$: calcd: 485.14; found: 485.00.

15-[O-{3-(2-Pyridyldithio)-propionyl}]-4,7,10,13-tetraoxapentadecanoic Acid tert-Butyl Ester (29a)

Figure 9:
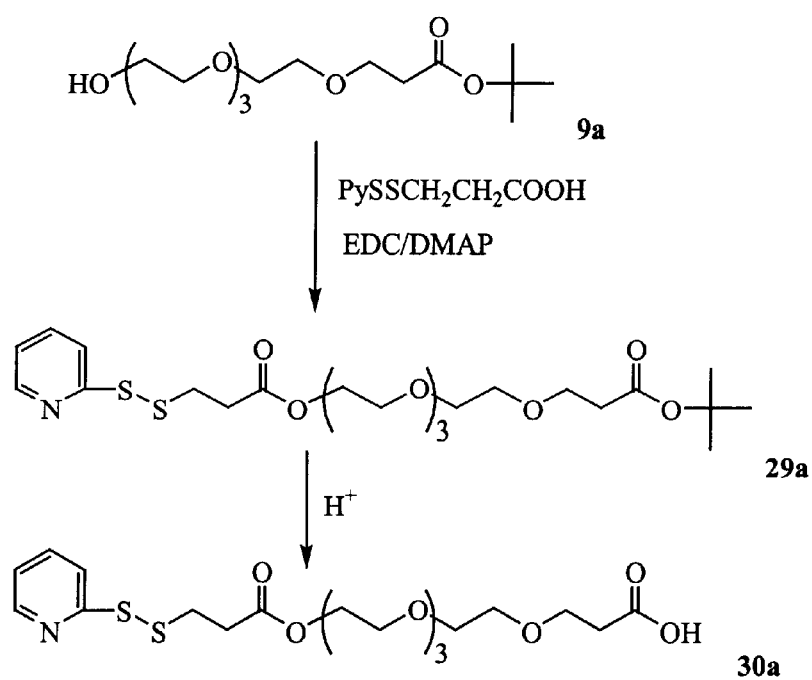

A small flask was charged with alcohol 9a (0.500 g, 1.55 mmol), 3-(2-pyridyldithio)-propionic acid (0.666 g, 3.1 mmol), EDC (0.593 g, 3.1 mmol), DMAP (0.095 g, 0.76 mmol), and methylene chloride (10 mL). The reaction was stirred at room temperature overnight. TLC analysis indicated that all starting material had been consumed after 16 hours. The reaction was quenched with ammonium chloride (50 mL) and extracted into ethyl acetate (3×50 mL), dried over anhydrous magnesium sulfate, and the solvent was remove in vacuo. The residue was purified on silica gel using neat ethyl acetate as the eluant to give 500 mg (62% yield) of the desired coupled product 29a (FIG. 9). $^1$H NMR: 1.42 (s, 9H), 2.48 (t, 2H, J=6.4 Hz), 2.77 (t, 2H, J=6.8 Hz), 3.03 (t, 2H, J=6.8 Hz), 3.54–3.64 (m, 12H), 3.65–3.72 (m, 4H), 4.23 (m, 2H), 7.07 (m, 1H), 7.60–7.66 (m, 2H), 8.46 (m, 1H). MS: m/z Calculated: 542.19. Found: 542.06.

15-[O-(3-(2-Pyridyldithio)-propionate)-hydroxy]-4,7,10, 13-tetraoxapentadecanoic Acid (30a)

To a small flask was added 29a (45 mg, 0.0867 mmol) in 3 mL of methylene chloride. To this solution was added 0.7 mL of TFA with stirring. After 1 hr the reaction was complete by TLC. Toluene (2 mL) was added to the reaction mixture and the solvent removed in vacuo. The residue was purified on silica gel using neat ethyl acetate as the eluant to give 32 mg (80% yield) of the desired product 30a (FIG. 9). $^1$H NMR: 2.62 (t, 2H, J=6.0 Hz), 2.78 (t, 2H, J=7.0 Hz), 3.03 (t, 2H, J=7.0 Hz), 3.62–3.68 (m, 12H), 3.69 (t, 2H, J=4.6 Hz, 3.76 (t, 2H, J=6.0 Hz), 4.25 (t, 2H, J=4.6 Hz), 7.12 (m, 1H), 7.65–7.74 (m, 2H), 8.48 (d, 1H, J=4.8 Hz). MS: m/z for $C_{19}H_{29}NOS_2$—$Na^+$: calcd: 486.13; found: 486.00.

Example 2

Synthesis of a Cytotoxic Agent Bearing a Reactive PEG Moiety

15-[N-(3-(L-DM1-Dithio)-propionyl]4,7,10,13-tetraoxapentadecanoic Acid (41a)

L-DM1 (8.1 mg, 0.011 mmol) and 15-[N-(3-(2-pyridyldithio)-propionyl]-4,7,10,13-tetraoxapentadecanoic acid 21a (6.9 mg, 0.015 mmol) were dissolved in 0.40 mL of glass distilled ethyl alcohol, in a 1 mL flask. Potassium phosphate buffer (0.20 mL, 100 mM, 2 mM EDTA pH 7.5) was added and the solution was stirred for 2 hours under an argon atmosphere. The reaction mixture was purified by HPLC at room temperature using a 250×10 cm Vydac ODS II column, flow rate of 4.5 mL/min with a linear gradient of di-water 0.05% trifluoroacetic acid, acetonitrile (20% acetonitrile to 70% acetonitrile over 30 min). Desired product (retention time 17.2 min) was collected and solvent was removed by rotary evaporation under vacuum to give 7 mg (58% yield) of the desired product 41a (FIG. 10). MS m/z: 1110.3 ($M^+$+Na). $^1$H NMR (CDCl$_3$) 7.17 (m, 1H), 6.83 (d, 1H J=1.8 Hz), 6.62 (d, 1H, J=1.8 Hz), 6.31–6.46 (m, 2H), 5.57–5.69 (m, 1H), 5.36–5.41 (m, 1H), 4.77 (dd, 1H, J=12, 1.8 Hz), 4.27 (dd, 1H, 12, 1.8 Hz), 3.98 (s, 3H), 3.33–3.7 (m, 14H), 3.72–3.82 (m, 2H), 3.41–3.51 (m, 4H), 3.35 (s, 3H), 3.23 (s, 3H), 3.12 (d, 1H, J=12.5 Hz), 2.5–3.05 (m, 13H), 2.12 (dd, 1H, 7.2,0.8 Hz), 1.96 (s, 3H), 1.63 (s, 3H), 1.41–1.49 (m, 1H), 1.19–1.35 (m, 9H), 0.80 (s, 3H).

15-[N-(3-(L-DM1-Dithio)-propionyl]-4,7,10,13-tetraoxapentadecanoic Acid-N-hydroxy Succinimide Ester (2a)

15-[N-(3-(L-DM1-dithio)-propionyl]-4,7,10,13-tetraoxapentadecanoic acid 41a (7 mg, 0.0064 mmol) was dissolved in 1.0 mL of methylene chloride to which was added N-hydroxysuccinimide (10 mg, 0.087 mmol) and 1-(3-dimethylaminopropyl)-3-ethylcarbodiimide hydrochloride (10 mg, 0.052 mmol). The solution was stirred at room temperature for 2.5 hours and was purified by silica chromatography using a mobile phase of methylene chloride:methyl alcohol:acetic acid 90:9.9:0.1, solvent was removed under vacuum giving 5 mg (65% yield) of the desired product 2a (FIG. 10). MS m/z: 1208.3 ($M^+$+Na), 1220.3 ($M^+$+K). $^1$H NMR (CDCl$_3$) 6.83 (d, 1H, J=1.8 Hz), 6.70 (d, 1H, J=11 Hz), 6.62 (d, 1H, 1.8 Hz), 6.38–6.45 (m, 2H), 6.25 (s, 1H), 6.06–6.21 (m, 1H), 5.82–5.89 (m, 1H), 5.65 (dd, 1H, J=15, 9 Hz), 5.38 (dd, 1H, J=13, 6 Hz), 4.78, (dd, 1H, J=12, 3 Hz), 4.28 (dt, 1H, J=0.5, 10 Hz), 3.98 (s, 3H), 3.84 (t, 1H, J=6.7 Hz), 3.61–3.73 (m, 14H), 3.41–3.57 (m, 4H), 3.35 (s, 3H), 3.23 (s, 3H), 3.08 (s, 3H), 2.78–2.91 (m, 4H), 2.47–2.70 (m, 12H), 2.35 (s, 4H), 1.96 (s, 1H), 1.53–1.66 (m, 3H), 1.21–1.31 (m, 7H), 0.80 (s, 3H).

15-(L-DM1-Dithio)-4,7,10,13-tetraoxapentadecanoic Acid (41b)

L-DM1 (13 mg, 0.017 mmol) and 15-(2-pyridyldithio)-4,7,10,13-tetraoxapentadecanoic acid 14a (9 mg, 0.023 mmol) were dissolved in 0.40 mL of glass distilled ethyl alcohol, in a 1 mL flask. Potassium phosphate buffer (0.20 mL, 100 mM, 2 mM EDTA pH 7.5) was added and the solution was stirred for 2 hours under an argon atmosphere. The reaction mixture was purified by HPLC at room temperature using a 250×10 cm Vydac ODS II column, flow rate of 4.5 mL/min with a linear gradient of di-water 0.05% trifluoroacetic acid, acetonitrile (20% acetonitrile to 70% acetonitrile over 30 min). Desired product (retention time 18.5 min) was collected and solvent was removed by rotary evaporation under vacuum to give 11 mg (61% yield) of the desired product 41b (FIG. 11). MS: m/z=1040 ($M+Na^+$). $^1$H NMR (CDCl$_3$) 7.17 (m, 1H), 6.83 (d, 1H J=1.8 Hz), 6.62 (d, 1H, J=1.8 Hz), 6.31–6.46 (m, 2H), 5.57–5.69 (m, 1H), 5.36–5.41 (m, 1H), 4.77 (dd, 1H, J=12, 1.8 Hz), 4.27 (dd, 1H, 12, 1.8 Hz), 3.98 (s, 3H), 3.33–3.7 (m, 14H), 3.72–3.82 (m, 2H), 3.41–3.51 (m, 4H), 3.35 (s, 3H), 3.23 (s, 3H), 3.12 (d, 1H, J=12.5 Hz), 2.5–3.05 (m, 13H), 2.12 (dd, 1H, 7.2, 0.8 Hz), 1.96 (s, 3H), 1.63 (s, 3H), 1.41–1.19 (m, 1H), 1.19–1.35 (m, 9H), 0.80 (s, 3H).

15-(L-DM1-Dithio)-4,7,10,13-tetraoxapentadecanoic Acid-N-hydroxysuccinimide Ester (2b)

15-(L-DM1-dithio)-4,7,10,13-tetraoxapentadecanoic Acid 41b (10 mg, 0.0098 mmol) was dissolved in 1.0 mL of methylene chloride to which was added N-hydroxysuccinimide (8.0 mg, 0.070 mmol) and 1-(3-dimethylaminopropyl)-3-ethylcarbodiimide hydrochloride (9.1 mg, 0.047 mmol). The solution was stirred at room temperature for 2.5 hours and was purified by silica chromatography using a mobile phase of methylene chloride:methyl alcohol:acetic acid 90:9.9:0.1, solvent was removed under vacuum giving 10 mg (91% yield) of the desired product 2b (FIG. 11). MS: m/z=1208 ($M+Na^+$), 1224 ($M+K^+$). $^1$H NMR (CDCl$_3$) 6.82 (d, 1H, J=1.8 Hz), 6.71 (d, 1H, J=11 Hz), 6.63 (d, 1H, 1.8 Hz), 6.38–6.45 (m, 1H), 6.27 (s, 1H), 6.06–6.21 (m, 1H), 5.82–5.89 (m, 1H), 5.65 (dd, 1H, J=15, 9 Hz), 5.38 (dd, 1H, J=13, 6 Hz), 4.76, (dd, 1H, J=12, 3 Hz), 4.27 (dt, 1H, J=0.5, 10 Hz), 3.98 (s, 3H), 3.84 (t, 1H, J=6.7 Hz), 3.61–3.73 (m, 14H), 3.41–3.57 (m, 4H), 3.35 (s, 31H), 3.23 (s, 3H), 3.08 (s, 3H), 2.78–2.91 (m, 4H), 2.47–2.70 (m, 8H), 2.35 (s, 4H), 1.96 (s, 1H) 1.53–1.66 (m, 3H), 1.21–1.31 (m, 7H), 0.79 (s, 3H).

Example 3

Synthesis of a Cytotoxic Conjugate Comprising a Cytotoxic Agent Linked to a Cell-Binding Agent Via a PEG Linking Group Cytotoxic Conjugate Comprising a Cytotoxic Agent Linked to a Cell-Binding Agent Through Compound 2a Compound 2a was dissolved in anhydrous ethanol to obtain a stock concentration of 5 mM (5.9 mg/mL). The cell binding agent used in this experiment was a murine monoclonal antibody targeting the Epidermal Growth Factor Receptor (EGFR) that was developed at ImmunoGen. A solution of the anti-EGFR antibody KS-77 (2 mg/mL, 0.25 mL) in 50 mM potassium phosphate buffer, pH 6.5, containing 50 mM NaCl and 2 mM ethylenediaminetetraacetic acid (EDTA) was treated with a 12-fold molar excess of 2a. The final concentration of ethanol in the reaction mixture was 5% (v/v). The reaction mixture was incubated at ambient temperature for 2 hours. The cytotoxic conjugate 3a (FIG. 12) was purified by size-exclusion chromatography over a Sephadex G25 column, which had been previously equilibrated in phosphate-buffered saline (PBS) pH 6.5. This purification step removed unreacted 2a and other low molecular weight material. The final conjugate had, on the average, 1.9 DM1 molecules linked per antibody molecule, as determined using the following extinction coefficients: for 2a: $\epsilon_{252\ nm}$=24,681 $M^{-1}cm^{-1}$, $\epsilon_{280\ nm}$=5,700 $M^{-1}cm^{-1}$ and for the antibody: $\epsilon_{252\ nm}$=82,880 $M^{-1}cm^{-1}$, $\epsilon_{280\ nm}$=224,000 $M^{-1}cm^{-1}$. This conjugate 3a is designated as KS-77-PEG-DM1, Batch 1.

Another conjugate (termed "KS-77-PEG-DM1, Batch 2") was prepared in an analogous manner, except that the DM1-PEG linker 2a was dissolved in dimethylacetamide (DMA) instead of ethanol. The final DMA concentration in the conjugation mixture was 5% v/v. The conjugate was purified as described above, and contained, on the average, 1.8 DM1 molecules linked per antibody molecule.

Example 4

In Vitro Cytotoxic Assay

The in vitro cytotoxicity of KS-77-PEG-DM1, Batches 1 and 2, was measured in a clonogenic assay using the EGF-receptor-positive human tumor cell line A-431 (ATCC CRL-1555). The target specificity of the cytotoxic effect was measured using the antigen-negative human melanoma cell line A-375 (ATCC CRL-1619). Cells were plated at different densities in 6-well tissue-culture plates in Dulbecco's modified minimum essential medium (DMEM) supplemented with 10% fetal calf serum. Cytotoxic conjugates at varying concentrations (ranging from $3\times10^{-11}$ to $3\times10^{-9}$ M) were added and the cells were maintained in a humidified atmosphere at 37° C. and 6% $CO_2$ until colonies of approximately 20 cells or more were formed (6 to 10 days). Control plates contained no cytotoxic conjugates. The cells were then fixed with formaldehyde, stained with crystal violet, and counted under a low-magnification microscope. Plating efficiencies were then determined from the colony numbers and surviving fractions of cells were calculated as the ratio of the plating efficiency of the treated sample and the plating efficiency of the control.

Figure 14:
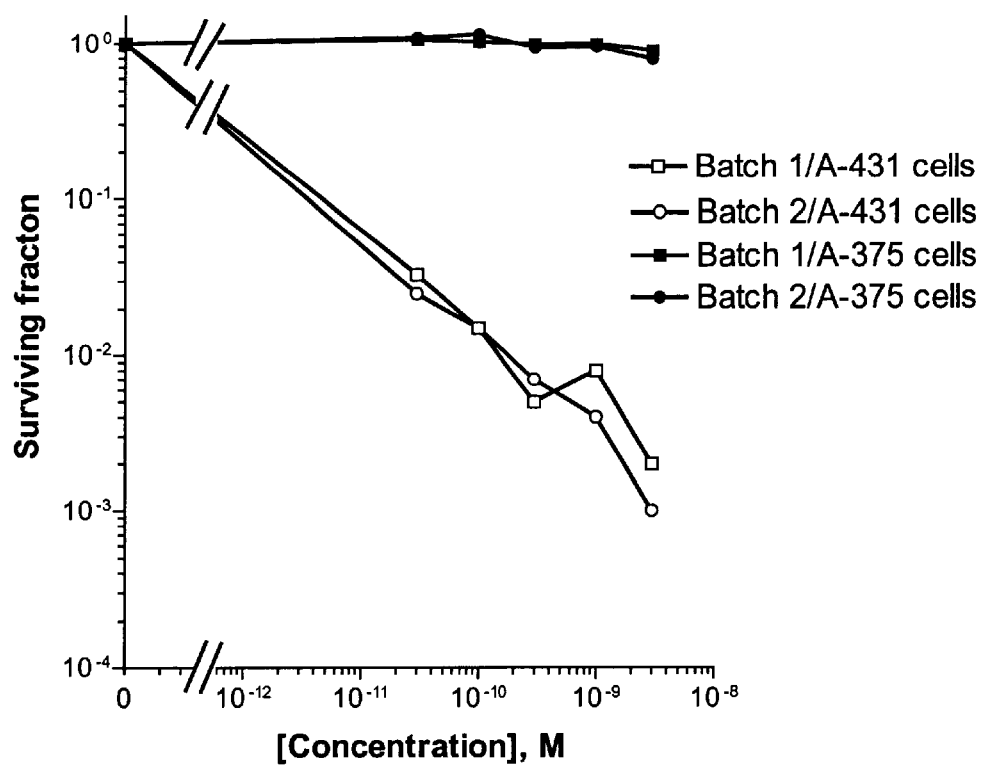
FIG. 14 shows the results of analyses performed to determine the in vitro cytotoxicity and specificity of cytotoxic conjugates KS-77-PEG-DM1, Batches 1 & 2.

FIG. 14 shows the results of the cytotoxicity determination for the two batches of KS-77-PEG-DM1 conjugates on the target antigen-positive cell line A431. Conjugates from both batches show similar high cytotoxicity to the target cells; with $IC_{50}$ values less than $3\times10^{-11}$ M (lowest concentration tested). Exposure to a conjugate concentration of $1\times10^{-9}$ M resulted in surviving fractions of less than $10^{-3}$ (less than 0.1% of cells survive). In contrast, the conjugates were essentially non-toxic to antigen negative cells, with an $IC_{50}$ value greater than $3\times10^{-9}$ M (highest concentration tested). These results demonstrate the selective killing of antigen-positive cells and that the cytotoxic effect of the cytotoxic conjugates is dependent on the specific binding through the antibody component.

Example 5

Determination of Affinity

Figure 15:
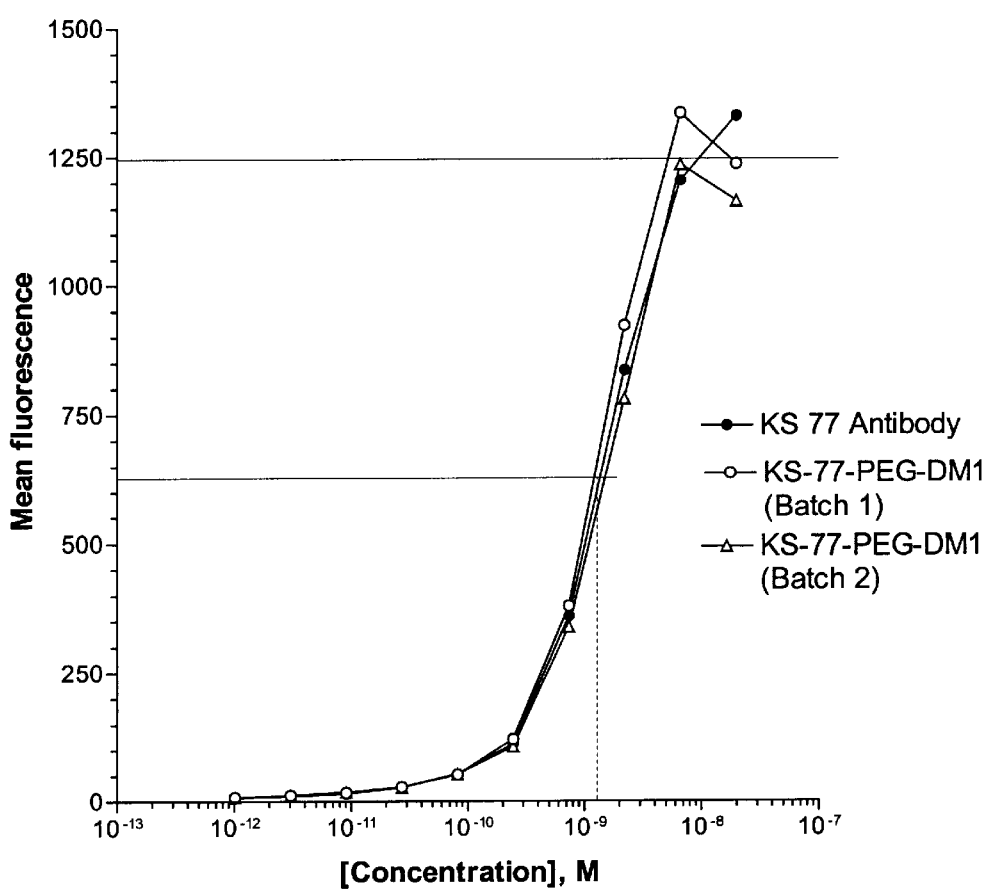
FIG. 15 shows the results of analyses performed to compare the binding affinities of unconjugated KS-77 antibody and the cytotoxic conjugates KS-77-PEG-DM1.

The specific affinities of the unconjugated KS-77 antibody was compared to that of the two cytotoxic conjugates, KS-77-PEG-DM1, Batches 1 & 2 (described in Example 3) by binding assays on antigen-expressing A-431 cells. A-431 cells were grown in tissue culture grade flasks containing DMEM supplemented with 10% fetal bovine calf serum. The cells were then trypsinized and incubated in suspension, at 37° C., for 30 minutes in the same medium in non-tissue culture grade flasks to prevent adherence of cells to the plastic. The cells were then transferred to wells of 96 well plates and re-suspended in minimum essential medium containing 25% pooled human serum. Cell suspensions (0.2 ml suspension containing 200,000 cells/well) were incubated for 2 hours at 4° C., with various concentration of either of the cytotoxic conjugates or unconjugated KS-77 antibody. The cells were then washed with buffer containing 2% goat serum, and then treated with fluorescein-labeled goat anti-mouse IgG for 1 h at 4° C. Cells were then washed again with buffer, and fixed with 1% formaldehyde in phosphate buffered saline. Mean cell fluorescence was measured on a flow cytometer. The mean fluorescence is plotted as a function of antibody or conjugate concentration. The results (FIG. 15) indicate that the unconjugated antibody and the two DM1 cytotoxic conjugates bind to antigen expressing A-431 cells with similar affinities ($KD=1.3\times10^{-9}$ M for antibody and its conjugates). Thus, the linkage of DM1-PEG to the antibody preserves its binding affinity to the antigen on the target cells.

Example 6

In Vivo Anti-Tumor Activity

The anti-tumor effect of KS-77-PEG-DM1 cytotoxic conjugates can be measured on human squamous cancer (A431) xenografts in SCID mice as follows. First, a human tumor xenograft model in SCID mice is established. Five-week old female SCID mice (20 animals) are inoculated subcutaneously in the right flank with A431 human squamous cancer cells (1.5×106 cells/mouse) in 0.1 mL of serum-free medium. The tumors are grown for 11 days to an average size of 100.0 mm³ (range of 50–150 mm³). The animals are then randomly divided into four groups (5 animals per group). The first two groups receive the two KS-77-PEG-DM1 cytotoxic conjugates (18 mg/kg, qd×5) administered intravenously. The third group is treated with unconjugated KS-77 antibody (18 mg/kg, qd×5), also administered intravenously. The fourth group of animals is a control group that is treated with PBS using the same treatment schedule as in groups 1–3. The sizes of the tumors are measured twice weekly and the tumor volumes are calculated with the formula: ½(length×width×height). The weight of the animals is also measured twice per week. The anti-tumor effect can be determined by plotting the tumor-size as a function of time.

Example 7

In Vivo Clearance Studies and Pharmacokinetics

Blood clearances of a typical $^{125}$I-labeled murine or humanized unconjugated $IgG_1$ antibody and of its corresponding $^{125}$I-labeled-cytotoxic conjugate are determined in female CD-1 mice. The unconjugated antibody and the cytotoxic conjugates are radio-iodinated by the method of Bolton and Hunter (*Biochem. J.* 133:529–539 (1973)). The antibody and conjugates are injected intravenously into the tail vein into separate set of animals. Heparinized blood samples are collected from the retroorbital venus plexus at various time points (from 2 min up to 72 hours) and measured for radioactivity content. The residual radioactivity is then plotted as a function of time.

While the invention has been described in detail and with reference to specific embodiments thereof, it will be apparent to one of ordinary skill in the art that various changes and modifications can be made therein without departing from the spirit and scope of the invention.

What is claimed is:

1. A cytotoxic agent, bearing a polyethylene glycol (PEG) linking group having a terminal active ester and 1 to 20 monomeric units, of formula 2:

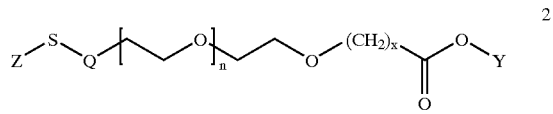

2 wherein:
   Z–S is a thiol-containing cytotoxic agent;
   Q is $R_2COO-$, $R_2R_3NCOO-$, $R_2OCOO-$, $R_2O-$, $R_2CONR_3-$, $R_2R_3N-$, $R_2OCONR_3-$, or S—, wherein:

R$_2$ is SCR$_4$R$_5$R$_6$—, wherein R$_4$, R$_5$ and R$_6$ are each H, linear alkyl, cyclic alkyl or branched alkyl, and may be the same or different;

R$_3$ is H or a linear alkyl, cyclic alkyl or branched alkyl;

n is an integer of from 0 to 20;

x is 1 or 2; and

Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

2. The cytotoxic agent of claim 1, wherein Z–S is a thiol-containing maytansinoid.

3. The cytotoxic agent of claim 1, wherein Z–S is a thiol-containing taxane.

4. The cytotoxic agent of claim 1, wherein Z–S is a thiol-containing CC-1065.

5. The cytotoxic agent of claim 1, wherein Z–S is a thiol-containing daunorubicin.

6. The cytotoxic agent of claim 1, wherein Z–S is a thiol-containing doxorubicin.

7. A cytotoxic agent, bearing a PEG linking group having a terminal active ester and 21 to 40 monomeric units, of formula 2:

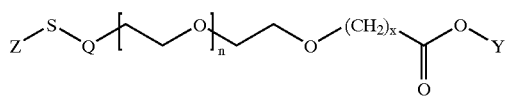

wherein:

Z–S is a thiol-containing cytotoxic agent;

Q is R$_2$COO—, R$_2$R$_3$NCOO—, R$_2$OCOO—, R$_2$O—, R$_2$CONR$_3$—, R$_2$R$_3$N—, R$_2$OCONR$_3$—, or S—, wherein:

R$_2$ is SCR$_4$R$_5$R$_6$—, wherein R$_4$, R$_5$ and R$_6$ are each H, linear alkyl, cyclic alkyl or branched alkyl, and may be the same or different;

R$_3$ is H or a linear alkyl, cyclic alkyl or branched alkyl;

n is an integer of from 21 to 40;

x is 1 or 2; and

Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

8. The cytotoxic agent of claim 7, wherein Z–S is a thiol-containing maytansinoid.

9. The cytotoxic agent of claim 7, wherein Z–S is a thiol-containing taxane.

10. The cytotoxic agent of claim 7, wherein Z–S is a thiol-containing CC-1065.

11. The cytotoxic agent of claim 7, wherein Z–S is a thiol-containing daunorubicin.

12. The cytotoxic agent of claim 7, wherein Z–S is a thiol-containing doxorubicin.

13. A cytotoxic agent, bearing a PEG linking group having a terminal active ester and 41 to 1000 monomeric units, of formula 2:

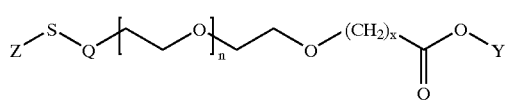

wherein:

Z–S is a thiol-containing cytotoxic agent;

Q is R$_2$COO—, R$_2$R$_3$NCOO—, R$_2$OCOO—, R$_2$O—, R$_2$CONR$_3$—, R$_2$R$_3$N—, R$_2$OCONR$_3$—, or S—, wherein:

R$_2$ is SCR$_4$R$_5$R$_6$—, wherein R$_4$, R$_5$ and R$_6$ are each H, linear alkyl, cyclic alkyl or branched alkyl, and may be the same or different;

R$_3$ is H or a linear alkyl, cyclic alkyl or branched alkyl;

n is an integer of from 41 to 1000;

x is 1 or 2; and

Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

14. The cytotoxic agent of claim 13, wherein Z–S is a thiol-containing maytansinoid.

15. The cytotoxic agent of claim 13, wherein Z–S is a thiol-containing taxane.

16. The cytotoxic agent of claim 13, wherein Z–S is a thiol-containing CC-1065.

17. The cytotoxic agent of claim 13, wherein Z–S is a thiol-containing daunorubicin.

18. The cytotoxic agent of claim 13, wherein Z–S is a thiol-containing doxorubicin.

19. A cytotoxic conjugate having one or more cytotoxic agents covalently bonded to a cell-binding agent through a PEG linking group having 1 to 20 monomeric units, of formula 3:

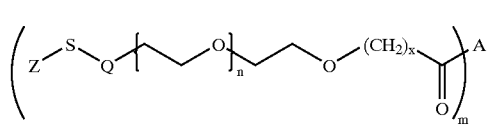

wherein:

Z–S is a thiol-containing cytotoxic agent;

Q is R$_2$COO—, R$_2$R$_3$NCOO—, R$_2$OCOO—, R$_2$O—, R$_2$CONR$_3$—, R$_2$R,N—, R$_2$OCONR$_3$—, or S—, wherein:

R$_2$ is SCR$_4$R$_5$R$_6$—, wherein R$_4$, R$_5$ and R$_6$ are each H, linear alkyl, cyclic alkyl or branched alkyl, and may be the same or different;

R$_3$ is H or a linear alkyl, cyclic alkyl or branched alkyl, n is an integer of from 0 to 20;

m is an integer of at least 1;

x is 1 or 2; and

A is said cell-binding agent.

20. The cytotoxic agent of claim 19, wherein Z–S is a thiol-containing maytansinoid.

21. The cytotoxic agent of claim 19, wherein Z–S is a thiol-containing taxane.

22. The cytotoxic agent of claim 19, wherein Z–S is a thiol-containing CC-1065.

23. The cytotoxic agent of claim 19, wherein Z–S is a thiol-containing daunorubicin.

24. The cytotoxic agent of claim 19, wherein Z–S is a thiol-containing doxorubicin.

25. A cytotoxic conjugate having one or more cytotoxic agents covalently bonded to a cell-binding agent through a PEG linking group having 21 to 40 monomeric units, of formula 3:

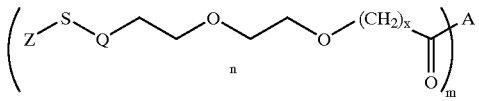

wherein:
Z–S is a thiol-containing cytotoxic agent;
Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$, wherein $R_4$, $R_5$ and $R_6$ are each H, linear alkyl, cyclic alkyl or branched alkyl, and may be the same or different;
$R_3$ is H or a linear alkyl, cyclic alkyl or branched alkyl;
n is an integer of from 21 to 40;
m is an integer of at least 1;
x is 1 or 2; and
A is said cell-binding agent.

26. The cytotoxic conjugate of claim 25, wherein Z–S is a thiol-containing maytansinoid.

27. The cytotoxic conjugate of claim 25, wherein Z–S is a thiol-containing taxane.

28. The cytotoxic conjugate of claim 25, wherein Z–S is a thiol-containing CC-1065.

29. The cytotoxic conjugate of claim 25, wherein Z–S is a thiol-containing daunorubicin.

30. The cytotoxic conjugate of claim 25, wherein Z–S is a thiol-containing doxorubicin.

31. A cytotoxic conjugate having one or more cytotoxic agents covalently bonded to a cell-binding agent through a PEG linking group having 41 to 1000 monomeric units, of formula 3:

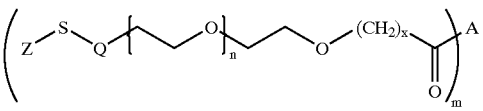

wherein:
Z–S is a thiol-containing cytotoxic agent;
Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$, wherein $R_4$, $R_5$ and $R_6$ are each H, linear alkyl, cyclic alkyl or branched alkyl, and may be the same or different;
$R_3$ is H or a linear alkyl, cyclic alkyl or branched alkyl;
n is an integer of from 41 to 1000;
m is an integer of at least 1;
x is 1 or 2; and
A is said cell-binding agent.

32. The cytotoxic conjugate of claim 31, wherein Z–S is a thiol-containing maytansinoid.

33. The cytotoxic conjugate of claim 31, wherein Z–S is a thiol-containing taxane.

34. The cytotoxic conjugate of claim 31, wherein Z–S is a thiol-containing CC-1065.

35. The cytotoxic conjugate of claim 31, wherein Z–S is a thiol-containing daunorubicin.

36. The cytotoxic conjugate of claim 31, wherein Z–S is a thiol-containing doxorubicin.

37. A therapeutic composition comprising a therapeutically-effective amount of the cytotoxic conjugate of claim 19, and a pharmaceutically acceptable carrier.

38. The therapeutic composition of claim 37, wherein Z–S is a thiol-containing maytansinoid.

39. The therapeutic composition of claim 37, wherein Z–S is a thiol-containing taxane.

40. The therapeutic composition of claim 37, wherein Z–S is a thiol-containing CC-1065.

41. The therapeutic composition of claim 37, wherein Z–S is a thiol-containing daunorubicin.

42. The therapeutic composition of claim 37, wherein Z–S is a thiol-containing doxorubicin.

43. A therapeutic composition comprising a therapeutically-effective amount of the cytotoxic conjugate of claim 25, and a pharmaceutically acceptable carrier.

44. The therapeutic composition of claim 43, wherein Z–S is a thiol-containing maytansinoid.

45. The therapeutic composition of claim 43, wherein Z–S is a thiol-containing taxane.

46. The therapeutic composition of claim 43, wherein Z–S is a thiol-containing CC-1065.

47. The therapeutic composition of claim 43, wherein Z–S is a thiol-containing daunorubicin.

48. The therapeutic composition of claim 43, wherein Z–S is a thiol-containing doxorubicin.

49. A therapeutic composition comprising a therapeutically-effective amount the cytotoxic conjugate of claim 31, and a pharmaceutically acceptable carrier.

50. The therapeutic composition of claim 49, wherein Z–S is a thiol-containing maytansinoid.

51. The therapeutic composition of claim 49, wherein Z–S is a thiol-containing taxane.

52. The therapeutic composition of claim 49, wherein Z–S is a thiol-containing CC-1065.

53. The therapeutic composition of claim 49, wherein Z–S is a thiol-containing daunorubicin.

54. The therapeutic composition of claim 49, wherein Z–S is a thiol-containing doxorubicin.

55. A method for producing a cytotoxic agent, bearing a PEG linking group having a terminal active ester and 1 to 20 monomeric units, of formula 2:

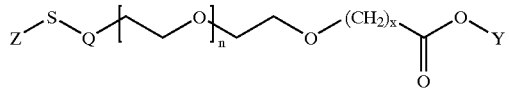

wherein:
Z–S is a thiol-containing cytotoxic agent;
Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$, wherein $R_4$, $R_5$ and $R_6$ are each H, linear alkyl, cyclic alkyl or branched alkyl and may be the same or different;
$R_3$ is H or a linear alkyl, cyclic alkyl or branched alkyl;
n is an integer of from 0 to 20;
x is 1 or 2; and
Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl;

said method comprising the steps of:
  a) reacting a PEG linking group having 1 to 20 monomeric units of formula 1:

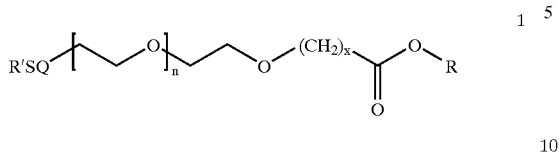

wherein:
    R' is 2-pyridyl, 4-pyridyl, 5-nitro-2-pyridyl, 5-nitro-4-pyridyl, 2-nitrophenyl, 4-nitrophenyl or 2,4-dinitrophenyl; and R is H, a cation to form a salt or a chemical group to form an ester, with a thiol-containing cytotoxic agent selected from the group consisting of a thiol-containing maytansinoid, a thiol-containing taxane, a thiol-containing CC-1065, a thiol-containing daunorubicin and a thiol-containing doxorubicin; and
  b) converting the R group of the product of step a) to an active ester, thereby producing a cytotoxic agent bearing a PEG linking group having a terminal active ester and 1 to 20 monomeric units.

56. The method of claim 55, wherein Z–S is a thiol-containing maytansinoid.

57. The method of claim 55, wherein Z–S is a thiol-containing taxane.

58. The method of claim 55, wherein Z–S is a thiol-containing CC-1065.

59. The method of claim 55, wherein Z–S is a thiol-containing daunorubicin.

60. The method of claim 55, wherein Z–S is a thiol-containing doxorubicin.

61. A method for producing a cytotoxic agent, bearing a PEG linking group having a terminal active ester and 21 to 40 monomeric units, of formula 2:

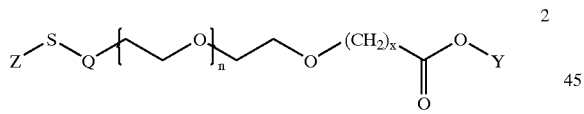

wherein:

Z–S is a thiol-containing cytotoxic agent;

Q is $R_2COO-$, $R_2R_3NCOO-$, $R_2OCOO-$, $R_2O-$, $R_2CONR_3-$, $R_2R_3N-$, $R_2OCONR_3-$, or $S-$,
  wherein:
    $R_2$ is $SCR_4R_5R_6-$, wherein $R_4$, $R_5$ and $R_6$ are each H, linear alkyl, cyclic alkyl or branched alkyl, and may be the same or different;
    $R_3$ is H or a linear alkyl, cyclic alkyl or branched alkyl;

n is an integer of from 21 to 40;

x is 1 or 2; and

Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl;

said method comprising the steps of:
  (a) reacting a PEG linking group having 21 to 40 monomeric units of formula 1:

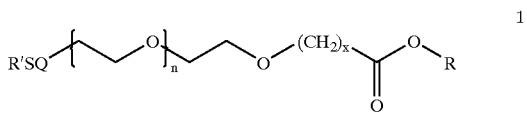

wherein:
    R' is 2-pyridyl, 4-pyridyl, 5-nitro-2-pyridyl, 5-nitro-4-pyridyl, 2-nitrophenyl, 4-nitrophenyl or 2,4-dinitrophenyl, and R is H, a cation to form a salt or a chemical group to form an ester, with a thiol-containing cytotoxic agent selected from the group consisting of a thiol-containing maytansinoid, a thiol-containing thiol-containing taxane, a thiol-containing CC-1065, a thiol-containing daunorubicin and a thiol-containing doxorubicin; and
  b) converting the R group of the product of step a) to an active ester, thereby producing a cytotoxic agent bearing a PEG linking group having a terminal active ester and 21 to 40 monomeric units.

62. The method of claim 47, wherein Z–S is a thiol-containing maytansinoid.

63. The method of claim 47, wherein Z–S is a thiol-containing taxane.

64. The method of claim 47, wherein Z–S is a thiol-containing CC-1065.

65. The method of claim 47, wherein Z–S is a thiol-containing daunorubicin.

66. The method of claim 47, wherein Z–S is a thiol-containing doxorubicin.

67. A method for producing a cytotoxic agent, bearing a PEG linking group having a terminal active ester and 41 to 1000 monomeric units, of formula 2:

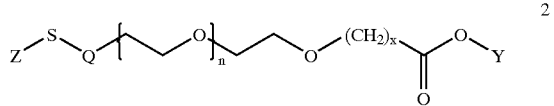

wherein:

Z–S is a thiol-containing cytotoxic agent;

Q is $R_2COO-$, $R_2R_3NCOO-$, $R_2OCOO-$, $R_2O-$, $R_2CONR_3-$, $R_2R_3N-$, $R_2OCONR_3-$, or $S-$,
  wherein:
    $R_2$ is $SCR_4R_5R_6-$, wherein $R_4$, $R_5$ and $R_6$ are each H, linear alkyl, cyclic alkyl or branched alkyl, and may be the same or different;
    $R_3$ is H or a linear alkyl, cyclic alkyl or branched alkyl;

n is an integer of from 41 to 1000;

x is 1 or 2; and

Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl;

said method comprising the steps of:
  a) reacting a PEG linking group having 41 to 1000 monomeric units of formula 1:

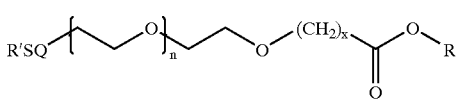

wherein:
R' is 2-pyridyl, 4-pyridyl, 5-nitro-2-pyridyl, 5-nitro-4-pyridyl, 2-nitrophenyl, 4-nitrophenyl or 2,4-dinitrophenyl; and R is H, a cation to form a salt or a chemical group to form an ester, with a thiol-containing cytotoxic agent selected from the group consisting of a thiol-containing maytansinoid, a thiol-containing taxane, a thiol-containing CC-1065, a thiol-containing daunorubicin and a thiol-containing doxorubicin; and b) converting the R group of the product of step a) to an active ester, thereby producing a cytotoxic agent bearing a PEG linking group having a terminal active ester and 41 to 1000 monomeric units.

68. The method of claim 67, wherein Z–S is a thiol-containing maytansinoid.

69. The method of claim 67, wherein Z–S is a thiol-containing taxane.

70. The method of claim 67, wherein Z–S is a thiol-containing CC-1065.

71. The method of claim 67, wherein Z–S is a thiol-containing daunorubicin.

72. The method of claim 67, wherein Z–S is a thiol-containing doxorubicin.

73. A method for producing a cytotoxic conjugate which has one or more cytotoxic agents covalently bonded to a cell-binding agent through a PEG linking group having 1 to 20 monomeric units, said method comprising reacting one or more cytotoxic agents with a cell-binding agent, wherein said one or more cytotoxic agents each bears a PEG linking group having a terminal active ester and 1 to 20 monomeric units, and wherein said cytotoxic agent bearing a PEG linking group having a terminal active ester and 1 to 20 monomeric units represented by formula 2:

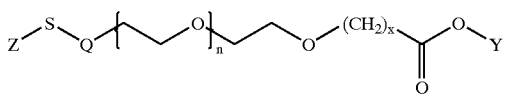

wherein:
Z–S is a thiol-containing cytotoxic agent;
Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$, wherein $R_4$, $R_5$ and $R_6$ are each H, linear alkyl, cyclic alkyl or branched alkyl, and may be the same or different;
$R_3$ is H or a linear alkyl, cyclic alkyl or branched alkyl;
n is an integer of from 0 to 20;
x is 1 or 2; and
Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl;

thereby producing a cytotoxic conjugate, of formula 3:

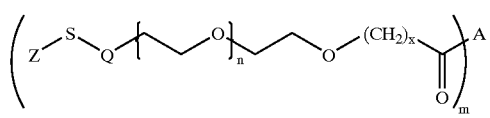

wherein:
m is an integer of at least 1; and A is said cell-binding agent.

74. The method of claim 59, wherein Z–S is a thiol-containing maytansinoid.

75. The method of claim 59, wherein Z–S is a thiol-containing taxane.

76. The method of claim 59, wherein Z–S is a thiol-containing CC-1065.

77. The method of claim 59, wherein Z–S is a thiol-containing daunorubicin.

78. The method of claim 59, wherein Z–S is a thiol-containing doxorubicin.

79. A method for producing a cytotoxic conjugate which has one or more cytotoxic agents covalently bonded to a cell-binding agent through a PEG linking group having 21 to 40 monomeric units, said method comprising reacting one or more cytotoxic agents with a cell-binding agent, wherein said one or more cytotoxic agents each bears a PEG linking group having a terminal active ester and 21 to 40 monomeric units, and wherein said cytotoxic agent bearing a PEG linking group having a terminal active ester and 21 to 40 monomeric units is represented by formula 2:

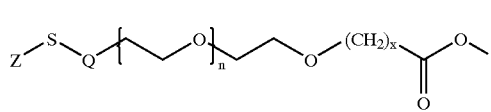

wherein:
Z–S is a thiol-containing cytotoxic agent;
Q is $R_2COO-$, $R_2R_3NCOO-$, $R_2OCOO-$, $R_2O-$, $R_2CONR_3-$, $R_2R_3N-$, $R_2OCONR_3-$, or $S-$,
wherein:
$R_2$ is $SCR_4R_5R_6-$, wherein $R_4$, $R_5$ and $R_6$ are each H, linear alkyl, cyclic alkyl or branched alkyl, and may be the same or different;
$R_3$ is H or a linear alkyl, cyclic alkyl or branched alkyl;
n is an integer of from 21 to 40;
x is 1 or 2; and
Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl;

thereby producing a cytotoxic conjugate of formula 3 with a linkage of one of said one or more cytotoxic agents

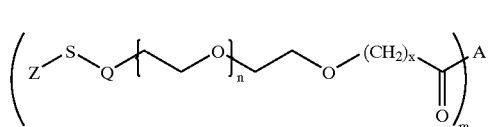

wherein m is an integer of at least 1; and A is said cell-binding agent.

80. The method of claim 79, wherein Z–S is a thiol-containing maytansinoid.

81. The method of claim 79, wherein Z–S is a thiol-containing taxane.

82. The method of claim 79, wherein Z–S is a thiol-containing CC-1065.

83. The method of claim 79, wherein Z–S is a thiol-containing daunorubicin.

84. The method of claim 79, wherein Z–S is a thiol-containing doxorubicin.

85. A method for producing a cytotoxic conjugate which has one or more cytotoxic agents covalently bonded to a cell-binding agent through a PEG linking group having 41 to 1000 monomeric units, said method comprising reacting one or more cytotoxic agents with a cell-binding agent, wherein said one or more cytotoxic agents each bears a PEG linking group having a terminal active ester and 41 to 1000 monomeric units, and wherein said cytotoxic agent bearing a PEG linking group having a terminal active ester and 41 to 1000 monomeric units represented by formula 2:

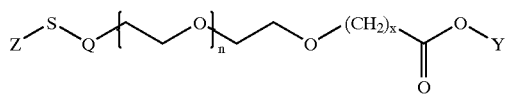

wherein:

Z–S is a thiol-containing cytotoxic agent;

Q is $R_2COO-$, $R_2R_3NCOO-$, $R_2OCOO-$, $R_2O-$, $R_2CONR_3-$, $R_2R_3N-$, $R_2OCONR_3-$, or S—, wherein:

$R_2$ is $SCR_4R_5R_6-$, wherein $R_4$, $R_5$ and $R_6$ are each H, linear alkyl, cyclic alkyl or branched alkyl, and may be the same or different;

$R_3$ is H or a linear alkyl, cyclic alkyl or branched alkyl;

n is an integer of from 41 to 1000;

x is 1 or 2; and

Y is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl;

thereby producing a cytotoxic conjugate of formula 3 with a linkage of one of said one or more cytotoxic agents

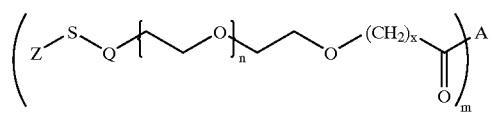

wherein: m is an integer of at least 1; and A is said cell-binding agent.

86. The method of claim 85, wherein Z–S is a thiol-containing maytansinoid.

87. The method of claim 85, wherein Z–S is a thiol-containing taxane.

88. The method of claim 85, wherein Z–S is a thiol-containing CC-1065.

89. The method of claim 85, wherein Z–S is a thiol-containing daunorubicin.

90. The method of claim 85, wherein Z–S is a thiol-containing doxorubicin.

91. The method according to any one of claims 73–90, wherein said method further comprises the initial step of preparing a cytotoxic agent, bearing a PEG linking group having a terminal active ester, said initial step comprising reacting a thiol-containing cytotoxic agent with a PEG linking group of formula 1:

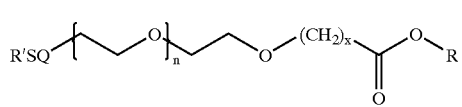

wherein R' is 2-pyridyl, 4-pyridyl, 5-nitro-2-pyridyl, 5-nitro-4-pyridyl, 2-nitrophenyl, 4-nitrophenyl or 2,4-dinitrophenyl; and R is H, a cation to form a salt or a chemical group to form an ester.

92. A method of killing selected cell populations by exposure to a cytotoxic conjugate of a cell binding agent that binds to target cells and a cytotoxic agent, comprising contacting the target cells, or tissue containing the target cells, with an effective amount of the cytotoxic conjugate of any one of claims 19–36.

* * * * *

UNITED STATES PATENT AND TRADEMARK OFFICE
CERTIFICATE OF CORRECTION

PATENT NO. : 6,716,821 B2  
APPLICATION NO. : 10/024290  
DATED : April 6, 2004  
INVENTOR(S) : Robert Y. Zhao et al.

It is certified that error appears in the above-identified patent and that said Letters Patent is hereby corrected as shown below:

Column 75, line 7, delete "20", insert -- 19 --

Column 75, line 47, delete "21 to 40", insert -- 20 to 39 --

Column 76, line 17, delete "41 to 1000", insert -- 40 to 999 --

Column 76, line 54, delete "20", insert -- 19 --

Column 77, line 22, delete "21 to 40", insert -- 20 to 39 --

Column 77, line 57, delete "41 to 1000", insert -- 40 to 999 --

Column 78, line 62, delete "20", insert -- 19 --

Column 79, line 61, delete "21 to 40", insert -- 20 to 39 --

Column 80, line 58, delete "41 to 1000", insert -- 40 to 999 --

Column 81, line 61, delete "20", insert -- 19 --

Column 82, line 48, delete "21 to 40", insert -- 20 to 39 --

Column 83, line 36, delete "41 to 1000", insert -- 40 to 999 --

Signed and Sealed this

Thirtieth Day of March, 2010

David J. Kappos
*Director of the United States Patent and Trademark Office*